(12) United States Patent
Zhou et al.

(10) Patent No.: US 9,896,510 B2
(45) Date of Patent: Feb. 20, 2018

(54) ANTI-HUMAN RANKL ANTIBODY, HUMANIZED ANTIBODY OF THE SAME, AND PHARMACEUTICAL COMPOSITION AND USE THEREOF

(71) Applicants: Qing Zhou, Pudong New District Shanghai (CN); Xiao Feng, Pudong New District Shanghai (CN); Weihong Nian, Pudong New District Shanghai (CN); Lingyun Li, Pudong New District Shanghai (CN)

(72) Inventors: Qing Zhou, Pudong New District Shanghai (CN); Xiao Feng, Pudong New District Shanghai (CN); Weihong Nian, Pudong New District Shanghai (CN); Lingyun Li, Pudong New District Shanghai (CN)

(73) Assignee: Genor Biopharma Co., Ltd., Shanghai (CN)

(*) Notice: Subject to any disclaimer, the term of this patent is extended or adjusted under 35 U.S.C. 154(b) by 0 days.

(21) Appl. No.: 14/757,970

(22) Filed: Dec. 23, 2015

(65) Prior Publication Data
US 2016/0333101 A1 Nov. 17, 2016

Related U.S. Application Data

(63) Continuation-in-part of application No. PCT/CN2014/095236, filed on Dec. 28, 2014.

(30) Foreign Application Priority Data

Dec. 31, 2013 (CN) .......................... 2013 1 0753972

(51) Int. Cl.
*C07K 16/00* (2006.01)
*C07K 16/28* (2006.01)

(52) U.S. Cl.
CPC ...... *C07K 16/2875* (2013.01); *C07K 2317/24* (2013.01); *C07K 2317/33* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS 8,414,890 B2 * 4/2013 Martin ............... C07K 16/2875
424/130.1

* cited by examiner

*Primary Examiner* — Laura B Goddard
(74) *Attorney, Agent, or Firm* — John P. White; Cooper & Dunham LLP

(57) ABSTRACT

An anti-human RANKL antibody, a humanized antibody for the anti-human RANKL antibody, a pharmaceutical composition and a use thereof are provided. The anti-human RANKL antibody is capable of bonding specifically with an amino acid sequence of SEQ ID NO.1, a heavy chain of the anti-human RANKL antibody includes a variable region in one of amino acid sequences of SEQ ID NO.2-9, and a light chain of the anti-human RANKL antibody includes a variable region in one of amino acid sequences of SEQ ID NO.10-17. The humanized antibody is capable of bonding specifically with human RANKL, a variable region in a heavy chain of the humanized antibody is selected from amino acid sequences of SEQ ID NO.6, NO.23, NO.25, NO.27 or NO.29, and a variable region in a light chain of the humanized antibody is selected from amino acid sequences of SEQ ID NO.14, NO.31, NO.33, NO.35, NO.37 or NO.39.

21 Claims, 8 Drawing Sheets

TGTCCACTCCCAGGTCCAAGTTTAAACGGATCTCTAGCGAATTCACCGCAGAGGCTTG
GGGCAGCCGAGCGGCAGGCAGGCCGGGCCGGGCCTGGGTTCCAGAAGGGAGAGG
AGGCCGGCAAGGCGGCAAGAGAGCCGGCTGCCTGGCAGTCGGAGGCGGAGAGGGAG
CGCGAGCCGCGCCGGCCGGACCGCCTCCGAAACCATGGAGTTGGGACTGTCTTGG
ATTTTCCTTGTTGCTATTCTGAAAGGTGCAGTGTCATCAGCATCATCATCATCAT
CACCACCACCGCCGGAGGAAGCGGAGGCGCAGCGGAGGGGAAGCATTGAGGCGG
CGGCTGCTCAGGAGCATCAGGGCGGAGAAGGCTATGGTGGAGGAAGCTGGCTGGACCTG
GGCAAAAGGTGCAAACTGGAGGCTCAGCCATTTGCCCACCTGACAATCAACGCTACC
GACATGCCCAGGTGGAAGGCACAAGGTGAGGCTGAGCTGCTGGTATCACGACAGGGCT
GGGCCAAGATCAGCAACATGACCTTCAGCAATGGGAAGCTGATCGTGAATCAAGAGG
GCTTTTACTACCTGTACGGCAACATCTGTTTCAGACATCACGAGACCAGCGGCGATCT
GGGCACAAGTACCTGCAACTGATGGTCTATGTGACTAAAACAAGCATCAAAATGCCCT
TGCTGCCACACTGTGATGAAGGGGCGAGCCACCAAGTATTGCAGCGGGCAACAGCGAG
TTCCACTTCTACTGCATTAAGTCGGCGGCTTCTTTAAAGCTGAGGTCGGGCGAAGAAAT
CTGCATGGAGCTGTCCAATTCCAGCCTGCTGGACCCGATCAGGAGCCAACCTGCTTC
GGGCGCTTCAAGGTCAGGGACATGACTGACATCCCGGAGCTGGACCTGTGGCTAA
TAAAGGAAATTTATTTTCATTGCAATAGTGTGTT

Figure 1

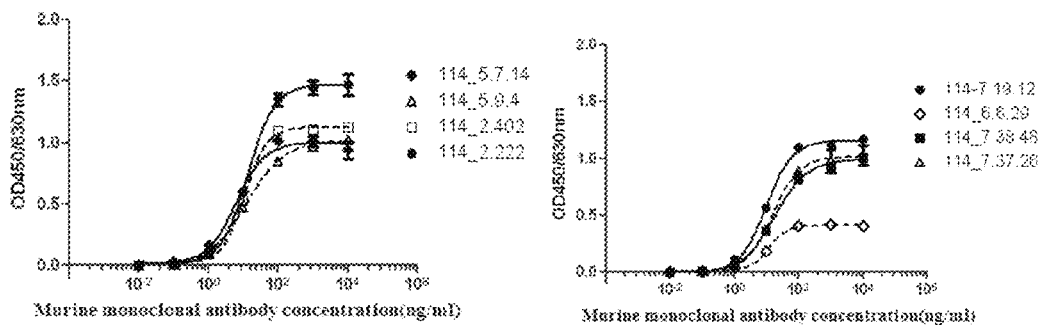

Figure 2

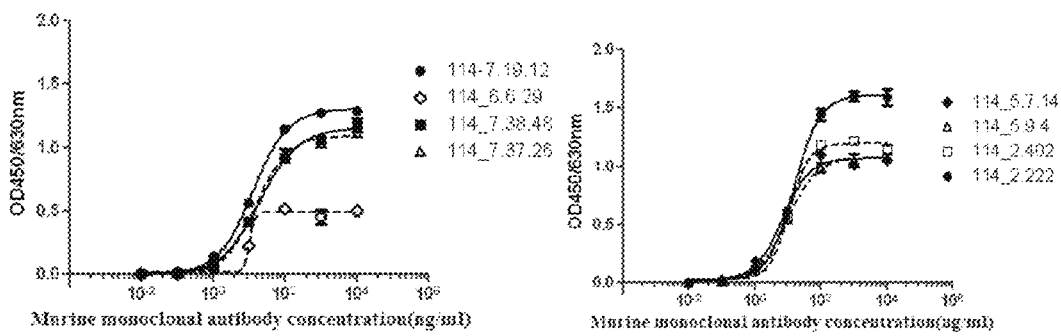

Figure 3

SEQUENCE LISTING

```
<160> NUMBER OF SEQ ID NOS: 56

<210> SEQ ID NO 1
<211> LENGTH: 182
<212> TYPE: PRT
<213> ORGANISM: Homo sapiens

<400> SEQUENCE: 1

Gly Ser Gln His Ile Arg Ala Glu Lys Ala Met Val Asp Gly Ser Trp
1               5                   10                  15

Leu Asp Leu Ala Lys Arg Ser Lys Leu Glu Ala Gln Pro Phe Ala His
            20                  25                  30

Leu Thr Ile Asn Ala Thr Asp Ile Pro Ser Gly Ser His Lys Val Ser
        35                  40                  45

Leu Ser Ser Trp Tyr His Asp Arg Gly Trp Ala Lys Ile Ser Asn Met
    50                  55                  60

Thr Phe Ser Asn Gly Lys Leu Ile Val Asn Gln Asp Gly Phe Tyr Tyr
65                  70                  75                  80

Leu Tyr Ala Asn Ile Cys Phe Arg His His Glu Thr Ser Gly Asp Leu
                85                  90                  95

Ala Thr Glu Tyr Leu Gln Leu Met Val Tyr Val Thr Lys Thr Ser Ile
            100                 105                 110

Lys Ile Pro Ser Ser His Thr Leu Met Lys Gly Gly Ser Thr Lys Tyr
        115                 120                 125

Trp Ser Gly Asn Ser Glu Phe His Phe Tyr Ser Ile Asn Val Gly Gly
    130                 135                 140

Phe Phe Lys Leu Arg Ser Gly Glu Glu Ile Ser Ile Glu Val Ser Asn
145                 150                 155                 160

Pro Ser Leu Leu Asp Pro Asp Gln Asp Ala Thr Tyr Phe Gly Ala Phe
                165                 170                 175

Lys Val Arg Asp Ile Asp
            180

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Ala Glu Leu Val Lys Pro Gly Ala
1               5                   10                  15

Ser Val Lys Leu Ser Cys Thr Thr Ser Gly Phe Asn Ile Lys Ala Thr
            20                  25                  30

Tyr Ile His Trp Val Gln Gln Arg Pro Glu Gln Gly Leu Glu Trp Ile
        35                  40                  45

Gly Arg Ile Asp Pro Ala Asn Gly Asn Thr Lys Tyr Asp Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
```

```
                    85                  90                  95
Ala Arg Ser Leu His Tyr Tyr Val Phe Phe Asp Tyr Trp Gly Gln Gly
            100                 105                 110

Thr Thr Leu Thr Val Ser Ser
            115

<210> SEQ ID NO 3
<211> LENGTH: 120
<212> TYPE: PRT
<213> ORGANISM: Mus musculus

<400> SEQUENCE: 3

Glu Val Gln Leu Gln Gln Ser Gly Thr Glu Leu Val Lys Pro Gly Ala
1               5                   10                  15

Ser Val Lys Leu Ser Cys Thr Leu Phe Gly Phe Asn Ile Lys Ala Thr
            20                  25                  30

Tyr Met His Trp Val Arg Gln Arg Pro Glu Gln Gly Leu Glu Trp Ile
        35                  40                  45

Gly Arg Ile Asp Pro Asn Gly Asn Thr Lys Tyr Asp Pro Lys Phe
    50                  55                  60

Gln Asp Lys Ala Thr Ile Lys Val Asp Thr Ser Ser Asn Thr Ala Tyr
65                  70                  75                  80

Leu Gln Leu Ser Ser Leu Thr Ser Glu Asp Thr Ala Val Tyr Tyr Cys
            85                  90                  95

Ala Arg Glu Phe Asn Arg Tyr Asp Val Trp Leu Ala Tyr Trp Gly Gln
            100                 105                 110

Gly Thr Leu Val Thr Val Ser Ala
            115                 120

<210> SEQ ID NO 4
<211> LENGTH: 120
<212> TYPE: PRT
<213> ORGANISM: Mus musculus

<400> SEQUENCE: 4

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Leu Lys Gly Thr
            20                  25                  30

Tyr Ile His Trp Val Lys Gln Arg Pro Gly Gln Gly Leu Glu Trp Ile
        35                  40                  45

Gly Arg Ile Asp Pro Ala Asn Ala Asn Thr Lys Tyr Asp Pro Lys Phe
    50                  55                  60

Gln Gly Lys Ala Thr Ile Arg Thr Asp Thr Ser Ser Asn Thr Ala Tyr
65                  70                  75                  80

Leu Gln Leu Ser Ser Leu Thr Ser Glu Asp Thr Ala Val Tyr Phe Cys
            85                  90                  95

Ser Ser Pro Ser Gly His Tyr Asp Val Trp Phe Ala Tyr Trp Gly Gln
            100                 105                 110

Gly Thr Leu Val Thr Val Ser Pro
            115                 120

<210> SEQ ID NO 5
<211> LENGTH: 120
<212> TYPE: PRT
<213> ORGANISM: Mus musculus

<400> SEQUENCE: 5
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Met His Trp Val Arg Gln Arg Pro Glu Gln Gly Leu Glu Trp Ile
        35                  40                  45

Gly Arg Ile Asp Ser Ala Asn Gly Asn Ile Lys Tyr Asp Pro Lys Phe
    50                  55                  60

Gln Gly Lys Ala Thr Ile Thr Ala Asp Thr Ser Lys Thr Ala Tyr
65                  70                  75                  80

Leu His Leu Ser Ser Leu Thr Phe Glu Asp Thr Ala Val Tyr Tyr Cys
                85                  90                  95

Ser Arg Pro Lys Ser Asn Tyr Asp Phe Trp Leu Pro Tyr Trp Gly Gln
            100                 105                 110

Gly Thr Leu Val Thr Val Ser Ala
        115                 120

<210> SEQ ID NO 6
<211> LENGTH: 118
<212> TYPE: PRT
<213> ORGANISM: Mus musculus

<400> SEQUENCE: 6

Gln Val Gln Leu Gln Gln Ser Gly Ala Glu Leu Ala Ser Pro Gly Ala
1               5                   10                  15

Ser Val Lys Leu Ser Cys Lys Ala Ser Gly Tyr Thr Phe Thr Thr Tyr
            20                  25                  30

Trp Leu Gln Trp Val Lys Gln Arg Pro Gly Gln Gly Leu Glu Trp Ile
        35                  40                  45

Gly Ala Ile Tyr Pro Gly Pro Gly Asn Thr Lys Tyr Thr Gln Lys Phe
    50                  55                  60

Lys Asp Lys Ala Thr Leu Thr Ala Asp Lys Ser Ala Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Gly Ser Arg Gly Ile Ala Tyr Trp Gly Gln Gly Thr
            100                 105                 110

Leu Val Thr Val Ser Ala
        115

<210> SEQ ID NO 7
<211> LENGTH: 118
<212> TYPE: PRT
<213> ORGANISM: Mus musculus

<400> SEQUENCE: 7

Gln Val Gln Leu Gln Gln Ser Gly Ala Glu Leu Ala Ser Pro Gly Ala
1               5                   10                  15

Ser Val Lys Leu Ser Cys Lys Thr Ser Gly Tyr Thr Phe Thr Thr Tyr
            20                  25                  30

Trp Leu Gln Trp Val Lys Gln Arg Pro Gly Gln Gly Leu Glu Trp Ile
        35                  40                  45

Gly Ala Ile Tyr Pro Gly Pro Gly Asn Thr Lys Tyr Thr Gln Lys Phe
    50                  55                  60

Lys Asp Lys Ala Thr Leu Thr Ala Asp Lys Ser Ala Ser Thr Ala Tyr
65                  70                  75                  80

```
Met Gln Leu Ser Ser Leu Thr Ser Glu Asp Ser Ala Val Tyr Tyr Cys
                85                  90                  95

Ala Arg Arg Gly Ser Arg Gly Ile Ala Tyr Trp Gly Gln Gly Thr
            100                 105                 110

Leu Val Thr Val Ser Ala
        115

<210> SEQ ID NO 8
<211> LENGTH: 117
<212> TYPE: PRT
<213> ORGANISM: Mus musculus

<400> SEQUENCE: 8

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Ala
            20                  25                  30

Tyr Ser Trp His Trp Ile Arg Gln Phe Pro Gly Asn Lys Leu Glu Trp
        35                  40                  45

Met Gly Tyr Ile His Phe Ser Gly Val Thr Asn Tyr Asn Pro Ser Leu
    50                  55                  60

Lys Ser Arg Ile Ser Ile Thr Arg Asp Ala Ser Lys Asn Gln Phe Phe
65                  70                  75                  80

Leu Gln Leu Ser Ser Val Thr Thr Glu Asp Thr Ala Thr Tyr Tyr Cys
                85                  90                  95

Ala Thr Arg Arg Glu Thr Gly Thr Tyr Phe Thr Tyr Trp Gly Gln Gly Thr Leu
            100                 105                 110

Val Thr Val Ser Ala
        115

<210> SEQ ID NO 9
<211> LENGTH: 126
<212> TYPE: PRT
<213> ORGANISM: Mus musculus

<400> SEQUENCE: 9

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Trp Asp Tyr Tyr Gly Thr Thr Tyr Val Gly Gly Tyr Ala
            100                 105                 110

Met Asp Tyr Trp Gly Gln Gly Thr Ser Val Thr Val Ser Ser
        115                 120                 125

<210> SEQ ID NO 10
<211> LENGTH: 108
<212> TYPE: PRT
<213> ORGANISM: Mus musculus
```

```
<400> SEQUENCE: 10

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Ser Thr Ser Ser Leu His Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Ile Ala Thr Tyr Tyr Cys Gln Gln Tyr Ser Lys Leu Pro Leu
                85                  90                  95

Thr Phe Gly Ala Gly Thr Lys Leu Glu Leu Lys Arg
            100                 105

<210> SEQ ID NO 11
<211> LENGTH: 108
<212> TYPE: PRT
<213> ORGANISM: Mus musculus

<400> SEQUENCE: 11

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Val Ser Asn Tyr
            20                  25                  30

Leu Asn Trp Tyr Gln Gln Lys Pro Asp Gly Thr Val Lys Leu Leu Ile
        35                  40                  45

Tyr Ser Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Val Ala Thr Tyr Tyr Cys Gln Gln Tyr Ser Lys Leu Pro Phe
                85                  90                  95

Thr Phe Gly Ser Gly Thr Lys Leu Glu Ile Lys Arg
            100                 105

<210> SEQ ID NO 12
<211> LENGTH: 108
<212> TYPE: PRT
<213> ORGANISM: Mus musculus

<400> SEQUENCE: 12

Asp Ile Gln Met Thr Gln Pro Thr Ser Ser Leu Ser Ala Ser Leu Gly
1               5                   10                  15

Asp Thr Val Thr Ile Ser Cys Ser Ala Ser Gln Asp Ile Ser Asn Tyr
            20                  25                  30

Leu Asn Trp Tyr Gln Gln Lys Pro Asp Gly Thr Leu Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Phe Ser Lys Leu Pro Leu
                85                  90                  95
```

```
Thr Phe Gly Ala Gly Thr Lys Leu Glu Leu Lys Arg
            100                 105

<210> SEQ ID NO 13
<211> LENGTH: 107
<212> TYPE: PRT
<213> ORGANISM: Mus musculus

<400> SEQUENCE: 13

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Leu
                85                  90                  95

Thr Phe Gly Ala Gly Thr Lys Leu Glu Leu Lys
            100                 105

<210> SEQ ID NO 14
<211> LENGTH: 111
<212> TYPE: PRT
<213> ORGANISM: Mus musculus

<400> SEQUENCE: 14

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Arg Pro Gly Gln Pro Pro
        35                  40                  45

Thr Leu Leu Ile Tyr Leu Ala Ser Asn Leu Glu Ser Gly Val Pro Val
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asp Asn
                85                  90                  95

Glu Asp Pro Tyr Thr Phe Gly Gly Gly Thr Lys Leu Glu Ile Lys
            100                 105                 110

<210> SEQ ID NO 15
<211> LENGTH: 111
<212> TYPE: PRT
<213> ORGANISM: Mus musculus

<400> SEQUENCE: 15

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Arg Pro Gly Gln Pro Pro
        35                  40                  45

Thr Leu Leu Ile Tyr Leu Ala Ser Asn Leu Glu Ser Gly Val Pro Ala
```

```
Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asp Asn
                 85                  90                  95

Glu Asp Pro Tyr Thr Phe Gly Gly Gly Thr Lys Leu Glu Ile Lys
            100                 105                 110
```

<210> SEQ ID NO 16
<211> LENGTH: 107
<212> TYPE: PRT
<213> ORGANISM: Mus musculus

<400> SEQUENCE: 16

```
Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Lys Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Ile Tyr Phe Cys Gln Gln Ile Asn Ser Trp Pro Leu
                 85                  90                  95

Thr Phe Gly Ala Gly Thr Lys Leu Glu Leu Lys
            100                 105
```

<210> SEQ ID NO 17
<211> LENGTH: 112
<212> TYPE: PRT
<213> ORGANISM: Mus musculus

<400> SEQUENCE: 17

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
            100                 105                 110
```

<210> SEQ ID NO 18
<211> LENGTH: 354
<212> TYPE: DNA
<213> ORGANISM: Mus musculus

<400> SEQUENCE: 18

```
caggttcagc tccagcagtc tggggctgaa ctggcgagtc ctggggcttc agtgaagttg    60
```

| | |
|---|---|
| tcctgcaagg cttctggcta cacctttact acctactggc tgcagtgggt aaagcagagg | 120 |
| cctggacagg gtctggaatg gattgggget atttatcctg gacctggtaa tactaaatac | 180 |
| actcagaagt tcaaggacaa ggccacattg actgcagata atccgccag cacagcctac | 240 |
| atgcaactca acagcttgac atctgaagac tctgcggtct attactgcgc aaggagggga | 300 |
| tcacgacggg ggattgctta ctggggccaa gggactctgg tcactgtctc tgca | 354 |

<210> SEQ ID NO 19
<211> LENGTH: 333
<212> TYPE: DNA
<213> ORGANISM: Mus musculus

<400> SEQUENCE: 19

| | |
|---|---|
| aacattgtgc tgacccaatc tccagcttct ttggctgtgt ctctaggcca gagggccacc | 60 |
| atttcctgca gagccagtga aagtgttgat agttatggca gaagttttat gcactggtac | 120 |
| cagcagagac caggacagcc acccacactc ctcatctatc ttgcatccaa cctagaatct | 180 |
| ggggtccctg tcaggttcag tggcagtggg tctaggacag acttcaccct caccattgat | 240 |
| cctgtggagg ctgatgatgc tgcaacctat tactgtcagc aagataatga ggatccgtac | 300 |
| acgttcggag gggggaccaa gctggaaata aaa | 333 |

<210> SEQ ID NO 20
<211> LENGTH: 744
<212> TYPE: DNA
<213> ORGANISM: Mus musculus

<400> SEQUENCE: 20

| | |
|---|---|
| caggttcagc tccagcagtc tggggctgaa ctggcgagtc ctggggcttc agtgaagttg | 60 |
| tcctgcaagg cttctggcta cacctttact acctactggc tgcagtgggt aaagcagagg | 120 |
| cctggacagg gtctggaatg gattgggget atttatcctg gacctggtaa tactaaatac | 180 |
| actcagaagt tcaaggacaa ggccacattg actgcagata atccgccag cacagcctac | 240 |
| atgcaactca acagcttgac atctgaagac tctgcggtct attactgcgc aaggagggga | 300 |
| tcacgacggg ggattgctta ctggggccaa gggactctgg tcactgtctc tgcagcctcg | 360 |
| agtggtggtg gcggttcagg cggtggtggc tctggtggcg gtgggagctc taacattgtg | 420 |
| ctgacccaat ctccagcttc tttggctgtg tctctaggcc agagggccac catttcctgc | 480 |
| agagccagtg aaagtgttga tagttatggc agaagtttta tgcactggta ccagcagaga | 540 |
| ccaggacagc cacccacact cctcatctat cttgcatcca acctagaatc tggggtccct | 600 |
| gtcaggttca gtggcagtgg gtctaggaca gacttcaccc tcaccattga tcctgtggag | 660 |
| gctgatgatg ctgcaaccta ttactgtcag caagataatg aggatccgta cacgttcgga | 720 |
| ggggggacca agctggaaat aaaa | 744 |

<210> SEQ ID NO 21
<211> LENGTH: 248
<212> TYPE: PRT
<213> ORGANISM: Mus musculus

<400> SEQUENCE: 21

Gln Val Gln Leu Gln Gln Ser Gly Ala Glu Leu Ala Ser Pro Gly Ala
1               5                   10                  15

Ser Val Lys Leu Ser Cys Lys Ala Ser Gly Tyr Thr Phe Thr Thr Tyr
            20                  25                  30

Trp Leu Gln Trp Val Lys Gln Arg Pro Gly Gln Gly Leu Glu Trp Ile

Gly Ala Ile Tyr Pro Gly Pro Gly Asn Thr Lys Tyr Thr Gln Lys Phe
            35                  40                  45
    50                              55                  60

Lys Asp Lys Ala Thr Leu Thr Ala Asp Lys Ser Ala Ser Thr Ala Tyr
65                      70                  75                  80

Met Gln Leu Asn Ser Leu Thr Ser Glu Asp Ser Ala Val Tyr Tyr Cys
                85                  90                  95

Ala Arg Arg Gly Ser Arg Arg Gly Ile Ala Tyr Trp Gly Gln Gly Thr
                100                 105                 110

Leu Val Thr Val Ser Ala Ala Ser Ser Gly Gly Gly Ser Gly Gly
            115                 120                 125

Gly Gly Ser Gly Gly Gly Ser Ser Asn Ile Val Leu Thr Gln Ser
    130                 135                 140

Pro Ala Ser Leu Ala Val Ser Leu Gly Gln Arg Ala Thr Ile Ser Cys
145                 150                 155                 160

Arg Ala Ser Glu Ser Val Asp Ser Tyr Gly Arg Ser Phe Met His Trp
                165                 170                 175

Tyr Gln Gln Arg Pro Gly Gln Pro Pro Thr Leu Leu Ile Tyr Leu Ala
                180                 185                 190

Ser Asn Leu Glu Ser Gly Val Pro Val Arg Phe Ser Gly Ser Gly Ser
            195                 200                 205

Arg Thr Asp Phe Thr Leu Thr Ile Asp Pro Val Glu Ala Asp Asp Ala
210                 215                 220

Ala Thr Tyr Tyr Cys Gln Gln Asp Asn Glu Asp Pro Tyr Thr Phe Gly
225                 230                 235                 240

Gly Gly Thr Lys Leu Glu Ile Lys
                245

<210> SEQ ID NO 22
<211> LENGTH: 354
<212> TYPE: DNA
<213> ORGANISM: Artificial Sequence
<220> FEATURE:
<223> OTHER INFORMATION: Synthesized

<400> SEQUENCE: 22
caggttcagc tcgtgcagtc tggggctgaa ctgaagaagc ctggggcttc agtgaagttg     60
tcctgcaagg cttctggcta caccttact acctactggc tgcagtgggt aaggcaggct    120
cctggacagg gtctggaatg gatggggct atttatcctg acctggtaa tactaaatac     180 actcagaagt tcaaggacag attcacaatt actgcagata gtccaagag cacagcctac    240 atgcaactca acagcttgaa gtctgaagac tctgcggtct attactgcgc aaggagggga    300
tcacgacggg ggattgctta ctggggccaa gggactctgg tcactgtctc tgca          354

<210> SEQ ID NO 23
<211> LENGTH: 118
<212> TYPE: PRT
<213> ORGANISM: Artificial Sequence
<220> FEATURE:
<223> OTHER INFORMATION: Synthesized

<400> SEQUENCE: 23

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Thr Tyr
            20                  25                  30

Trp Leu Gln Trp Val Arg Gln Ala Pro Gly Gln Gly Leu Glu Trp Met
        35                  40                  45

Gly Ala Ile Tyr Pro Gly Pro Gly Asn Thr Lys Tyr Thr Gln Lys Phe
 50                  55                  60

Lys Asp Arg Phe Thr Ile Thr Ala Asp Lys Ser Lys Ser Thr Ala Tyr
65                  70                  75                  80

Met Gln Leu Asn Ser Leu Lys Ser Glu Asp Ser Ala Val Tyr Tyr Cys
                85                  90                  95

Ala Arg Arg Gly Ser Arg Gly Ile Ala Tyr Trp Gly Gln Gly Thr
            100                 105                 110

Leu Val Thr Val Ser Ala
        115

<210> SEQ ID NO 24
<211> LENGTH: 354
<212> TYPE: DNA
<213> ORGANISM: Artificial Sequence
<220> FEATURE:
<223> OTHER INFORMATION: Synthesized

<400> SEQUENCE: 24
caggttcagc tcgtgcagtc tggggctgaa ctgaagaagc ctggggcttc agtgaagttg        60
tcctgcaagg cttctggcta cacctttact acctactggc tgcagtgggt aaggcaggct       120
cctggacagg tctggaatg gatgggggct atttatcctg gacctggtaa tactaaatac       180
actcagaagt tcaaggacag attcacaatt actgcagata cgtccaagag cacagcctac       240
atgcaactca acagcttgaa gtctgaagac tctgcggtct attactgcgc aaggagggga       300
tcacgacggg ggattgctta ctggggccaa gggactctgg tcactgtctc tgca              354

<210> SEQ ID NO 25
<211> LENGTH: 118
<212> TYPE: PRT
<213> ORGANISM: Artificial Sequence
<220> FEATURE:
<223> OTHER INFORMATION: Synthesized

<400> SEQUENCE: 25

Gln Val Gln Leu Val Gln Ser Gly Ala Glu Leu Lys Lys Pro Gly Ala
1               5                  10                  15

Ser Val Lys Leu Ser Cys Lys Ala Ser Gly Tyr Thr Phe Thr Thr Tyr
            20                  25                  30

Trp Leu Gln Trp Val Arg Gln Ala Pro Gly Gln Gly Leu Glu Trp Met
        35                  40                  45

Gly Ala Ile Tyr Pro Gly Pro Gly Asn Thr Lys Tyr Thr Gln Lys Phe
 50                  55                  60

Lys Asp Arg Phe Thr Ile Thr Ala Asp Thr Ser Lys Ser Thr Ala Tyr
65                  70                  75                  80

Met Gln Leu Asn Ser Leu Lys Ser Glu Asp Ser Ala Val Tyr Tyr Cys
                85                  90                  95

Ala Arg Arg Gly Ser Arg Gly Ile Ala Tyr Trp Gly Gln Gly Thr
            100                 105                 110

Leu Val Thr Val Ser Ala
        115

<210> SEQ ID NO 26
<211> LENGTH: 354
<212> TYPE: DNA
<213> ORGANISM: Artificial Sequence

```
<220> FEATURE:
<223> OTHER INFORMATION: Synthesized

<400> SEQUENCE: 26
caggttcagc tcgtgcagtc tggggctgaa ctggtgcagc ctggggcttc agtgaagttg      60
tcctgcaagg cttctggcta cacctttact acctactggc tgcagtgggt aaggcagact     120
cctggacagg gtctggaatg gatggggct atttatcctg gacctggtaa tactaaatac     180
actcagaagt tcaaggacag ggtcacaatt actgcagata catccaccag cacagcctac     240
atgcaactca acagcttgag atctgaagac tctgcggtct attactgcgc aaggaggga     300 tcacgcggg ggattgctta ctggggccaa gggactctgg tcactgtctc tgca            354

<210> SEQ ID NO 27
<211> LENGTH: 118
<212> TYPE: PRT
<213> ORGANISM: Artificial Sequence
<220> FEATURE:
<223> OTHER INFORMATION: Synthesized

<400> SEQUENCE: 27

Gln Val Gln Leu Val Gln Ser Gly Ala Glu Leu Val Gln Pro Gly Ala
1               5                   10                  15

Ser Val Lys Leu Ser Cys Lys Ala Ser Gly Tyr Thr Phe Thr Thr Tyr
                20                  25                  30

Trp Leu Gln Trp Val Arg Gln Thr Pro Gly Gln Gly Leu Glu Trp Met
            35                  40                  45

Gly Ala Ile Tyr Pro Gly Pro Gly Asn Thr Lys Tyr Thr Gln Lys Phe
        50                  55                  60

Lys Asp Arg Val Thr Ile Thr Ala Asp Thr Ser Thr Ser Thr Ala Tyr
65                  70                  75                  80

Met Gln Leu Asn Ser Leu Arg Ser Glu Asp Ser Ala Val Tyr Tyr Cys
                85                  90                  95

Ala Arg Arg Gly Ser Arg Arg Gly Ile Ala Tyr Trp Gly Gln Gly Thr
            100                 105                 110

Leu Val Thr Val Ser Ala
        115

<210> SEQ ID NO 28
<211> LENGTH: 354
<212> TYPE: DNA
<213> ORGANISM: Artificial Sequence
<220> FEATURE:
<223> OTHER INFORMATION: Synthesized

<400> SEQUENCE: 28
caggttcagc tggtgcagtc tggagctgag gtgaagaagc tggggcctc agtgaaggtc      60 tcctgcaagg cttctggtta cacctttacc acctactggc tgcagtgggt aaggcaggct    120
cctggacagg gtctggaatg gatggggct atttatcctg gacctggtaa tactaaatac     180
actcagaagt tcaaggacag agtcacgatt accgcggacg aatccacgag cacagcctac    240
atggagctga gcagcctgag atctgaggac acggccgtgt attactgtgc gagaagggga    300
tcacgacggg ggattgctta ctggggccaa gggactctgg tcactgtctc tgca           354

<210> SEQ ID NO 29
<211> LENGTH: 118
<212> TYPE: PRT
<213> ORGANISM: Artificial Sequence
<220> FEATURE:
```

<223> OTHER INFORMATION: Synthesized

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Leu Gln Trp Val Arg Gln Ala Pro Gly Gln Gly Leu Glu Trp Met
        35                  40                  45

Gly Ala Ile Tyr Pro Gly Pro Gly Asn Thr Lys Tyr Thr Gln Lys Phe
    50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Arg Gly Ile Ala Tyr Trp Gly Gln Gly Thr
            100                 105                 110

Leu Val Thr Val Ser Ala
        115
```

<210> SEQ ID NO 30
<211> LENGTH: 333
<212> TYPE: DNA
<213> ORGANISM: Artificial Sequence
<220> FEATURE:
<223> OTHER INFORMATION: Synthesized

<400> SEQUENCE: 30

```
aacattgtgc tgacccaatc tccagcttct ttgtctgtgt ctctaggcca gagggccacc    60
atttcctgca gagccagtga aagtgttgat agttatggca gaagtttat  gcactggtac   120
cagcagagac caggacaggc tcccagactc ctcatctatc ttgcatccaa cctagaatct   180
ggggtccctg ccaggttcag tggcagtggg tctaggacag acttcaccct caccattagc   240
agtgtggagg ctgaagatga ggcaacctat tactgtcagc aagataatga ggatccgtac   300
acgttcggag gggggaccaa gctggaaata aaa                                333
```

<210> SEQ ID NO 31
<211> LENGTH: 111
<212> TYPE: PRT
<213> ORGANISM: Artificial Sequence
<220> FEATURE:
<223> OTHER INFORMATION: Synthesized

<400> SEQUENCE: 31

```
Asn Ile Val Leu Thr Gln Ser Pro Ala Ser Leu Ser Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Arg Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Ser
65                  70                  75                  80

Ser Val Glu Ala Glu Asp Glu Ala Thr Tyr Tyr Cys Gln Gln Asp Asn
                85                  90                  95

Glu Asp Pro Tyr Thr Phe Gly Gly Gly Thr Lys Leu Glu Ile Lys
```

<210> SEQ ID NO 32
<211> LENGTH: 333
<212> TYPE: DNA
<213> ORGANISM: Artificial Sequence
<220> FEATURE:
<223> OTHER INFORMATION: Synthesized

<400> SEQUENCE: 32

```
aacattgtgc tgacccaatc tccagcttct ttgtctgtgt ctctaggcca gagggccacc      60
atttcctgca gagccagtga aagtgttgat agttatggca aagtttttat gcactggtac     120
cagcagagac caggacaggc tcccaaactc ctcatctatc ttgcatccaa cctagaatct     180
ggggtccctg ccaggttcag tggcagtggg tctaggacag acttcaccct caccattagc     240
agtgtggagg ctgaagatga ggcaacctat tactgtcagc aagataatga ggatccgtac     300
acgttcggag gggggaccaa gctggaaata aaa                                   333
```

<210> SEQ ID NO 33
<211> LENGTH: 111
<212> TYPE: PRT
<213> ORGANISM: Artificial Sequence
<220> FEATURE:
<223> OTHER INFORMATION: Synthesized

<400> SEQUENCE: 33

```
Asn Ile Val Leu Thr Gln Ser Pro Ala Ser Leu Ser Val Ser Leu Gly
1               5                   10                  15
Gln Arg Ala Thr Ile Ser Cys Arg Ala Ser Glu Ser Val Asp Ser Tyr
            20                  25                  30
Gly Arg Ser Phe Met His Trp Tyr Gln Gln Arg Pro Gly Gln Ala Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Arg Thr Asp Phe Thr Leu Thr Ile Ser
65                  70                  75                  80
Ser Val Glu Ala Glu Asp Glu Ala Thr Tyr Tyr Cys Gln Gln Asp Asn
                85                  90                  95
Glu Asp Pro Tyr Thr Phe Gly Gly Gly Thr Lys Leu Glu Ile Lys
            100                 105                 110
```

<210> SEQ ID NO 34
<211> LENGTH: 333
<212> TYPE: DNA
<213> ORGANISM: Artificial Sequence
<220> FEATURE:
<223> OTHER INFORMATION: Synthesized

<400> SEQUENCE: 34

```
aacattgtgc tgacccaatc tccagcttct ttgtctgtgt ctctaggcca gagggccacc      60
atttcctgca gagccagtga aagtgttgat agttatggca aagtttttat gcactggtac     120
cagcagaaac caggacaggc acccaagctc ctcatctatc ttgcatccaa cctagaatct     180
ggggtcccctt ccaggttcag tggcagtggg tctaggacag acttcaccct caccattagc    240
gcagtggagg ctgaagatgc ggcaacctat tactgtcagc aagataatga ggatccgtac     300
acgttcggag gggggaccaa gctggaaata aaa                                   333
```

<210> SEQ ID NO 35

<211> LENGTH: 111
<212> TYPE: PRT
<213> ORGANISM: Artificial Sequence
<220> FEATURE:
<223> OTHER INFORMATION: Synthesized

<400> SEQUENCE: 35

Asn Ile Val Leu Thr Gln Ser Pro Ala Ser Leu Ser Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Lys Pro Gly Gln Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ala Val Glu Ala Glu Asp Ala Ala Thr Tyr Tyr Cys Gln Gln Asp Asn
                85                  90                  95

Glu Asp Pro Tyr Thr Phe Gly Gly Gly Thr Lys Leu Glu Ile Lys
            100                 105                 110

<210> SEQ ID NO 36
<211> LENGTH: 333
<212> TYPE: DNA
<213> ORGANISM: Artificial Sequence
<220> FEATURE:
<223> OTHER INFORMATION: Synthesized

<400> SEQUENCE: 36
aacattgtgc tgacccaatc tccagcttct ttgtctgtgt ctctaggcca gagggccacc      60
atttcctgca gagccagtga agtgttgat agttatggca gaagttttat gcactggtac     120
cagcagaaac caggacaggc acccaagctc ctcatctatc ttgcatccaa cctagaatct     180
ggggtccctt ccaggttcag tggcagtggg tctaggacag acttcaccct caccattagc     240
agagtggagg ctgaagatgc ggcaacctat tactgtcagc aagataatga ggatccgtac     300
acgttcggag gggggaccaa gctggaaata aaa                                   333

<210> SEQ ID NO 37
<211> LENGTH: 111
<212> TYPE: PRT
<213> ORGANISM: Artificial Sequence
<220> FEATURE:
<223> OTHER INFORMATION: Synthesized

<400> SEQUENCE: 37

Asn Ile Val Leu Thr Gln Ser Pro Ala Ser Leu Ser Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Lys Pro Gly Gln Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Arg Val Glu Ala Glu Asp Ala Ala Thr Tyr Tyr Cys Gln Gln Asp Asn
                85                  90                  95

```
Glu Asp Pro Tyr Thr Phe Gly Gly Gly Thr Lys Leu Glu Ile Lys
            100                 105                 110
```

<210> SEQ ID NO 38
<211> LENGTH: 333
<212> TYPE: DNA
<213> ORGANISM: Artificial Sequence
<220> FEATURE:
<223> OTHER INFORMATION: Synthesized

<400> SEQUENCE: 38

```
gacatcgtga tgacccagtc tccagactcc ctggctgtgt ctctgggcga gagggccacc      60
atcaactgca gagccagtga aagtgttgat agttatggca aagtttttat gcactggtac     120
cagcagaaac ctggccaggc tcccaggctc ctcatctatc ttgcatccaa cctagaatct     180
ggggtccccc tcgaggttca gtggcagtgga tctgggacag atttcaccct caccatcaat     240
agcctggaag ctgaagatgc tgcaacgtat tactgtcagc aagataatga ggatccgtac     300
acgttcggag gggggaccaa gctggaaata aaa                                  333
```

<210> SEQ ID NO 39
<211> LENGTH: 111
<212> TYPE: PRT
<213> ORGANISM: Artificial Sequence
<220> FEATURE:
<223> OTHER INFORMATION: Synthesized

<400> SEQUENCE: 39

```
Asp Ile Val Met Thr Gln Ser Pro Asp Ser Leu Ala Val Ser Leu Gly
1               5                   10                  15
Glu Arg Ala Thr Ile Asn Cys Arg Ala Ser Glu Ser Val Asp Ser Tyr
            20                  25                  30
Gly Arg Ser Phe Met His Trp Tyr Gln Gln Lys Pro Gly Gln Ala Pro
        35                  40                  45
Arg Leu Leu Ile Tyr Leu Ala Ser Asn Leu Glu Ser Gly Val Pro Ser
    50                  55                  60
Arg Phe Ser Gly Ser Gly Ser Gly Thr Asp Phe Thr Leu Thr Ile Asn
65                  70                  75                  80
Ser Leu Glu Ala Glu Asp Ala Ala Thr Tyr Tyr Cys Gln Gln Asp Asn
                85                  90                  95
Glu Asp Pro Tyr Thr Phe Gly Gly Gly Thr Lys Leu Glu Ile Lys
            100                 105                 110
```

<210> SEQ ID NO 40
<211> LENGTH: 978
<212> TYPE: DNA
<213> ORGANISM: Homo sapiens

<400> SEQUENCE: 40

```
gcctccacca agggcccatc ggtcttcccc ctggcgccct gctccaggag cacctccgag      60
agcacagcgg ccctgggctg cctggtcaag gactacttcc ctgaaccggt gacggtgtcg     120
tggaactcag gcgctctgac cagcggcgtg cacaccttcc cggctgtcct acagtcctca     180
ggactctact ccctcagcag cgtggtgacc gtgccctcca gcaacttcgg cacccagacc     240
tacacctgca acgtagatca caagcccagc aataccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
```

-continued

```
gtggaggtgc ataatgccaa gacaaagcca cgggaggagc agttcaacag cacgttccgt    540
gtggtcagcg tcctcaccgt cgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacgc ctcccatgct ggactccgac    840
ggctccttct tcctctacag caagctcacc gtggacaaga gcaggtggca gcaggggaac    900
gtcttctcat gctccgtgat gcatgaggct ctgcacaacc actacacgca gaagagcctc    960
tccctgtctc cgggtaaa                                                    978
```

<210> SEQ ID NO 41
<211> LENGTH: 326
<212> TYPE: PRT
<213> ORGANISM: Homo sapiens

<400> SEQUENCE: 41

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

```
            275                 280                 285
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 42
<211> LENGTH: 321
<212> TYPE: DNA
<213> ORGANISM: Homo sapiens

<400> SEQUENCE: 42
ggtactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 43
<211> LENGTH: 107
<212> TYPE: PRT
<213> ORGANISM: Homo sapiens

<400> SEQUENCE: 43

Gly Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 44
<211> LENGTH: 57
<212> TYPE: DNA
<213> ORGANISM: Homo sapiens

<400> SEQUENCE: 44
atggagttgg gactgtcttg gattttcctg ttggctattc tgaaaggtgt gcagtgt         57

<210> SEQ ID NO 45
<211> LENGTH: 19
<212> TYPE: PRT
<213> ORGANISM: Homo sapiens

<400> SEQUENCE: 45

Met Glu Leu Gly Leu Ser Trp Ile Phe Leu Leu Ala Ile Leu Lys Gly
```

<210> SEQ ID NO 46
<211> LENGTH: 444
<212> TYPE: PRT
<213> ORGANISM: Artificial Sequence
<220> FEATURE:
<223> OTHER INFORMATION: Synthesized

<400> SEQUENCE: 46

```
Gln Val Gln Leu Gln Gln Ser Gly Ala Glu Leu Ala Ser Pro Gly Ala
1               5                   10                  15

Ser Val Lys Leu Ser Cys Lys Ala Ser Gly Tyr Thr Phe Thr Thr Tyr
            20                  25                  30

Trp Leu Gln Trp Val Lys Gln Arg Pro Gly Gln Gly Leu Glu Trp Ile
        35                  40                  45

Gly Ala Ile Tyr Pro Gly Pro Gly Asn Thr Lys Tyr Thr Gln Lys Phe
    50                  55                  60

Lys Asp Lys Ala Thr Leu Thr Ala Asp Lys Ser Ala Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Gly Ser Arg Arg Gly Ile Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350
```

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 47
<211> LENGTH: 444
<212> TYPE: PRT
<213> ORGANISM: Artificial Sequence
<220> FEATURE:
<223> OTHER INFORMATION: Synthesized

<400> SEQUENCE: 47

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Thr Tyr
            20                  25                  30

Trp Leu Gln Trp Val Arg Gln Ala Pro Gly Gln Gly Leu Glu Trp Met
        35                  40                  45

Gly Ala Ile Tyr Pro Gly Pro Gly Asn Thr Lys Tyr Thr Gln Lys Phe
    50                  55                  60

Lys Asp Arg Phe Thr Ile Thr Ala Asp Lys Ser Lys Ser Thr Ala Tyr
65                  70                  75                  80

Met Gln Leu Asn Ser Leu Lys Ser Glu Asp Ser Ala Val Tyr Tyr Cys
                85                  90                  95

Ala Arg Arg Gly Ser Arg Gly Ile Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270
```

-continued

```
Asn Trp Tyr Val Asp Gly Val Glu Val His Asn Ala Lys Thr Lys Pro
            275                 280                 285
Arg Glu Glu Gln Phe Asn Ser Thr Phe Arg Val Val Ser Val Leu Thr
    290                 295                 300
Val Val His Gln Asp Trp Leu Asn Gly Lys Glu Tyr Lys Cys Lys Val
305                 310                 315                 320
Ser Asn Lys Gly Leu Pro Ala Pro Ile Glu Lys Thr Ile Ser Lys Thr
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440

<210> SEQ ID NO 48
<211> LENGTH: 444
<212> TYPE: PRT
<213> ORGANISM: Artificial Sequence
<220> FEATURE:
<223> OTHER INFORMATION: Synthesized

<400> SEQUENCE: 48

Gln Val Gln Leu Val Gln Ser Gly Ala Glu Leu Val Gln Pro Gly Ala
1               5                   10                  15
Ser Val Lys Leu Ser Cys Lys Ala Ser Gly Tyr Thr Phe Thr Thr Tyr
            20                  25                  30
Trp Leu Gln Trp Val Arg Gln Thr Pro Gly Gln Gly Leu Glu Trp Met
        35                  40                  45
Gly Ala Ile Tyr Pro Gly Pro Gly Asn Thr Lys Tyr Thr Gln Lys Phe
    50                  55                  60
Lys Asp Arg Val Thr Ile Thr Ala Asp Thr Ser Thr Ser Thr Ala Tyr
65                  70                  75                  80
Met Gln Leu Asn Ser Leu Arg Ser Glu Asp Ser Ala Val Tyr Tyr Cys
                85                  90                  95
Ala Arg Arg Gly Ser Arg Arg Gly Ile Ala Tyr Trp Gly Gln Gly Thr
            100                 105                 110
Leu Val Thr Val Ser Ala Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
```

```
Asn Phe Gly Thr Gln Thr Tyr Thr Cys Asn Val Asp His Lys Pro Ser
            195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225             230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
            290                 295                 300

Val Val His Gln Asp Trp Leu Asn Gly Lys Glu Tyr Lys Cys Lys Val
305             310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 49
<211> LENGTH: 444
<212> TYPE: PRT
<213> ORGANISM: Artificial Sequence
<220> FEATURE:
<223> OTHER INFORMATION: Synthesized

<400> SEQUENCE: 49

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Thr Tyr
            20                  25                  30

Trp Leu Gln Trp Val Arg Gln Ala Pro Gly Gln Gly Leu Glu Trp Met
        35                  40                  45

Gly Ala Ile Tyr Pro Gly Pro Gly Asn Thr Lys Tyr Thr Gln Lys Phe
    50                  55                  60

Lys Asp Arg Phe Thr Ile Thr Ala Asp Thr Ser Lys Ser Thr Ala Tyr
65                  70                  75                  80

Met Gln Leu Asn Ser Leu Lys Ser Glu Asp Ser Ala Val Tyr Tyr Cys
                85                  90                  95

Ala Arg Arg Gly Ser Arg Arg Gly Ile Ala Tyr Trp Gly Gln Gly Thr
            100                 105                 110
```

Leu Val Thr Val Ser Ala Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 50
<211> LENGTH: 444
<212> TYPE: PRT
<213> ORGANISM: Artificial Sequence
<220> FEATURE:
<223> OTHER INFORMATION: Synthesized

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

```
Trp Leu Gln Trp Val Arg Gln Ala Pro Gly Gln Gly Leu Glu Trp Met
        35                  40                  45
Gly Ala Ile Tyr Pro Gly Pro Gly Asn Thr Lys Tyr Thr Gln Lys Phe
 50                  55                  60
Lys Asp Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Arg Gly Ser Arg Arg Gly Ile Ala Tyr Trp Gly Gln Gly Thr
                100                 105                 110
Leu Val Thr Val Ser Ala Ala Ser Thr Lys Gly Pro Ser Val Phe Pro
            115                 120                 125
Leu Ala Pro Cys Ser Arg Ser Thr Ser Glu Ser Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Asn Phe Gly Thr Gln Thr Tyr Thr Cys Asn Val Asp His Lys Pro Ser
        195                 200                 205
Asn Thr Lys Val Asp Lys Thr Val Glu Arg Lys Cys Cys Val Glu Cys
    210                 215                 220
Pro Pro Cys Pro Ala Pro Pro Val Ala Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Phe Arg Val Val Ser Val Leu Thr
    290                 295                 300
Val Val His Gln Asp Trp Leu Asn Gly Lys Glu Tyr Lys Cys Lys Val
305                 310                 315                 320
Ser Asn Lys Gly Leu Pro Ala Pro Ile Glu Lys Thr Ile Ser Lys Thr
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440
```

```
<210> SEQ ID NO 51
<211> LENGTH: 218
<212> TYPE: PRT
<213> ORGANISM: Artificial Sequence
<220> FEATURE:
<223> OTHER INFORMATION: Synthesized

<400> SEQUENCE: 51

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Arg Pro Gly Gln Pro Pro
        35                  40                  45

Thr Leu Leu Ile Tyr Leu Ala Ser Asn Leu Glu Ser Gly Val Pro Val
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asp Asn
                85                  90                  95

Glu Asp Pro Tyr Thr Phe Gly Gly Gly Thr Lys Leu Glu Ile Lys Gly
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 218
<212> TYPE: PRT
<213> ORGANISM: Artificial Sequence
<220> FEATURE:
<223> OTHER INFORMATION: Synthesized

<400> SEQUENCE: 52

Asn Ile Val Leu Thr Gln Ser Pro Ala Ser Leu Ser Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Arg Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Ser
65                  70                  75                  80

Ser Val Glu Ala Glu Asp Glu Ala Thr Tyr Tyr Cys Gln Gln Asp Asn
                85                  90                  95
```

```
Glu Asp Pro Tyr Thr Phe Gly Gly Thr Lys Leu Glu Ile Lys Gly
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 53
<211> LENGTH: 218
<212> TYPE: PRT
<213> ORGANISM: Artificial Sequence
<220> FEATURE:
<223> OTHER INFORMATION: Synthesized

<400> SEQUENCE: 53

```
Asn Ile Val Leu Thr Gln Ser Pro Ala Ser Leu Ser Val Ser Leu Gly
1               5                   10                  15

Gln Arg Ala Thr Ile Ser Cys Arg Ala Ser Glu Ser Val Asp Ser Tyr
            20                  25                  30

Gly Arg Ser Phe Met His Trp Tyr Gln Gln Lys Pro Gly Gln Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ala Val Glu Ala Glu Asp Ala Ala Thr Tyr Tyr Cys Gln Gln Asp Asn
                85                  90                  95

Glu Asp Pro Tyr Thr Phe Gly Gly Thr Lys Leu Glu Ile Lys Gly
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 54

<211> LENGTH: 218
<212> TYPE: PRT
<213> ORGANISM: Artificial Sequence
<220> FEATURE:
<223> OTHER INFORMATION: Synthesized

<400> SEQUENCE: 54

```
Asn Ile Val Leu Thr Gln Ser Pro Ala Ser Leu Ser Val Ser Leu Gly
1               5                   10                  15
Gln Arg Ala Thr Ile Ser Cys Arg Ala Ser Glu Ser Val Asp Ser Tyr
            20                  25                  30
Gly Arg Ser Phe Met His Trp Tyr Gln Gln Arg Pro Gly Gln Ala Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Arg Thr Asp Phe Thr Leu Thr Ile Ser
65                  70                  75                  80
Ser Val Glu Ala Glu Asp Glu Ala Thr Tyr Tyr Cys Gln Gln Asp Asn
                85                  90                  95
Glu Asp Pro Tyr Thr Phe Gly Gly Gly Thr Lys Leu Glu Ile Lys Gly
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 55
<211> LENGTH: 218
<212> TYPE: PRT
<213> ORGANISM: Artificial Sequence
<220> FEATURE:
<223> OTHER INFORMATION: Synthesized

<400> SEQUENCE: 55

```
Asn Ile Val Leu Thr Gln Ser Pro Ala Ser Leu Ser Val Ser Leu Gly
1               5                   10                  15
Gln Arg Ala Thr Ile Ser Cys Arg Ala Ser Glu Ser Val Asp Ser Tyr
            20                  25                  30
Gly Arg Ser Phe Met His Trp Tyr Gln Gln Lys Pro Gly Gln Ala Pro
        35                  40                  45
Lys Leu Leu Ile Tyr Leu Ala Ser Asn Leu Glu Ser Gly Val Pro Ser
    50                  55                  60
Arg Phe Ser Gly Ser Gly Ser Arg Thr Asp Phe Thr Leu Thr Ile Ser
65                  70                  75                  80
Arg Val Glu Ala Glu Asp Ala Ala Thr Tyr Tyr Cys Gln Gln Asp Asn
                85                  90                  95
Glu Asp Pro Tyr Thr Phe Gly Gly Gly Thr Lys Leu Glu Ile Lys Gly
```

```
                    100                 105                 110
Thr Val Ala Ala Pro Ser Val Phe Ile Phe Pro Pro Ser Asp Glu Gln
                115                 120                 125
Leu Lys Ser Gly Thr Ala Ser Val Val Cys Leu Leu Asn Asn Phe Tyr
            130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 56
<211> LENGTH: 218
<212> TYPE: PRT
<213> ORGANISM: Artificial Sequence
<220> FEATURE:
<223> OTHER INFORMATION: Synthesized

<400> SEQUENCE: 56

Asp Ile Val Met Thr Gln Ser Pro Asp Ser Leu Ala Val Ser Leu Gly
1               5                   10                  15
Glu Arg Ala Thr Ile Asn Cys Arg Ala Ser Glu Ser Val Asp Ser Tyr
            20                  25                  30
Gly Arg Ser Phe Met His Trp Tyr Gln Gln Lys Pro Gly Gln Ala Pro
        35                  40                  45
Arg Leu Leu Ile Tyr Leu Ala Ser Asn Leu Glu Ser Gly Val Pro Ser
    50                  55                  60
Arg Phe Ser Gly Ser Gly Ser Gly Thr Asp Phe Thr Leu Thr Ile Asn
65                  70                  75                  80
Ser Leu Glu Ala Glu Asp Ala Ala Thr Tyr Tyr Cys Gln Gln Asp Asn
                85                  90                  95
Glu Asp Pro Tyr Thr Phe Gly Gly Gly Thr Lys Leu Glu Ile Lys Gly
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

ANTI-HUMAN RANKL ANTIBODY, HUMANIZED ANTIBODY OF THE SAME, AND PHARMACEUTICAL COMPOSITION AND USE THEREOF

CROSS-REFERENCE TO RELATED APPLICATIONS

This application is a continuation-in-part of PCT International Application No. PCT/CN2014/095236, filed Dec. 28, 2014, claiming the priority of Chinese Patent Application No. 201310753972.3, filed Dec. 31, 2013, the contents of each of which are hereby incorporated by reference in their entirety.

REFERENCE TO A SEQUENCE LISTING

This application incorporates-by-reference nucleotide and/or amino acid sequences which are present in the file named "160803_88282_Substitute_Sequence_Listing_CAE.txt", which is 73 kilobytes in size, and which was created on Aug. 1, 2016 in the IBM-PC machine format, has an operating system compatibility with MS-Windows, and is contained in the text file filed together with this Amendment.

BACKGROUND

Human bones are a constantly changing dynamic system. After osteoclasts absorb sclerotin, osteoblasts generate sclerotin, and thus a normal bone remodeling cycle is completed. Bone remodeling rate is in a range of 2% to 10% per annum for an adult. Under normal circumstances, a dynamic balance is maintained between bone absorption and bone formation (bone metabolism), but too much sclerotin (osteosclerosis) or too little sclerotin (osteoporosis) occur after the balance between osteoclasts and osteoblasts is broken.

Differentiation signals for osteoclasts are transferred by osteoblast/mesenchymal stem cells. Signals for inducing osteoclast formation are transferred to the osteoblast/mesenchymal stem cells via various factors for stimulating bone absorption to induce the expression of osteoclast differentiation factor 1 (abbreviated as ODF-1) on the membrane thereof. ODF-1 also is known as the receptor activator of nuclear factor κB factor ligand (abbreviated as RANKL). RANKL is capable of bonding directly with the osteoclast differentiation and activation receptor (abbreviated as ODAR) on the membrane of osteoclast precursors to transfer signals to the osteoclast precursors, thereby causing cascade reactions and stimulating the differentiation, formation and maturation of the osteoclasts. ODAR also is known as the receptor activator of nuclear factor κB factor (abbreviated as, RANK). In the process of bone metabolism, the OPG/RANKL/RANK system is a key signaling pathway which plays an important modulatory role. It has been reported in the literature that some systemic metabolic bone diseases such as osteoporosis, rheumatoid disease, cancer, fracture and other diseases are healed with enhancing the bone remodeling activity, which is related closely to the RANK/RANKL/OPG system.

Many diseases occur due to bone loss caused by increasing the number of osteoclasts and (or) enhancing the activity of osteoclasts, such as postmenopausal and senile osteoporosis, cancer complicated by humoral hypercalcemia, tumor metastasis, Paget's bone disease, rheumatoid arthritis, hyperparathyroidism, and bone autolysis around the prosthesis. Since the estrogen levels are dropped after menopause, the gene expression of IL-21, IL-26, TNF-α are increased, the proliferation, differentiation, integration of the osteoclasts are promoted, the apoptosis of osteoclasts are inhibited, bone absorption is increased, bone metabolism coupling is out of balance, and thus osteoporosis occurs.

Osteoporosis diseases are treated in two main approaches as follows: (i) promoting the bone formation of osteoblasts; (ii) inhibiting the bone absorption of osteoclasts. The formation and activity of osteoclasts can be inhibited by blocking out a RANKL/RANK signaling pathway, bone absorption is blocked out, and thus the osteoporosis diseases are treated, which has been proven to be a feasible way. Prolia produced by Amgen is a fully humanized anti-human RANKL (human, RANKL, or hRANKL) monoclonal antibody obtained by immunizing transgenic mice XenoMouse™ against human IgG, which can block out the RANKL/RANK signaling pathway, effectively inhibit the formation and activity of osteoclasts, and block out bone absorption and bone destruction. Prolia was approved by US FDA to be used to treat postmenopausal osteoporosis for women in 2010. Prolia also is approved to be used to treat bone loss related to prostate cancer in Europe. The clinical effectiveness of Prolia confirms that the RANKL antibody as a monoclonal antibody drug is a new target for treating a series of bone metabolism diseases, such as bone loss due to the enhance of osteoclast's activity.

With advantages of high specificity, small side effects and obvious curative effects, the monoclonal antibody drug has become an important tool against cancer, infectious diseases, autoimmune diseases for patients. Currently, the cell fusion and hybridoma technology is still the most reliable method for preparing a monoclonal antibody, which generally is used to immunize animals such as mice, rats, sheep, rabbits. The murine is used most frequently, including rats and mice. The monoclonal antibody obtained with the method is animal-derived, and humanization modification must be performed on animal-derived monoclonal antibodies to develop the animal-derived monoclonal antibodies to be antibody drugs applied to humans, thereby reducing human anti-animal antibody (abbreviated as HAAA) responses caused by a heterologous antibody, more effectively activating the body's immune system, reducing the clearance rate of the antibody drug and extending the half-life of the antibody drug.

Antibody complementarity determining regions (abbreviated as CDRs) are regions where the antibody interacts with epitope amino acids on the antigen molecule under the support of the antibody framework regions (abbreviated as FRs). The precise molecular docking of CDRs and antigen's epitopes prepares molecular basis for the affinity and specificity of antibody, and the conformation in the natural parent antibody CDRs represents the highest affinity and the best antigen bonding specificity. Theoretically, the change of amino acids in FRs may cause the conformation in the CDRs to be changed, thereby decreasing the affinity. Studies have shown that, among all amino acids in the FRs, the humanized replacement of most of the amino acids has only a slight effect on the conformation in the CDRs, and the antibody affinity is not seriously impacted, but there are a few crucial amino acids. Once these crucial amino acids are replaced with the corresponding human amino acids, the conformation in the CDRs is changed significantly, and thus the antibody affinity is decreased seriously.

SUMMARY

The underlying technical problem of the invention is to provide an anti-human RANKL antibody, a humanized antibody for the anti-human RANKL antibody, a pharmaceutical composition and a use thereof.

In a first aspect, an anti-human RANKL antibody is provided according to the invention, and the anti-human RANKL antibody is capable of bonding specifically with an amino acid sequence of SEQ ID NO.1.

In some embodiments, the anti-human RANKL antibody comprises a heavy chain and a light chain, wherein a) the heavy chain comprises a variable region in one of amino acid sequences of SEQ ID NO.2-9, and b) the light chain comprises a variable region in one of amino acid sequences of SEQ ID NO.10-17; and the antibody bonds with RANKL to block out an interaction between RANK and RANKL.

In some embodiments, the anti-human RANKL antibody is a single-chain antibody, a humanized antibody, or murine monoclonal antibodies obtained by means of hybridoma technique.

The invention further relates to nucleic acids encoding the anti-human RANKL antibody and host cells containing the nucleic acids.

The invention further relates to method for preparing or producing the anti-human RANKL antibody, the nucleic acids, the host cells, production and the composition described in the invention.

In a second aspect, a humanized antibody for an anti-human RANKL antibody is provided according to the invention, the humanized antibody is capable of bonding specifically with human RANKL, a variable region in a heavy chain of the humanized antibody is selected from amino acid sequences of SEQ ID NO.6, NO.23, NO.25, NO.27 or NO.29, and a variable region in a light chain is selected from amino acid sequences of SEQ ID NO.14, NO.31, NO.33, NO.35, NO.37 or NO.39.

In some embodiments, a constant region in the heavy chain of the humanized antibody is selected from human IgG2, and a constant region in the light chain is selected from human Kappa; or, a constant region in the heavy chain of the humanized antibody is selected from an amino acid sequence of SEQ ID NO.41, and a constant region in the light chain is selected from an amino acid sequence of SEQ ID NO.43.

In some embodiments, the humanized antibody is an antigen bonding segment selected from scFv, (scFv)$_2$, Fab, Fab' or F(ab')2.

In some embodiments, a complete heavy chain of the humanized antibody is selected from an amino acid sequence of one of SEQ ID NO.46-50, and/or a complete light chain is selected from an amino acid sequence of one of SEQ ID NO.51-56.

In a third aspect, a pharmaceutical composition is provided according to the invention, and the active ingredients of the pharmaceutical composition include the anti-human RANKL antibody or the humanized antibody.

In a fourth aspect, a use of the anti-human RANKL antibody or the humanized antibody in preparing a medication for the treatment of bone loss diseases is provided according to the invention.

In a fifth aspect, a method for improving conditions of patients with bone loss diseases or treating patients with bone loss diseases is provided according to the invention, and the method includes giving the patients a therapeutically effective amount of the anti-human RANKL antibody, the humanized antibody or the pharmaceutical composition.

There are three forms of natural human RANKL protein in the body, including a full-length transmembrane protein, a membrane-bonding protein free of intracellular area and a soluble protein (from Gly at position 136 to Asp at position 317, a total of 182 amino acids). Studies have shown that, RANKL mainly exists on the surface of osteoblasts in a transmembrane form under physiological conditions, but under pathological conditions, RANKL in the transmembrane form are cut from the surface of osteoblasts by matrix metalloproteinase 14 (MMP14) and metalloprotease 10 (ADAM10), and a soluble RANKL protein is released, thereby resulting in significantly increased soluble RANKL in cycling, and enhancing the activity of osteoclasts. Therefore, according to the invention, the soluble RANKL protein is used as an antigen, mouse anti-human RANKL monoclonal antibodies are obtained by means of immunization mice and hybridoma fusion technology through a series of screening, and it is confirmed that these murine antibodies not only specifically bond with human RANKL, but also have a cross immune reaction with the cynomolgus monkey RANKL, but have no cross immune reaction with murine RANKL. More importantly, through experiments of competitively bonding between RANK and a respective RANKL receptor, monoclonal antibodies which can block out the RANKL/RANK bonding are obtained by the screening, and their blocking capabilities are not less than, even better than Denosumab. These antibodies can effectively inhibit the differentiation of osteoclasts induced by RANKL in vitro. Accordingly, it is believed that these monoclonal antibodies should effectively inhibit bone absorption and osteoporosis in vivo. The murine antibodies are reconstructed through human-mouse chimeric or humanized transformation, or the murine antibodies bond with an antigen and include antibody fragments having neutralizing effect, and the murine antibodies are produced by systematically culturing mammalian cells or prokaryotic cells. Hence, the murine antibodies become monoclonal antibody drugs suitable for the treatment of clinical pharmacology.

BRIEF DESCRIPTION OF THE DRAWINGS

FIG. 1 shows nucleotide sequences of constructed recombinant human RANKL (SEQ ID NO: 1).

FIG. 2 shows a curve of bonding anti-RANKL murine monoclonal antibody and human RANKL.

FIG. 3 shows a curve of bonding anti-RANKL murine monoclonal antibody and monkey RANKL.

DETAILED DESCRIPTION

Figure 4:
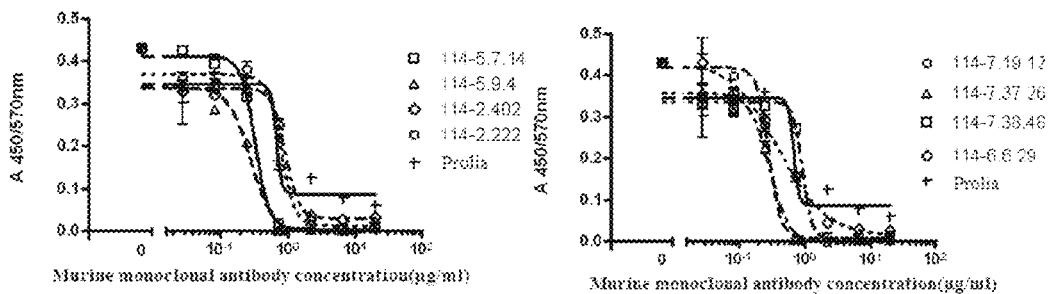
FIG. 4 shows a curve of anti-RANKL murine monoclonal antibody inhibiting the bonding between RANKL and RANK-Fc.

Unless otherwise indicated or defined otherwise, all used terms have the usual meaning in the art, the meaning should be understood by those skilled in the art. Reference is made to standard manuals, such as Sambrook et al., "Molecular Cloning: A Laboratory Manual, (2nd Edition), Vol. 1-3, Cold Spring Harbor Laboratory Press (1989); Lewin, "Genes IV", Oxford University Press, New York, (1990); and Roitt et al., "Immunology" (2nd edition), Gower Medical Publishing, London, New York (1989), as well as general prior art cited herein. In addition, unless otherwise indicated, all methods, steps, technology and operations not described in detail may be and have been carried out in a known manner, which should be understood by those skilled in the art. Reference also is made to other references cited in standard manuals and the above-mentioned general prior art.

Unless otherwise indicated, the term "immunoglobulin" and "antibody" refers to intact immunoglobulins and immunologically active fragments being capable of bonding the required antigen. The immunoglobulins and immunologically active (antigen-bonding) fragments include epitope bonding sites (i.e., antigen-specific bonding sites or epitopes which can be identified by antibodies). Examples of antibody fragments include such as Fab, F (v), Fab', F (ab')$_2$ fragments, "half molecule" derived by reducing disulfide bonds of the immunoglobulins, single-chain immunoglobulins, or other suitable antigen-bonding fragments (see e.g., Bird et al., Science, 242: 423-426 (1988); Huston et al., PMS, (USA), 85: 5879 (1988); Webber et al., Mol Immunol, 32: 249 (1995)). The antibody or immunologically active fragments may be derived from an animal (e.g., a rodent, such as a mouse or rat), or chimeric (see Morrison et al., PNAS, 81: 6851 (1984); Jones et al., Nature, 321: 522 (1986)). Furthermore, generally it should be understood that the term "sequence" (e.g., in the terms "immunoglobulin sequence", "antibody sequence", or "protein sequence" and the like) used herein include the relevant amino acid sequence, and a nucleic acid sequence or a nucleotide sequence encoding the amino acid sequence, unless a more limited interpretation is required herein.

The term (polypeptide or protein) "domain"/"region" used herein refers to a folded protein domain, which can maintain its tertiary structure independent of the rest of the protein. Generally, a domain is responsible for an individual functional property of the protein, and may be added, removed or transferred to other proteins without damaging the rest of the protein and/or the function of the domain in many cases.

The term "antibody variable domain" used herein refers to three "complementarity determining regions" or "CDRs", i.e., "complementarity determining region 1" or "CDR1", "complementarity determining region 2" or "CDR2", and "complementarity determining region 3 "or "CDR3" substantially in the art and hereinafter. Specificity of the antibody for the antigen is generated since antibody variable regions have antigen-bonding sites.

The specific bonding of an antigen-bonding protein with an antigen or epitope may be measured in any suitable known manner including, for example, the assays described herein, Scatchard Analysis and/or competitive bonding assays (such as radiation immunoassay (RIA), enzyme immunoassay (EIA) and sandwich competition analysis) and different variations known in the art.

As well known in the art, amino acid residues are indicated by the consensus standard three-letters or one-letter amino acid code. When two amino acid sequences are compared, the term "amino acid difference" refers to the insertion, deletion or substitution of a specified number of amino acids at a certain position in the reference sequence as compared to the second sequence. In a case of substitution, the substitution preferably is conservative amino acid substitution, the conservative amino acid refers to an amino acid in which an amino acid residue is substituted by another amino acid residue with a similar chemical structure, and the substitution has smaller or substantially no effect on the function, activity or other biological properties of the polypeptide. The conservative amino acid substitution is well known in the art. For example, according to WO98/49185, the conservative amino acid substitution is preferably implemented by substituting one amino acid residue in the following groups (i)-(v) with another amino acid residue in the same group. The following groups (i)-(v) include: (i) small aliphatic nonpolar or slightly polar residues: Ala, Ser, Thr, Pro and Gly; (ii) polar negatively charged residues and their (uncharged) amides: Asp, Asn, Glu and Gln; (iii) polar positively charged residues: His, Arg and Lys; (iv) large aliphatic nonpolar residues: Met, Leu, Ile, Val and Cys; and (V) aromatic residues: Phe, Tyr and Trp. Specifically preferably, the conservative amino acid substitutions include: Ala substituted with Gly or Ser; Arg substituted with Lys; Asn substituted with Gln or His; Asp substituted with Glu; Cys substituted with Ser; Gln substituted with Asn; Glu substituted with Asp; Gly substituted with Ala or Pro; His substituted with Asn or Gln; Ile substituted with Leu or Val; Leu substituted with Ile or Val; Lys substituted with Arg, Gln, or Glu; Met substituted with Leu, Tyr or Ile; Phe substituted with Met, Leu or Tyr; Ser substituted with Thr; Thr substituted with Ser; Trp substituted with Tyr; Tyr substituted with Trp or Phe; Val substituted with Ile or Leu.

Those skilled in the art can determine appropriate variants of polypeptides mentioned herein by applying the common knowledge. In some embodiments, those skilled in the art can identify a region which is not considered to be important for the activity through the guide and can change but do not destroy the appropriate parts of the active molecule. In some embodiments, conservative residues and portions of molecules among similar polypeptides may be identified. In some embodiments, conservative amino acid substitutions may also be carried out in the region important for the biological activity or the structure without destroying the biological activity or adversely affecting the polypeptide structure.

In addition, those skilled in the art can review structure function studies, identify residues in similar polypeptides which are important for activity or structure. Such comparison is considered that, one can predict the importance of amino acid residues in a protein, which is equivalent to amino acid residues in similar proteins which are important for the activity or structure. Such predicted important amino acid residues may be substituted with chemically similar amino acids for those skilled in the art.

Those skilled in the art can also analyze a three-dimensional structure and an amino acid sequence related to structures in the similar polypeptides. According to such information, those skilled in the art may predict amino acid sequences alignment in the three-dimensional structure of the antibody. In some embodiments, those skilled in the art may not change predicted amino acid residues on the surface of the protein, because such residues play a role in important interactions with other molecules. Moreover, those skilled in the art may prepare experimental variants including a single amino acid substitution on the desired amino acid residues, and then these variants may be screened by means of activity assays well known by those skilled in the art. Such variants may also be used to gather information about suitable variants. For example, if it is found that the change of a particular amino acid residue results in the destruction undesired reduced, or an unsuitable activity, such change may be avoided. In other words, based on the information obtained from such routine experiments, those skilled in the art may determine readily which substitutions should be avoided, either alone or together with other mutations.

A large number of scientific publications have been published on secondary structure prediction. See Moult J, Curr. Opin. Biotech, 7(4): 422-427 (1996), Chou et al, Biochemistry, 13 (2): 222-245 (1974); Chou et al, Biochemistry, 113 (2): 211-222 (1974); Chou et al, Adv. Enzymol. Relat. Areas Mol. Biol, 47: 45-148 (1978); Chou et al, Ann. Rev. Biochem, 47: 251-276 and Chou et al. Biophys. J, 26: 367-384 (1979). In addition, the predicting secondary structure assisted with computer programs is available currently. A method for predicting the secondary structure bases on homology simulation. For example, two polypeptides or proteins with sequences of more than 30% identity 'I' or similarity greater than 40% usually have similar structural topology. The most recent growth of Protein Structure Database (PDB) provides an enhanced predictability of secondary structures, including the number of possible folding in polypeptide or protein structures. See Holm et al., Nucl. Acid. Res, 27 (I): 244-247 (1999). It is proposed (Brenner et al, Curr. Op. Struct. Biol., 7 (3): 369-376 (1997)) that, a limited number of folding exists in the given polypeptides or proteins, and structure prediction becomes more precise suitably once the critical number of folding is determined.

Additional methods for predicting secondary structures include "threading" (Jones, D., Curr. Opin. Struct. Biol, 7 (3): 377-87 (1997); Sippl et al, Structure, 4 (I): 15-19 (1996)), "graphical analysis" (Bowie, et al., Science, 253: 164170 (1991); Gribskov, et al., Meth. Enzym, 183: 146-159 (1990); Gribskov, et al., Proc. Nat Acad. Sci, 84 (13): 4355-4358 (1987)), and the "evoluting key" (see Holm, the above mentioned (1999), and Brenner, the above mentioned (1997)).

The term "polypeptide" as a genetic term refers to native proteins, or native sequences with the deletion, addition and/or substitution of one or more amino acids. The term "polypeptide" also includes RANKL antibody or a CDR thereof (as described below, SEQ ID NO.2-9 and SEQ ID NO.10-17), or sequences with the deletion, addition and/or substitution of one or more amino acids.

A full length heavy chain includes a variable region domain VH, and three constant region domains CH1, CH2, and CH3. The domain VH is located at the amino terminus of a polypeptide, the domain CH3 is located at the carboxy terminus of a polypeptide. The term "heavy chain" used herein includes the full-length heavy chain and fragments thereof.

A full length light chain includes a variable region domain and constant region domains. Similar to the heavy chain, the variable region domain of the light chain is located at the amino terminus of a polypeptide. The term "light chain" used herein includes the full-length light chain and fragments thereof. Single chain antibodies are Fv molecules, in which the variable regions of the heavy chain and light chain are connected through flexible linkers to form a single-chain polypeptide which forms an antigen-bonding region. Single-chain antibodies are discussed in detail in WO88/01649 and U.S. Pat. Nos. 4,946,778 and 5,260,203.

In some embodiments, it is generally understood that each bonding sites are the same, for the divalent antibodies rather than "multi-specific" or "multifunctional" antibodies.

In a case that an excess amount of antibodies reduce the amount of receptor bonding with anti-receptor by at least about 20%, 40%, 60%, 80%, 85% or more (based on in-vitro competitive bonding assay), the antibody substantially inhibits adhesion between the receptor and ligands.

The term "epitope" includes any polypeptide determinant capable of specific bonding an immunoglobulin or T-cell receptor. In some embodiments, epitope determinants include chemically active surface groupings of molecules such as amino acids, sugar side chains, phosphoryl, or sulfonyl. In some embodiments, epitope determinants may have specific three-dimensional structural characteristics, and/or specific charge characteristics. Epitope is a region where the antibody bond with the antigen. In some embodiments, it is considered that the antibody specifically bonds the antigen in a case that target antigen in the complex mixture of proteins and/or macromolecules is recognized preferentially.

The term "agent" used herein refers to a compound, mixture of compounds, a biological macromolecule, or extracts prepared from biological substance.

The term "label" or "labeled" used herein refers to the insertion of a detectable label, e.g., inserting a radiolabeled amino acid or connecting biotin polypeptide detectable by labeled anti-biotin protein (e.g., streptavidin anti-biotin protein including fluorescent marker or enzymatic activity which can be detected by optical or colorimetric detection method). In some embodiments, the tags or markers may also be therapeutic. Various methods of labeling polypeptides and glycoproteins are known in the art and can be used. Examples of polypeptide tags include but are not limited to, the group of: radioisotopes or radionuclides (e.g., $^{3}H$, $^{15}N$, $^{35}S$, $^{90}Y$, $^{99}Tc$, $^{111}In$, $^{125}I$, $^{131}I$), fluorescent markers (e.g. FITC, rhodamine, lanthanide phosphors), enzymatic markers (e.g., horseradish peroxidase, galactosidase, luciferase, alkaline phosphatase), chemiluminescent agent, a biotin group, predetermined polypeptide epitopes recognized by a second report molecular (such as leucine zipper pair sequences, bonding sites for secondary antibodies, metal bonding domains, epitope tags). In some embodiments, the tags are connected by spacers of various lengths to reduce potential steric hindrance.

The term "biological sample" used herein includes but is not limited to any amount substances from a living creature or a previous living creature. Such living creature includes but is not limited to humans, mice, monkeys, rats, rabbits, and other animals. Such substances include but are not limited to blood, serum, urine, cells, tissues, organs, bone, bone marrow, lymph nodes and skin.

The term "osteopenia diseases" include but are not limited to osteoporosis, osteopenia, Paget's disease, osteolytic metastases, periodontitis, rheumatoid arthritis and bone loss due to the fixation. In addition to these bone diseases, it is known that some cancers increase the activity of osteoclasts and induce bone absorption, such as breast cancer, prostate cancer and multiple myeloma. At present, it is known that these cancers produce factors which leads to over-expression of RANKL in bone, and leads to an increase in the number and activity of osteoclasts.

The term "medicament or drugs" refers to a compound or composition which induces a desired therapeutic effect when being properly administered to the patient.

The term "modulator" refers to compounds for changing the activity or function of the molecule. For example, compared with the activity or function value under the absence of modulators, the modulators may cause the increasing or decreasing of some activity or function values. In some embodiments, the modulator is an inhibitor, which reduces at least one activity or function value of the molecule. Some exemplary activities and functions of molecules include but are not limited to bonding affinity, enzymatic activity, and signal transduction. Some exemplary inhibitors include but are not limited to, proteins, peptides, antibodies, peptibodies, carbohydrates or small organic molecules, where the peptibodies are described in, for example, WO01/83525.

The term "substantially pure" means that the subject substance exists dominantly (e.g., the subject substances are more abundant than any other various substances in the composition on a basis of a molar). In some embodiments, a substantially purified fraction is a composition in which the subject substance accounts at least about 50% (molar ratio) of all macromolecular substances. In some embodiments, a substantially pure composition includes about 80%, 85%, 90%, 95%, or more than 99% of all macromolecular substances present in the composition. In some embodiments, the subject substance is purified to be substantially homogeneous (impurities in the composition of cannot be detected by means of conventional detection methods), and the composition consists essentially of a single macromolecular substance.

The term "patient" includes human and animal subjects.

According to some embodiments of the present invention, an anti-human RANKL murine monoclonal antibodies is provided. In some embodiments, amino acid sequences especially corresponding to the variable region and nucleotide sequences encoding the amino acid sequences are provided, which includes immunoglobulins with a heavy chain and a light chain. In some embodiments, sequences corresponding to complementarity determining regions (CDR), especially from CDR1 to CDR3 are provided. According to some embodiments, hybridoma cell lines for expressing such immunoglobulin molecules and monoclonal antibodies are further provided. In some embodiments, the present invention provides a humanized antibody derived from the above-mentioned anti-human RANKL murine monoclonal antibody.

The term "humanized antibody" mainly refers to a re-expression antibody after the murine monoclonal antibody is modified by gene cloning and DNA recombinant technology, for which most of the amino acid sequences are replaced by humanized sequences, the affinity and specificity of the parent murine monoclonal antibody are retained substantially, and the heterology is reduced, advantageous for use in humans. Humanized antibodies include chimeric antibodies, modified antibodies and fully human antibodies. The basic principle of humanized is to change the specificity of antigen recognition, i.e. CDR domains, in the environment of a human immunoglobulins ("CDR grafting", Winter and Milstein). Compromise between the opposite requirements is necessary in the change from animal (usually a mouse) antibody to a humanized antibody, for which the solution is changed according to situations. In order to minimize immunogenicity, the immunoglobulin remains acceptable human sequences as more as possible. In any case, in order to maintain the original bonding properties, the immunoglobulin framework should contain a sufficient number of mutations in the acceptable human sequences to ensure that the conformation of CDR regions is similar to the conformation of CDR regions for the donor murine immunoglobulin as more as possible. Specific reference is made to Maeda et al., 1991; Singer et al., 1993; Tempest et al., 1994; Kettleborough, et al., 1991; Hsiao et al., 1994; Baca, et al., 1997; Leger et al., 1997; Ellis et al., 1995; Sato et al., 1994; Jones et al., 1986; Benhar et al., 1994; Sha and Xiang, 1994; Shearman et al., 1991; Rosok et al., 1996; Gussow & Seemann, 1991; Couto et al., 1994; Kashmiri, et al., 1995; Baker et al., 1994; Riechmann et al., 1988; Gorman et al., 1991; Verhoeyen et al., 1988; Foote & ffinter, 1992; Lewis & Crowe, 1991; Co et al., 1991; Co et al., 1991; Verhoeyen et al., 1991; Eigenbrot et al., 1994; Hamilton et al., 1997; Tempest et al., 1995; Verhoeyen et al., 1993; Cook et al., 1996; Poul et al., 1995; Co et al., 1992; Graziano et al., 1995; Presta et al., 1993; Hakimi et al., 1993; Roguska et al., 1996; Adair et al., 1994; Sato et al., 1993; Tempest et al., 1991; Sato et al., 1996; Kolbinger et al., 1993; Zhu and Carter, 1995; Sims et al., 1993; Routledge, et al., 1991; Roguska et al., 1994; Queen, et al., 1989; Carter et al., 1992; patent EP 592106; EP 1709076, et al.

Naturally Occurring Antibody Structure

Naturally occurring antibody structure typically includes a tetramer. Such tetramer typically is composed of two identical pairs of polypeptide chains, each pair having a full-length "light chain" (in some embodiments, approximately 25 kDa) and a full-length "heavy chains" (in some embodiment, approximately 50-70 kDa). Amino-terminal portion of each chain typically includes a variable region of about 100 to 110 or more amino acids, which is generally responsible for antigen recognition. Carboxy-terminal portion of each chain typically includes a constant region responsible for the function of the effector. Human light chains generally are classified as a κ light chain and a λ light chain. Heavy chains generally are classified as μ, δ, γ, α, or ε. Antibody isotypes are defined as IgM, IgD, IgG, IgA, IgE. IgG includes several subclasses, including but not limited to IgG1, IgG2, IgG3, and IgG4. IgM includes several subclasses, including but not limited to IgM1 and IgM2. Similarly, IgA is divided into several subclasses, including but not limited to IgA1 and IgA2. Generally, the variable regions and the constant regions in the full-length light chains and the full-length heavy chains are connected via "J" regions including about 12 or more amino acids, and the heavy chain also includes "D" regions including about 10 or more amino acids. Reference is made to, for example, Chapter VII of Fundamental Immunology (Paul, W. ed., Second Edition, Raven Press, NY (1989)) (for all purposes incorporated by reference). Antigen bonding sites are formed generally in the variable regions of light/heavy chains.

The variable region generally has a general structure of the same relatively conserved framework regions (FRs), via three hypervariable regions, also called complementarity determining regions or CDR regions. CDRs of the two chains are generally arranged via the framework regions, which may bond with a specific epitope. The variable regions of both light chain and heavy chain typically include structural domains FR1, CDR1, FR2, CDR2, FR3, CDR3, and FR4 from N-terminus to C-terminus. Amino acids are arranged in each domain generally based on the definition in Kabat Sequences of Proteins of Immunological Interest (Nation Institutes of Health, Bethesda, Md. (1987, 1991)), or Chothia & Lesk J. Mol. Biol. 196: 901-917 (1987); Chothia et al., Nature 342: 878-883 (1989).

Bispecific and Bifunctional Antibodies

Bispecific and bifunctional antibodies generally are artificial synthetic antibodies having two different heavy chain/light chain pairs and two different bonding sites. Various methods may be used to prepare bispecific antibodies, including but not limited to the hybridoma fusion or the connection of Fab' fragments. Reference is made to, for example, Songsivi lai & Lachmann Clin. Exp. Tmmunol. 79: 315-321 (1990), Kostelny, et al., J. Immunol. 148: 1547-1553 (1992).

Preparation of the anti-human RANKL murine monoclonal antibodies according to the present disclosure is well known for those skilled in the art. DNA sequences of the humanized antibody for the anti-human RANKL murine monoclonal antibodies are operably bonded (that is, are located in such a manner as to ensure its functionality) to expression control sequences, and then are expressed in a host cell. These vectors as expression vectors or as an integrated part of the chromosomal DNA are generally capable of be cloned in a host organism. In general, the expression vector contains selectable markers to identify cells transformed with target DNA sequences. The humanized immunoglobulin according to the invention is produced in a form of scFv recombinant or in a form of Fab, preferably in a prokaryotic system. E. coli is one of prokaryotic hosts particularly useful for cloning DNA sequences according to the invention. Moreover, there are a large number of well-characterized promoters, such as Lac or trp operons or β-lactamases or λ phages. Generally, these promoters control the expression and have ribosome bonding sites, in order to properly initiate and complete transcription and translation. The half-life period of the humanized immunoglobulin produced in the prokaryotic system according to the invention may be increased by joining the humanized immunoglobulin with polyethylene glycol (PEG). Other single-cell organisms, such as yeast, may be used for expression. The chosen host is Saccharomyces, and an appropriate carrier is used to provide sequences of expression control, replication termination and starting. Insect cell cultures may also be used to produce the humanized immunoglobulin according to the invention, typically S2 Drosophila cells transfected in a stable manner or Spodoptera frugiperda cells with a baculovirus-based expression system (Putlitz et al., 1990). Plants and plant cell cultures may be used to express the humanized immunoglobulin according to the invention (Larrick & Fry, 1991; Benvenuto, et al., 1991; Durin, et al., 1990; Hiatt et al., 1989).

According to another embodiment, the modification of extending the half-life period of the polypeptide according to the present disclosure (which also reduces the immunogenicity of the modified polypeptide) includes connecting a suitable pharmaceutically acceptable polymer, such as a linear or branched poly (ethylene glycol) (PEG) or derivatives thereof (e.g., methoxy poly (ethylene glycol) or mPEG). Generally, any suitable form of pegylation may be used, e.g., a pegylation for antibodies and antibody fragments (including but not limited to a domain antibody and scFv fragments) in the art. Reference is made to, for example, Chapman, Nat. Biotechnol, 54, 531-545 (2002); Veronese and Harris, Adv. Drug Deliv. Rev. 54, 453-456 (2003); Harris and Chess, Nat. Rev. Drug. Discov. 2 (2003); and WO2004/060965. Various reagents for pegylating polypeptide are commercially available. Preferably, fixed-point pegylation is used (particularly through cysteine residues) (see, e.g., Yang et al., Protein Engineering 16, 761-770 (2003)). For example, for this purpose, PEG may be connected to naturally occurring cysteine residues in the polypeptide according to the invention, the polypeptide according to the invention may be modified in order to properly introduce one or more cysteine residues for connecting PEG, or an amino acid sequence containing one or more cysteine residues for connecting PEG may be fused to the N-terminal and/or C-terminal of the polypeptide according to the invention. The above-described operations are achieved by using the known protein engineering technology for those skilled in the art.

According to some embodiments, the antibodies according to the invention may be used to detect RANKL in biological samples. In some embodiments, the antibodies may identify a cell or tissue for producing a protein. In some embodiments, the antibodies bonding with RANK and blocking out interaction with other bonding compounds have a therapeutic use in the regulation of osteoclasts differentiation and bone absorption. In some embodiments, the anti-human RANKL antibody may block out the bonding of RANKL and ODAR, which may lead to the blocking of signal transduction cascade and the loss of NF-κB mediated transcriptional activation. It is well known by those skilled in the art that NF-κB mediated transcription activation assay is measured by using such as a luciferase reporter.

In a first aspect, an anti-human RANKL antibody is provided according to the invention, the anti-human RANKL antibody comprises a heavy chain and a light chain, wherein a) the heavy chain comprises a variable region in one of amino acid sequences of SEQ ID NO.2-9, and b) the light chain comprises a variable region in one of amino acid sequences of SEQ ID NO.10-17; and the antibody bonds with RANKL to block out an interaction between RANK and RANKL.

In some embodiments, the anti-human RANKL antibody is a single-chain antibody, a humanized antibody, or a murine monoclonal antibody obtained by means of hybridoma technique. The humanized antibody includes chimeric antibodies, modified antibodies and fully human antibodies.

In some embodiments, the invention further relates to nucleic acids encoding the anti-human RANKL antibody and host cells containing the nucleic acids.

The invention further relates to a production or composition comprising at least the anti-human RANKL antibody according to the invention and one or more of other components of the composition.

The invention further relates to method for preparing or producing the anti-human RANKL antibody, the nucleic acids, the host cells, the production and the composition described in the invention.

In another aspect, a humanized antibody for an anti-human RANKL antibody is provided according to the invention, the humanized antibody is capable of bonding specifically with human RANKL, a variable region in a heavy chain of the humanized antibody is selected from amino acid sequences of SEQ ID NO.6, NO.23, NO.25, NO.27 or NO.29, and a variable region in a light chain of the humanized antibody is selected from amino acid sequences of SEQ ID NO.14, NO.31, NO.33, NO.35, NO.37 or NO.39.

In some embodiments, the variable region in the heavy chain is selected from amino acid sequences of SEQ ID NO.6, and the variable region in the light chain is selected from amino acid sequences of SEQ ID NO.14; or the variable region in the heavy chain is selected from amino acid sequences of SEQ ID NO.23, and the variable region in the light chain is selected from amino acid sequences of SEQ ID NO. 31; or the variable region in the heavy chain is selected from amino acid sequences of SEQ ID NO.23, and the variable region in the light chain is selected from amino acid sequences of SEQ ID NO.35; or the variable region in the heavy chain is selected from amino acid sequences of SEQ ID NO.23, and the variable region in the light chain is selected from amino acid sequences of SEQ ID NO.33; or the variable region in the heavy chain is selected from amino acid sequences of SEQ ID NO.23, and the variable region in the light chain is selected from amino acid sequences of SEQ ID NO.37; or the variable region in the heavy chain is selected from amino acid sequences of SEQ ID NO.27, and the variable region in the light chain is selected from amino acid sequences of SEQ ID NO.31; or the variable region in the heavy chain is selected from amino acid sequences of SEQ ID NO.27, and the variable region in the light chain is selected from amino acid sequences of SEQ ID NO.35; or the variable region in the heavy chain is selected from amino acid sequences of SEQ ID NO.27, and the variable region in the light chain is selected from amino acid sequences of SEQ ID NO.33; or the variable region in the heavy chain is selected from amino acid sequences of SEQ ID NO.27, and the variable region in the light chain is selected from amino acid sequences of SEQ ID NO.37; or the variable region in the heavy chain is selected from amino acid sequences of SEQ ID NO.25, and the variable region in the light chain is selected from amino acid sequences of SEQ ID NO.31; or the variable region in the heavy chain is selected from amino acid sequences of SEQ ID NO.25, and the variable region in the light chain is selected from amino acid sequences of SEQ ID NO.35; or the variable region in the heavy chain is selected from amino acid sequences of SEQ ID NO.25, and the variable region in the light chain is selected from amino acid sequences of SEQ ID NO.33; or the variable region in the heavy chain is selected from amino acid sequences of SEQ ID NO.25, and the variable region in the light chain is selected from amino acid sequences of SEQ ID NO.37; or the variable region in the heavy chain is selected from amino acid sequences of SEQ ID NO.29, and the variable region in the light chain is selected from amino acid sequences of SEQ ID NO.39; or the variable region in the heavy chain of is selected from amino acid sequences of SEQ ID NO.29, and the variable region in the light chain is selected from amino acid sequences of SEQ ID NO.31.

In some embodiments, a constant region in the heavy chain of the humanized antibody is selected from human IgG2, and a constant region in the light chain of the humanized antibody is selected from human Kappa; or, a constant region in the heavy chain of the humanized antibody is selected from an amino acid sequence of SEQ ID NO.41, and a constant region in the light chain of the humanized antibody is selected from an amino acid sequence of SEQ ID NO.43.

In some embodiments, the humanized antibody is an antigen bonding segment selected from scFv, (scFv)$_2$, Fab, Fab' or F(ab')2.

In some embodiments, a complete heavy chain of the humanized antibody is selected from an amino acid sequence of one of SEQ ID NO.46-50, and/or a complete light chain of the humanized antibody is selected from an amino acid sequence of one of SEQ ID NO.51-56.

In some embodiments, the complete heavy chain of the humanized antibody is selected from an amino acid sequence of SEQ ID NO.46, the complete light chain of the humanized antibody is selected from an amino acid sequence of SEQ ID NO.51; or, the complete heavy chain of the humanized antibody is selected from an amino acid sequence of SEQ ID NO.47, the complete light chain of the humanized antibody is selected from an amino acid sequence of SEQ ID NO.52, NO.53, NO.54 or NO.55; or, the complete heavy chain of the humanized antibody is selected from an amino acid sequence of SEQ ID NO.48, the complete light chain of the humanized antibody is selected from an amino acid sequence of SEQ ID NO.52, NO.53, NO.54 or NO.55; or, the complete heavy chain of the humanized antibody is selected from an amino acid sequence of SEQ ID NO.49, the complete light chain of the humanized antibody is selected from an amino acid sequence of SEQ ID NO.52, NO.53, NO.54 or NO.55; or, the complete heavy chain of the humanized antibody is selected from an amino acid sequence of SEQ ID NO.50, the complete light chain of the humanized antibody is selected from an amino acid sequence of SEQ ID NO.52 or NO.56.

In some embodiments, the variable region in the heavy chain is selected from an amino acid sequence of SEQ ID NO.6, the constant region in the heavy chain is selected from an amino acid sequence of SEQ ID NO.41, the variable region in the light chain is selected from an amino acid sequence of SEQ ID NO.14, and the constant region in the light chain is selected from an amino acid sequence of SEQ ID NO.43; or, the variable region in the heavy chain is selected from an amino acid sequence of SEQ ID NO.23, the constant region in the heavy chain is selected from an amino acid sequence of SEQ ID NO.41, the variable region in the light chain is selected from an amino acid sequence of SEQ ID NO.31 and the constant region in the light chain is selected from an amino acid sequence of SEQ ID NO.43; or, the variable region in the heavy chain is selected from an amino acid sequence of SEQ ID NO.23, the constant region in the heavy chain is selected from an amino acid sequence of SEQ ID NO.41, the variable region in the light chain is selected from an amino acid sequence of SEQ ID NO.35 and the constant region in the light chain is selected from an amino acid sequence of SEQ ID NO.43; or, the variable region in the heavy chain is selected from an amino acid sequence of SEQ ID NO.23, the constant region in the heavy chain is selected from an amino acid sequence of SEQ ID NO.41, the variable region in the light chain is selected from an amino acid sequence of SEQ ID NO.33 and the constant region in the light chain is selected from an amino acid sequence of SEQ ID NO.43; or, the variable region in the heavy chain is selected from an amino acid sequence of SEQ ID NO.23, the constant region in the heavy chain is selected from an amino acid sequence of SEQ ID NO.41, the variable region in the light chain is selected from an amino acid sequence of SEQ ID NO.37 and the constant region in the light chain is selected from an amino acid sequence of SEQ ID NO.43; or, the variable region in the heavy chain is selected from an amino acid sequence of SEQ ID NO.27, the constant region in the heavy chain is selected from an amino acid sequence of SEQ ID NO.41, the variable region in the light chain is selected from an amino acid sequence of SEQ ID NO.31 and the constant region in the light chain is selected from an amino acid sequence of SEQ ID NO.43; or, the variable region in the heavy chain is selected from an amino acid sequence of SEQ ID NO.27, the constant region in the heavy chain is selected from an amino acid sequence of SEQ ID NO.41, the variable region in the light chain is selected from an amino acid sequence of SEQ ID NO.35 and the constant region in the light chain is selected from an amino acid sequence of SEQ ID NO.43; or, the variable region in the heavy chain is selected from an amino acid sequence of SEQ ID NO.27, the constant region in the heavy chain is selected from an amino acid sequence of SEQ ID NO.41, the variable region in the light chain is selected from an amino acid sequence of SEQ ID NO.33 and the constant region in the light chain is selected from an amino acid sequence of SEQ ID NO.43; or, the variable region in the heavy chain is selected from an amino acid sequence of SEQ ID NO.27, the constant region in the heavy chain is selected from an amino acid sequence of SEQ ID NO.41, the variable region in the light chain is selected from an amino acid sequence of SEQ ID NO.37 and the constant region in the light chain is selected from an amino acid sequence of SEQ ID NO.43; or, the variable region in the heavy chain is selected from an amino acid sequence of SEQ ID NO.25, the constant region in the heavy chain is selected from an amino acid sequence of SEQ ID NO.41, the variable region in the light chain is selected from an amino acid sequence of SEQ ID NO.31 and the constant region in the light chain is selected from an amino acid sequence of SEQ ID NO.43; or, the variable region in the heavy chain is selected from an amino acid sequence of SEQ ID NO.25, the constant region in the heavy chain is selected from an amino acid sequence of SEQ ID NO.41, the variable region in the light chain is selected from an amino acid sequence of SEQ ID NO.35 and the constant region in the light chain is selected from an amino acid sequence of SEQ ID NO.43; or, the variable region in the heavy chain is selected from an amino acid sequence of SEQ ID NO.25, the constant region in the heavy chain is selected from an amino acid sequence of SEQ ID NO.41, the variable region in the light chain is selected from an amino acid sequence of SEQ ID NO.33 and the constant region in the light chain is selected from an amino acid sequence of SEQ ID NO.43; or, the variable region in the heavy chain is selected from an amino acid sequence of SEQ ID NO.25, the constant region in the heavy chain is selected from an amino acid sequence of SEQ ID NO.41, the variable region in the light chain is selected from an amino acid sequence of SEQ ID NO.37 and the constant region in the light chain is selected from an amino acid sequence of SEQ ID NO.43; or, the variable region in the heavy chain is selected from an amino acid sequence of SEQ ID NO.29, the constant region in the heavy chain is selected from an amino acid sequence of SEQ ID NO.41, the variable region in the light chain is selected from an amino acid sequence of SEQ ID NO.39 and the constant region in the light chain is selected from an amino acid sequence of SEQ ID NO.43; or, the variable region in the heavy chain is selected from an amino acid sequence of SEQ ID NO.29, the constant region in the heavy chain is selected from an amino acid sequence of SEQ ID NO.41, the variable region in the light chain is selected from an amino acid sequence of SEQ ID NO.31 and the constant region in the light chain is selected from an amino acid sequence of SEQ ID NO.43.

In a further aspect, a pharmaceutical composition is provided according to the invention, and the active ingredients of the pharmaceutical composition include the anti-human RANKL antibody or the humanized antibody.

The invention further relates to a use of the anti-human RANKL antibody or the humanized antibody in preparing a medication for the treatment of bone loss diseases.

In some embodiments, the bone loss diseases are selected from osteoporosis, bone destruction of bone joint due to rheumatoid arthritis, bone destruction due to osseous metastasis from tumor, bone destruction due to the growth of bone giant cell tumor and other pathological changes such as bone loss or bone destruction due to osteoclast hyperfunction induced by RANKL.

In a further aspect, a method for improving conditions of patients with bone loss diseases or treating patients with bone loss diseases is provided according to the invention, and the method includes giving the patients a therapeutically effective amount of the anti-human RANKL antibody, the humanized antibody or the pharmaceutical composition.

In some embodiments, the bone loss diseases are selected from osteoporosis, bone destruction of bone joint due to rheumatoid arthritis, bone destruction due to osseous metastasis from tumor, bone destruction due to the growth of bone giant cell tumor and other pathological changes such as bone loss or bone destruction due to osteoclast hyperfunction induced by RANKL. The above-mentioned bone diseases mainly refer to bone loss diseases.

According to some embodiments of the invention, a method for treating osteopenia diseases is provided, which includes: administering a pharmaceutically effective amount of the anti-human RANKL antibody, the humanized antibody or the pharmaceutical composition.

In some embodiments, a method for treating patients with inflammatory statuses associated with bone loss is provided, which includes: administering a pharmaceutically effective amount of the anti-human RANKL antibody, the humanized antibody or the pharmaceutical composition.

In some embodiments, a method for treating patients with autoimmune diseases associated with bone loss is provided, which includes: administering a pharmaceutically effective amount of the anti-human RANKL antibody, the humanized antibody or the pharmaceutical composition.

In some embodiments, a method for treating patients with rheumatoid arthritis associated with bone loss is provided, which includes: administering a pharmaceutically effective amount of the anti-human RANKL antibody, the humanized antibody or the pharmaceutical composition.

According to an embodiment of the invention, a method for detecting the level of human RANKL in biological samples is provided, which includes: contacting the samples with an antibody.

In some embodiments, a method of treating bone diseases is provided, which includes: administering a therapeutically effective amount of the anti-human RANKL antibody or the humanized antibody thereof. In some embodiments, a method of treating bone diseases is provided, which includes: administering a therapeutically effective amount of the anti-human RANKL antibody or the humanized antibody thereof and administering additional therapeutic agent. In such some embodiments, a therapeutically effective amount of the additional therapeutic agent is administered. In some embodiments, the bone diseases are characterized by bone loss diseases, including but not limited to osteopenia and osteolysis. In some embodiments, the use of the anti-human RANKL antibody or the humanized therapeutic antibody may inhibit a rate of bone absorption. Therefore, in some embodiments, to compensate the bone formation below the normal level, the rate of bone absorption higher than the normal rate of bone absorption is reduced or the rate of bone absorption is decreased to be below the normal level through the treatment. In some embodiments, the capability of the antibody bonding with RANKL under the absence or presence of OPG is measured, and the capability of the antibody inhibiting the production of RANKL-mediated osteoclasts and/or bone absorption may be checked.

According to some embodiments, conditions that can be treated include, but are not limited to, the group consisting of:
osteoporosis, including but not limited to, primary osteoporosis, endocrine osteoporosis (including but not limited to, hyperthyroidism, hyperparathyroidism, Cushing's syndrome, and acromegaly), genetical and autologous osteoporosis (including but not limited to, osteogenesis imperfecta, homocystinuria, Menkes syndrome, Ryan-Dai syndrome), and osteoporosis due to the extremities fixation;
bone Paget's disease for adult and juvenile (osteitis deformans);
osteomyelitis, i.e., bone infection lesions which lead to bone loss;
hypercalcemia including but not limited to hypercalcemia caused by solid tumors (including but not limited to, breast, lung and kidney) and blood malignant lesions (including but not limited to, multiple myeloma, lymphoma and leukemia), idiopathic hypercalcemia, and hypercalcemia related to hyperthyreosis and kidney dysfunction; osteopenia including but not limited to osteopenia after surgery, drug-induced osteopenia, osteopenia associated with small and large intestines, and osteopenia associated with chronic liver and kidney diseases; and bone necrosis, i.e., death of bone cells, including but not limited to bone necrosis associated with traumatic injury, bone necrosis associated with Gaucher disease, bone necrosis associated with sickle cell anemia, bone necrosis associated with systemic lupus erythematosus, bone necrosis associated with rheumatoid arthritis, bone necrosis associated with periodontal, bone necrosis associated with osteolytic metastasis, bone necrosis associated with other conditions; and cartilage loss and joint erosion associated with rheumatoid arthritis.

In some embodiments, the anti-human RANKL antibody or the humanized antibody thereof may be used alone or be used with at least one additional therapeutic agent for treating bone disease. In some embodiments, the therapeutically effective amount of another therapeutic agent is used in conjunction with the anti-human RANKL antibody or the humanized antibody thereof. Examples of therapeutic agents administered together with the anti-human RANKL antibody or humanized antibody thereof include, but are not limited to, bone morphogenic occurrence factor designated as BMP-1 to BMP BMP-12, transforming growth factor-$\beta$ (TGF-$\beta$) and TGF-$\beta$ family members; interleukin-1 (IL-1) inhibitor U, including but not limited to IL-1ra and derivatives thereof and Kineret™, anakinra; TNF-$\alpha$ inhibitors, including but not limited to, soluble TNF-$\alpha$ receptors, Enbre I™, etanercept, an anti-TNF-$\alpha$ antibody, Remicade™, infliximab, and D2E7 antibody; parathyroid hormone and analogs; parathyroid hormone-related protein and analogs; E series prostaglandins; bisphosphonate (such as alendronate and others); bone enhancing minerals such as fluoride and calcium; non-steroidal anti-inflammatory drugs (NSAIDs), including but not limited to COX-2 inhibitors such as Celebrex™, celecoxib, and Vioxx™, Luo Alexis; immunosuppressants such as methotrexate or leflunomide; serine protease inhibitors, including but not limited to, secretory leukocyte protease inhibitor (SLPI); IL-6 inhibitors (including but not limited to, anti-IL-6 antibodies), IL-8 inhibitors (including but not limited to anti-IL-8 antibodies), IL-18 inhibitors (including but not limited to IL-18 bonding protein and anti-IL-18 antibody), interleukin-1 converting enzyme (ICE) modulators; fibroblast growth factors FGF-1 to FGF-10 and FGF modulators; PAF antagonists; keratinocyte growth factor (KGF), KGF-related molecules, and KGF modulators; matrix metal protease (MMP) modulators; nitric oxide synthase (NOS) modulators, including but not limited to, inducible NOS modulators; glucocorticoid receptor modulators; glutamate receptor modulators; lipopolysaccharide (LPS) level modulators; and noradrenaline, noradrenaline modulators and analogues.

In some embodiments, the anti-human RANKL antibody or humanized antibody thereof are used with particular therapeutic agents to treat various inflammatory conditions, autoimmune conditions, or other conditions associated with bone loss. In some embodiments, two, three, or more agents may be administered depending on the conditions and the desired therapeutic levels. In some embodiments, such agents, which are contained in the same formulation, are provided. In some embodiments, such agents are provided together with the anti-human RANKL antibody or the humanized antibody thereof, which are contained in the same formulation. In some embodiments, such agents, which are contained in a kit for the treatment, are provided. In some embodiments, such agents are provided together with the anti-human RANKL antibody or the humanized antibody thereof, which are contained in a kit for the treatment. In some embodiments, such agents may be provided separately. In some embodiments, genes encoding a protein agent and/or the anti-human RANKL antibody may be included in the same vector in a case of drug administration through gene therapy. In some embodiments, the genes encoding a protein agent and/or the anti-human RANKL antibody may be controlled by the same promoter region. In some embodiments, the genes encoding a protein agent and/or the anti-human RANKL antibody may be carried in separate vectors.

In some embodiments, the present disclosure relates to a therapeutic plan including the anti-human RANKL antibody or the humanized antibody thereof and at least one interleukin-1 (IL-1) inhibitors, and a therapeutic method applying the therapeutic plan. In some embodiments, the therapeutic plan includes the anti-human RANKL antibody or the humanized antibody thereof, an IL-1 inhibitor and at least one additional molecule described herein. In some embodiments, the therapeutic method includes using the anti-human RANKL antibody or the humanized antibody thereof in combination with an IL-1 inhibitor and/or a TNF-α inhibitor. In some embodiments, the anti-human RANKL antibody or the humanized antibody thereof and the IL-1 inhibitor and/or the TNF-α inhibitor may be used together in the treatment of asthma, rheumatoid arthritis and multiple sclerosis.

Interleukin-1 (IL-1) is an anti-inflammatory cytokines. In some instances, IL-1 is a mediator in a lot of diseases and medical conditions. In some instances, macrophage cells/single-cell line cells produce IL-1. In some instances, IL-1 is produced in two forms of IL-1a and IL-1β.

If a spontaneous or experimental disease or medical condition is related to an increased level of IL-1 in body fluids or tissues, or, if the cells or tissue from the body produce an increased level of IL-1 in cultures, it is considered that the disease or medical condition is an "interleukin-1 mediated disease". In some embodiments, such interleukin-1 mediated disease may be identified through the following additional two conditions: (I) the pathologic finding associated with the disease or medical condition is simulated with an animal in experiments by administering IL-1 or up-regulating the expression of IL-1; and (II) the pathology induced in the experimental animal model for the disease or medical condition may be inhibited or eliminated via the treatment with an agent that inhibits IL-1 effect. In some embodiments, one or more of the above-described conditions are consistent with IL-1-mediated diseases. In some embodiments, all three conditions are consistent with IL-1-mediated diseases. Acute and chronic interleukin-1 (IL-1)-mediated diseases include, but are not limited to the group of: acute pancreatitis; amyotrophic lateral sclerosis (ALS, or Lou Gehrig's disease); Alzheimer's disease; cachexia/anorexia, including but not limited to, AIDS-induced cachexia; asthma and other lung diseases; atherosclerosis; autoimmune vasculitis; chronic fatigue syndrome; *clostridium*-related diseases, including but not limited to, *clostridium*-related diarrhea; coronary conditions and indications, including but not limited to, congestive heart failure, coronary restenosis, myocardial infarction, myocardial dysfunction (for example, sepsis-related), and coronary artery bypass graft; cancers, including but not limited to leukemia which includes but not limited to multiple myeloma and myeloid leukemia (such as AML and CML), and tumor metastasis; diabetes (including but not limited to, insulin-dependent diabetes); endometriosis; fever; fibromyalgia tumor; glomerulonephritis; graft versus host disease and/or graft rejection; hemorrhagic shock; hyperalgesia; inflammatory bowel disease; arthritis conditions, including but not limited to, osteoarthritis, psoriatic arthritis and rheumatoid arthritis; inflammatory eye disease, including but not limited to, such as those related to corneal transplant; ischemia, including but not limited to the brain ischemia (including but not limited to brain damage due to such as trauma, epilepsy, hemorrhage or stroke, each of which may lead to neurodegeneration); Kawasaki's disease; learning disabilities; pulmonary disease (including but not limited to, acute respiratory distress syndrome, or ARDS); multiple sclerosis; myopathy (eg, muscle protein metabolism, including but not limited to, muscle protein metabolism in sepsis); neurotoxicity (including but not limited to, neurotoxicity induced by HIV); osteoporosis; pains, including but not limited to pain associated with cancer; Parkinson's disease; periodontal disease; premature birth; psoriasis; reperfusion injury; septic shock; radiation therapy side effects; temporomandibular joint disease; sleep disorders; uveitis; inflammations caused by the strain, sprain, cartilage damage, trauma, orthopedic surgery, infection or other disease processes.

In some embodiments, the present disclosure relates to a therapeutic plan including the anti-human RANKL antibody or humanized antibody thereof and at least one TNF-α inhibitor, and a therapeutic method applying the therapeutic plan. In some embodiments, the therapeutic plan includes the anti-human RANKL antibody or humanized antibody thereof, a TNF-α inhibitor and at least one additional molecule described herein. A number of diseases and medical conditions are mediated by TNF-α and are categorized as inflammatory conditions. "TNF-α mediated disease" used herein includes but is not limited to diseases or medical conditions associated with an increased level of IL-1 in body fluids or tissues or diseases or medical conditions in which the cells or tissue from the body produce an increased level of IL-1 in cultures. In some embodiments, if (I) the pathologic finding associated with the disease or medical condition is simulated with an animal in experiments by administering IL-1 or up-regulating the expression of IL-1; and/or (II) the pathology induced in the experimental animal model for the disease or medical condition may be inhibited or eliminated via the treatment with an agent that inhibits IL-1 effect, it is considered that the disease is an "interleukin-1 mediated disease". A number of diseases and medical conditions are mediated by TNF-α and are categorized as inflammatory conditions. "TNF-α mediated diseases" used herein include but are not limited to: cachexia and anorexia; cancer, including but not limited to, leukemia; chronic fatigue syndrome; coronary conditions and/or indications, including but not limited to, congestive heart failure, coronary restenosis, myocardial infarction, myocardial dysfunction (including but not limited to such situation associated with sepsis), and coronary artery bypass graft; depression; diabetes, including but not limited to, juvenile onset Type I diabetes, diabetes, and insulin resistance (including but not limited to, obesity-related insulin resistance); endometriosis, endometritis and related conditions; fibroid and analgesia; graft host rejection; hyperalgesia; inflammatory bowel diseases, including but not limited to Crohn's disease and *Clostridium difficile*-related diarrhea; ischemia, including but not limited to brain damage due to such as trauma, epilepsy, hemorrhage, and/or stroke, brain injury results; pulmonary disease, including but not limited to, adult respiratory distress syndrome, asthma, pulmonary fibrosis; multiple sclerosis; neuroinflammatory diseases; ocular diseases and conditions, including but not limited to, corneal transplant, ocular degeneration and uveitis; pains, including but not limited to, pains associated with cancer; pancreatitis, periodontal disease; *pityriasis rubra* pilaris (PRP); prostatitis, including bacterial and non-bacterial prostatitis, and related conditions; psoriasis and related conditions; pulmonary fibrosis; reperfusion injury; Rheumatism, including but not limited to, rheumatoid arthritis, osteoarthritis, juvenile arthritis (including but not limited to juvenile rheumatoid arthritis), seronegative polyarthritis, ankylosing spondylitis, Reiter's syndrome and reactive arthritis, Still's disease, psoriatic arthritis, bowel disease arthritis, polymyositis, dermatomyositis, scleroderma, systemic sclerosis, vasculitis (such as Kawasaki's disease), brain vasculitis, raismes disease, *Staphylococcus aureus*-induced ("septic") arthritis, Sjogren's syndrome, rheumatic fever, polychondritis, polymyalgia rheumatica, and giant cell arteritis myopathy);

septic shock; radiotherapy side effects; systemic lupus erythematosus (SLE); temporomandibular joint disease; thyroiditis; and tissue transplantation and/or inflammations caused by such as strain, sprain, cartilage damage, trauma, orthopedic surgery, infections (such as HIV, *Clostridium difficile* and associated species) or other disease processes.

In some embodiments, TNF-α inhibitors are produced by down-regulating or inhibiting TNF-α. TNF-α inhibitors bond with free THF, interfere the bonding of TNF-α and its receptor, and interfere at least one factor in the signal transmission regulation after TNF-α bonds with its receptor. The term "TNF-α inhibitor" includes, but is not limited to, a soluble TNF-α receptor including but not limited to, soluble tumor necrosis factor receptor type I (Stnf-α-RI; also known as p55 receptor), soluble tumor necrosis factor receptor type II (also known as p75 receptor), and Enbrel™, etanercept; anti-TNF-α antibody, including but not limited to, Remicade™, infliximab and D2E7 (see, for example, U.S. Pat. Nos. 6,090,382 and 6,258,562); anti-TNF-α receptor antibodies; sTNF-α-RI (see, for example, WO98/24463), Etanercept (Enbrel™); TNF-α converting enzyme (TACE) inhibitors; and other molecules affecting the activity of TNF-α.

In some embodiments, the anti-human RANKL antibody or humanized antibody thereof may be administered in conjunction with at least one therapeutic agent for inflammation. In some embodiments, the anti-human RANKL antibody or humanized antibody thereof may be administered in conjunction with at least one therapeutic agent for immune diseases. Exemplary therapeutic agents for inflammation and immune disorders include, but are not limited to, corticosteroids, including but not limited to, prednisolone; non-aromatic anti-inflammatory drugs left (NSAIDs), including but not limited to, cyclooxygenase type I (COX-1) inhibitors and cyclooxygenase type 2 (COX-2) inhibitors; disease modifying anti-rheumatic drugs (DMARDs), including but not limited to, methotrexate, hydroxy chloroquine, chloroquine, cyclosporin, gold compounds (for example, sulfur vinegar Portuguese gold, gold sulfur succinate salt, and glucose sulfur gold), leflunomide; IV phosphodiesterase inhibitors, including but not limited to, rolipram and pentoxifylline base; tacrolimus (FK-506); sirolimus (rapamycin); mycophenolic acid; 5-lipoxygenase inhibitors, including but not limited to, zileuton; interleukin-6 (IL-6) modulators; a small molecule modulator for 38 kDa mitogen-activated protein kinase (P38-MAPK); small molecule modulators for intracellular molecules involved in inflammatory pathways, wherein such intracellular molecules include, but are not limited to, Jnk, IKK, NF-κB, ZAP70, and Lck. Some exemplary therapeutic agents for inflammation are described in, for example, C A Dinarello and L L Moldawer Proinflammatory and Ant1-Inflammatory Cytokines in Rheumatoid Arthritis: A Primer for Clinicians, third edition (2001) Amgen Inc., Thousand Oaks, Calif. Exemplary therapeutic agents for inflammation and autoimmune diseases include but not limited to, interferon-γ (IFN-γ) modulators; OX40/OX40L modulators (including OX40 of soluble forms); 4-1 BB/4-1 BB ligand modulators (including 4-1 BB of soluble forms); modulators in B cells and T cells co-stimulation pathways.

In some embodiments, the anti-human RANKL antibody or humanized antibodies may be used to treat bone loss which include but not limited to, bone loss caused by osteolytic damage due to malignant or metastatic tumors. In some embodiments, the anti-human RANKL antibody or humanized antibody thereof may be used to treat bone loss associated with cancer. Exemplary cancers include, but are not limited to breast cancer, prostate cancer, thyroid cancer, renal cancer, lung cancer, esophageal cancer, colorectal cancer, bladder cancer, cervical cancer, ovarian cancer and liver cancer, and gastrointestinal cancer. In some embodiments, the anti-human RANKL antibody or humanized antibody thereof may be used to treat bone loss associated with some bad blood diseases, including but not limited to, multiple myeloma and lymphoma, including Hodgkin's disease.

In some embodiments, the anti-human RANKL antibody or the humanized antibody thereof may be administered separately. In some embodiments, the anti-human RANKL antibody or the humanized antibody thereof may be administered together with at least one other therapeutic agent, including but not limited to, at least one other cancer therapeutic agent. Exemplary cancer therapy agents include, but are not limited to radiotherapy and chemotherapy. In some embodiments, chemotherapy may be a treatment using one or more of the following drugs: anthracyclines, taxol, tamoxifen, doxorubicin, 5-fluorouracil, and other drugs known in the art. In some embodiments, the cancer therapeutic agent is a luteinizing hormone releasing hormone (LHRH) antagonist.

The Pharmaceutical Composition

In some embodiments, the present disclosure provides a pharmaceutical composition comprising a therapeutically effective amount of an anti-human RANKL antibody or a humanized antibody thereof and pharmaceutically acceptable diluent, carrier, solubilizer, emulsifier, preservative and/or adjuvant.

In some embodiments, the present disclosure provides a pharmaceutical composition comprising a therapeutically effective amount of an anti-human RANKL antibody or a humanized antibody thereof, a therapeutically effective amount of at least one additional therapeutic agent, and pharmaceutically acceptable diluent, carrier, solubilizer, emulsifier, preservative and/or adjuvant. In some embodiments, the at least one additional therapeutic agent is selected from: a bone morphogenic factor, a transforming growth factor-β (TGF-β), interleukin-1 (IL-1) inhibitors including but not limited to IL-1 ra and its derivatives and Kineret™, anakinra; TNF-α inhibitors including but not limited to, a soluble TNF-α receptor, Enbrel™, etanercept, an anti-TNF-α antibody, Remicade™, infliximab, and D2E7 antibody; thyroid parathyroid hormone and analogs; parathyroid hormone-related protein and analogs; E series prostaglandins; bisphosphonates (such as alendronate and others); bone enhancing minerals such as fluoride and calcium; non-steroidal anti-inflammatory drugs (NSAIDs), including but not limited to COX-2 inhibitors such as Celebrex™, celecoxib and Vioxx™, Luo Alexis; immunosuppressants such as methotrexate or leflunomide; serine protease inhibitors, including but not limited to, secretory leukocyte protease inhibitor (SLPI); IL-6 inhibitors (including but not limited to anti-IL-6 antibodies), IL-8 inhibitors (including but not limited to anti-IL-8 antibodies), IL-18 inhibitors (including but not limited to IL-18 bonding proteins and anti-IL-18 antibody), interleukin-1 converting enzyme (ICE) modulators; fibroblast growth factor FGF-1 to FGF-10 and FGF modulators; PAF antagonist; keratinocyte growth factor (KGF), KGF-related molecules, and KGF modulators; matrix metalloproteinase (MMP) modulators; nitric oxide synthase (NOS) modulators, including but not limited to, inducible NOS modulators; glucocorticoid receptor modulators; glutamate receptor modulators; lipopolysaccharide (LPS) level modulators; and noradrenaline and noradrenaline modulators and analogues.

In some embodiments, acceptable formulation substances are preferably used in dose and concentration being not toxic to the recipient. In some embodiments, the pharmaceutical composition may contain formulation substances for changing, maintaining or retaining such as pH, osmolarity, viscosity, clarity, color, isotonicity, odor, sterility, stability, rate of dissolution or release, absorption or penetration of the composition. In some embodiments, the suitable formulation substances include, but are not limited to, amino acids (such as glycine, glutamine, asparagine, arginine or lysine); antimicrobials; antioxidants (e.g. ascorbic acid, sodium sulfite or sodium bisulfate); buffers (e.g. borate, bicarbonate, Tris-HCl, citrates, phosphates or other organic acids); fillers (e.g., mannitol or glycine); chelating agents (e.g., ethylene tetraacetic acid (EDTA)); complexing agents (such as caffeine, polyvinylpyrrolidone, cyclodextrin or hydroxypropyl cyclodextrin); filler; monosaccharides, disaccharides and other carbohydrates (e.g., glucose, mannose or dextrins); proteins (e.g., serum albumin, gelatin, or immunoglobulins); coloring agents, flavoring agents and diluents; emulsifying agents; hydrophilic polymer (e.g., polyvinylpyrrolidone); low molecular weight of polypeptides; salt-forming counterions (such as sodium); preservatives (e.g., benzalkonium chloride, benzoic acid, salicylic acid, thimerosal, phenethyl alcohol, methylparaben, propylparaben, chlorhexidine, sorbic acid or too hydrogen peroxide); solvents (e.g. glycerol, propylene glycol or polyethylene glycol); sugar alcohols (e.g. mannitol or sorbitol); suspending agents; surfactants or wetting agents (e.g., pluronics, PEG; sorbitan sugar esters, polysorbates, such as polysorbate20, polysorbate80, lecithin, cholesterol, tyloxapol), stability enhancing agents (such as sucrose or sorbitol); tonicity enhancing agents (e.g., alkali metal halides, preferably sodium chloride or chlorine potassium, mannitol, sorbitol); delivery excipients; diluents; excipients and/or pharmaceutical adjuvants (Remington's Pharmaceutical Science, Edition 18, AR Gennaro ed., Mack Publish Company (1990)).

In some embodiments, the anti-human RANKL antibody or humanized antibody thereof and/or therapeutic molecules are connected to a half-life period extending excipient which is well known in the art. Such excipients include but are not limited to, polyethylene glycol and dextran. Such excipients are described in, for example, U.S. application registration Ser. No. 09/428,082 and a published PCT application No. WO99/25044, which are incorporated by reference for any purpose herein.

In some embodiments, those skilled in the art may determine an optimal pharmaceutical composition according to, for example, the desired route of administration, delivery methods and desired dose. For example, reference is made to Remington's Pharmaceutical Science, Edition 18th, AR Gennaro et al., Mack Publish Company (1990). In some embodiments, such compositions may influence the physical state, stability, rate of release in vivo, and rate of clearance in vivo of the antibody according to the present disclosure.

In some embodiments, the properties of main excipients or carriers in the pharmaceutical composition may be aqueous or non-aqueous. For example, in some embodiments, a suitable excipient or carrier may be water for injection, physiological saline or artificial cerebrospinal fluid, possibly including other substances commonly used for parenteral administration compositions. In some embodiments, neutral buffered saline or saline mixed with serum albumin are other examples of the excipients. In some embodiments, the pharmaceutical composition contains Tris buffer of about pH7.0-8.5 or acetate buffer of about pH4.0-5.5, and the pharmaceutical composition may further contain sorbitol or suitable substitutes. In some embodiments, the composition containing the anti-human RANKL antibody or humanized antibody thereof, with or without at least one additional therapeutic agent may be prepared by mixing the selected composition of a desired purity with any one optional formulation reagent. Furthermore, in some embodiments, the composition containing the anti-human RANKL antibody or humanized antibody thereof, with or without at least one additional therapeutic agent may be made into lyophilizer by using appropriate excipients such as sucrose.

In some embodiments, the pharmaceutical compositions according to the present disclosure may be used for parenteral administration. In some embodiments, the pharmaceutical compositions may be used for inhalation or through the digestive tract, such as oral delivery. The preparation of such pharmaceutically acceptable compositions is known in the art.

In some embodiments, in a case of parenteral administration, the therapeutic composition may be a pharmaceutically acceptable excipient pyrogen-free, parenterally acceptable, and contain the desired anti-human RANKL antibody or a humanized antibody thereof, with or without additional therapeutic agent in a form of an aqueous solution. In some embodiments, excipients for parenteral injection is sterile distilled water, with which the anti-human RANKL antibody or the humanized antibody thereof, with or without at least one additional therapeutic agent, are formulated as a sterile isotonic solution, and are properly preserved. In some embodiments, the desired molecules and reagents are involved in the preparation, such as injectable microspheres, bio-degradable particles, polymeric compounds (such as polylactic acid or polyglycolic acid), beads or liposomes, which may allow the production to be controlled or sustained released, and then be delivered through the extension-acting injection. In some embodiments, hyaluronic acid may also be used, which can play a role of promoting and keeping in the circulation. In some embodiments, an implantable drug delivery device may be used to introduce the desired molecule.

In some embodiments, the pharmaceutical composition may be formulated into formulations for inhalation. In some embodiments, the anti-human RANKL antibody or the humanized antibody thereof, with or without at least one additional therapeutic agent, may be formulated as a dry powder for inhalation. In some embodiments, an inhalation solution comprising the anti-human RANKL antibody or the humanized antibody thereof, with or without at least one additional therapeutic agent, may be formulated by using propellant used for aerosol delivery. In some embodiments, the solution may be sprayed. Pulmonary administration is described in PCT Application NO. PCT/US94/001875, in which the pulmonary delivery of chemically modified proteins is described.

In some embodiments, formulations for oral administration are related. In some embodiments, those carriers conventionally used in solid dosage forms such as tablets and capsules may be used or not, and the anti-human RANKL antibody or the humanized antibody thereof, with or without at least one additional therapeutic agent, may be formulated in such way. In some embodiments, a capsule for an active moiety of a point release formulation in the digestive tract may be designed, considering maximum bioavailability and minimum pre-systemic degradation. In some embodiments, at least one additional reagent may be contained to facilitate the absorption of the anti-human RANKL antibody or a humanized antibody thereof and/or any additional therapeutic agent. In some embodiments, diluents, flavoring agents, low melting waxes, vegetable oils, lubricants, suspending agents, tablet disintegrating agents, and bonders may also be used.

In some embodiments, the pharmaceutical composition may contain an effective amount of the anti-human RANKL antibody or a humanized antibody thereof, with or without at least one additional therapeutic agent in a mixture of non-toxic excipients suitable for the preparation of tablets. In some embodiments, a solution in a single dosage form may be prepared by dissolving the tablets in sterile water, or other suitable excipients. In some embodiments, the suitable excipients include, but are not limited to, inert diluents, such as calcium carbonate, sodium carbonate or bicarbonate, lactose, or calcium phosphate; or bonders, such as starch, gelatin, or acacia; or a lubricant such as magnesium stearate, stearic acid or talc.

Another pharmaceutical composition is apparent for those skilled in the art, which includes the anti-human RANKL antibody or a humanized antibody thereof, with or without at least one additional therapeutic agent, in a sustained or controlled release delivery formulation. In some embodiments, a variety of formulation techniques in other sustained or controlled release delivery mode, such as liposome carriers, biodegradable microparticles or porous beads and extended-acting injection, are well known by those skilled in the art. Reference is made to, for example, PCT Application No. PCT/US93/00829, in which the controlled release of porous polymer microparticles for delivery pharmaceutical composition is described. In some embodiments, sustained release formulations may include semipermeable polymer matrices in the form of a tangible product, such as films, or microcapsules. Sustained-release matrix may include polyesters, hydrogels, polylactide (U.S. Pat. No. 3,773,919 and EP058481), L-glutamate and γ-ethyl-L-glutamic acid copolymer (Sidman et al., Biopolymers, 22: 547-556 (1983)), poly (2-ethyl-light-methacrylate) (Langer et al., J. Biomed. Mater. Res. 15: 167-277 (1981) and Langer, Chem. Tech, 12: 98-105 (1982)), ethylene vinyl acetate (Langer et al., the above-described) or poly-D(-)-3-hydroxybutyric acid (EP133988). In some embodiments, sustained release compositions may further include liposomes prepared by several methods, which are well known in the art. Reference is made to, for example, Eppstein et al., Proc. Natl. Acad. Scl. USA, 82: 3688-3692 (1985); EP036676; EP088046 and EP143949.

Generally, in-vivo administrated pharmaceutical composition is sterile. In some embodiments, the in-vivo administrated pharmaceutical composition may be filtered through a sterile membrane filtration. In some embodiments, in the case that the composition is lyophilized, the composition may be sterilized using this method before or after the lyophilization and reconfiguration of the composition. In some embodiments, parenteral administered compositions may be stored in lyophilized form or in a solution form. In some embodiments, the parenteral compositions generally is stored in a container having a sterilization opening, for example, intravenous fluid bags or vials having a cover perforated by hypodermic needles.

In some embodiments, once a pharmaceutical composition is formulated, the pharmaceutical composition may be stored as a solution, suspension, gel, emulsion, or solid in a sterile vial, or be stored as dehydrated or lyophilized powders in sterile vials. In some embodiments, such formulations may be stored in a ready-to-use form or in a reconstitution before administration form (e.g., lyophilized).

In some embodiments, the present disclosure relates to the preparation of kits in single-dose administration unit. In some embodiments, the kit may include a first container filled with dried proteins and a second container filled with an aqueous formulation. According to some embodiments of the present disclosure, kits comprising pre-filled syringes with a single chamber or multiple chambers (e.g., liquid syringes and dissolved syringe) are provided.

In some embodiments, a therapeutically effective amount of pharmaceutical composition which includes the anti-human RANKL antibody or the humanized antibody thereof, with or without at least one additional therapeutic agent, depends on the treatment and the subject. It can be understood by those skilled in the art that, according to some embodiments, appropriate dosage levels are different partially depending on the delivered molecule, indications of anti-human RANKL antibody or a humanized antibody thereof (with or without at least one additional therapeutic agent), a route of administration and patient's size (body weight, body surface area or organ size) and/or conditions (the age and general health status). In some embodiments, the physician may adjust the dose and change the route of administration to obtain the optimal therapeutic effect. In some embodiments, considering the above-mentioned factors, the general dose may be in a range from about 0.1 μg/kg to about 100 mg/kg or more. In some embodiments, the dose may be a range from 0.1 μg/kg to about 100 mg/kg; the dose may be a range from 1 μg/kg to about 100 mg/kg; or the dose may be a range from 5 μg/kg to about 100 mg/kg.

In some embodiments, pharmacokinetic parameters of the anti-human RANKL antibody or humanized antibody thereof and/or any additional therapeutic agent in the formulation should be taken into account, to determine the frequency of administration. In some embodiments, the physician administers the composition in a dose until the desired effect is achieved. In some embodiments, the pharmaceutical compositions according to the present disclosure may be administered in a single dose, or two or more doses over time (which may or may not contain the same amount of the desired molecule), or a continuous infusion by using an implantation device or catheter. Those skilled in the art routinely determine the exact right dose, which are their usual routine tasks. In some embodiments, the appropriate dose may be determined through the application of appropriate dose-response data.

In some embodiments, the route of administration for the pharmaceutical compositions are well-known, e.g., oral, intravenous, intraperitoneal, intracerebral (intraparenchymal), intracerebroventricular, intramuscular, intraocular, intraarterial, liver door or a route of in-lesions; or by means of sustained release systems or implantation devices. In some embodiments, the composition may be administered by bolus injection or continuous infusion, or by means of an implantation device.

In some embodiments, the composition may be administered locally by implanting membrane, sponge or other suitable substances on which the desired molecules are attached or by which the desired molecules are encapsulated. In some embodiments, an implantation device may be implanted in any suitable tissue or organ in a case that the implantation device is used, and the desired molecules can be delivered by diffusion, release bolus with time, or continuous administration.

In some embodiments, it is desirable to use in vitro the pharmaceutical composition comprising the anti-human RANKL antibody or humanized antibody thereof, with or without at least one additional therapeutic agent. In this case, cells, tissues and/or organs taken from the patient contact the pharmaceutical composition comprising the anti-human RANKL antibody or humanized antibody thereof, with or without at least one additional therapeutic agent, and then the cells, tissues and/or organs are transplanted back to the patient.

In some embodiments, the anti-human RANKL antibody or humanized antibody thereof, and/or any additional therapeutic agent may be delivered by implanting the genetically engineered cells with the method described herein to express and secrete polypeptides. In some embodiments, such cells may be animal cells or human cells, and may be autologous, allogeneic, or xenogeneic. In some embodiments, the cells may be immortalized. In some embodiments, the cells may be encapsulated to avoid the infiltration of surrounding tissue, on order to reduce immune response opportunities. In some embodiments, the encapsulating substances typically include biocompatible semipermeable polymer shell or membrane, which allows protein products to be released, but prevent patient's immune system or harmful factors from surrounding tissues from damaging cells.

The invention is further set forth with specific examples below. These examples are intended to illustrate the present disclosure and not intended to limit the scope of the invention. The specific conditions for experimental methods are not indicated in the following examples, and the experimental methods are carried out generally in accordance with the conventional conditions or in accordance with conditions recommended by the manufacturer. Unless otherwise defined, all professional and scientific terminology used herein have the same meanings as known by those skilled in the art. In addition, any methods and substances similar or equal to the recorded content are applicable to the invention. The preferred embodiment and substances described herein are only for demonstration purposes.

Example 1 The Preparation of a Human RANKL

An expression vector for the human RANKL is built, CHO cells are transfected stably, and then cell lines capable of stably high expressing the human RANKL are screened. The cell line is cultivated in a large scale, cell supernatants is collected, and the human RANKL protein is purified by a nickel column to prepare the human RANKL protein, which is used to mice immunization, clone screening and identification in Examples 2, 3, 4, 5, 6, and 7.

CHO cells are purchased from Invitrogen, RAW264.7 cells are purchased from Cell Bank of Shanghai Institute, expression vectors are provided by our company, T4 DNA ligase, protein molecular weight standard Marker, and restriction enzymes are purchased from NEB; gel extraction kits are purchased from Invitrogen; 302 medium, trypsin and FBS are purchased from Invitrogen; Phenyl sepharose 6 FF-low sub, SP-Sepharose FF, Ni-NTA Sepharose FF gel are purchased from GE; disodium hydrogen phosphate, dihydrogen phosphate sodium, sodium chloride, Tris, citric acid, trisodium citrate, imidazole and MTX are purchased from Sigma, goat anti-human IgG-HRP are purchased from Jackson, TMB Substrates are purchased from Cell Signaling Technology, RANK-Fc, TRANC, M-CSF and TGF-β are purchased from R & D Systems, TRAP color system is purchased from Sigma, DMEM medium, α-MEM medium and fetal bovine serum are purchased from Invitrogen.

PCR instrument (Hangzhou Michelangelo Scientific Instruments Biology Co., Ltd.), shaker CLIMO-SHAKER 1SFS-X (Switzerland Kuhner). Multifunctional microplate reader is Molecular Devices SpectraMax M5 Multi-mode Microplate Reader, Washer is TECAN HydroFlex Plate Washer, Super Clean Bench belongs to a brand of Sujing with specifications SW-CJ-2F/T, carbon dioxide incubator belongs to a brand of Thermo with specifications Forma 311.

(1) Construction of Expression Vector for Human RANKL

Firstly, human RANKL target sequence (FIG. 1) is synthesized by means of genetic engineering, the target sequence includes 182 amino acids (SEQ ID NO.1) from Gly at position 136 to Asp at position 317 of a natural human RANKL, 10 His are added in the N-terminal, which may bond with nickel chloride in the nickel column, and thus the human RANKL target sequence may be purified by ion affinity chromatography, and both NotI and PmeI restriction sites are added at both ends. The synthetic human RANKL and expression vectors are cut out by the two enzymes NotI and PmeI, human RANKL target fragments and expression vector fragments are recovered, connected, and transformed, positive clones are identified by PCR and enzyme digestion, and finally the correctness of expression vector is verified through sequencing. The plasmids are extracted using a plasmid extraction kit for stable transfection.

(2) Stable Transfection of CHO Cells and Colony Screening

During 48 hours before transfection, CHO cells are sub-cultured in 302 serum-free medium, with a seeding density of $3\times10^5$/ml. On the day of transfection, the total number of cells should be greater than $1.5\times10^7$, with the cell viability of above 95%. Bio-Rad electroporator is used to perform transformation, with a transfection voltage of 300 V and a capacitance of 900 μF. Cells are sub-cultured once every 2 to 3 days, fresh medium is replaced to culture the cells until the cells grow normally. When the cell viability is more than 90%, MTX pressure screening is performed. Concentration of MTX is gradually increased with 25 nM, 50 nM, 100 nM, 250 nM, 500 nM. Dividing plate is performed in accordance with the limiting dilution method when the MTX pressure reaches 500 nM. After clones are produced, Dot-blot detection is performed on the clones. 5 μl 96-well plate cell supernatant is taken to drop on nitrocellulose membrane. After air-dried, the nitrocellulose membrane is put into 5% skim milk and closed at room temperature for 30 minutes. 1:1000 dilution of RANK-Fc is added, and shocked at room temperature for 1 hour, and then is washed in TBST 3 times, for 5 minutes every time. The samples are put into 10,000 dilution of HRP-labeled goat anti-human IgG-Fc (purchased from Sigma), and shocked at room temperature for 1 hour, and colored by using DAB color system. Clones of a higher expression level are screened, a total of 120 clones were screened for the first time, and the clone of a highest expression level is sub-cloned, in order to ensure the obtained clone expressing human RANKL to be monoclonal clone.

(3) Purification of Human RANKL

Mass cultured cell supernatant was collected. After centrifugation, the sample is purified using a nickel column. The nickel chlorides in the nickel column may bond with His, and may also bond with imidazole. Firstly, the sample flows through the nickel column in a certain flow rate, so that the human RANKL in the sample bonds with the nickel column, and then different concentrations of imidazole is added to bond with the nickel column competitively with the human RANKL, so that the human RANKL was eluted. 2 ml $Ni^{2+}$ Sepharose 6 FF chromatography column is used, and is washed for 10 to 20 column volumes using Bonding buffer (20 mM PB+0.15 M NaCl, pH 7.4). the cell supernatants is added into the nickel column on 30 ml/h flow rate, the nickel column is washed for 10-20 column volumes with Bonding buffer, hybrid protein is washed away with 10 mM imidazole, and then 70 mM, 100 mM and 500 mM imidazole are used in elution respectively. Eluent is collected, and the main elution peak of human RANKL appears in 70 mM imidazole elution conditions. Purified human RANKL protein is identified by a reducing SDS-PAGE electrophoresis, with a molecular weight of about 34 KDa, which is consistent with the theoretical molecular weight, and the purity greater than 90%.

(4) Identification of Human RANKL

The prepared human RANKL and commercial hRANKL standard are coated on ELISA plates. The samples are diluted to 1 µg/ml, was added 100 and incubated overnight at 4° C. RANK-Fc gradient diluted from 10 µg/ml is added, 1:20,000 dilution of secondary antibody (goat anti-human IgG-Fc) is added, the sample is incubated for 1 hour at room temperature, is colored using TMB chromogenic color system. Absorbance value to each well of the 96-well plate is measured on the multifunction microplate reader with a measurement wavelength of 450 nm, a reference wavelength of 630 nm, absorbance value to each well (OD)=OD450 nm-OD630 nm. The bonding activity of human RANKL and RANK-Fc is identified. The results show that, the recombinant human RANKL coated on ELISA plates bonds with its receptor RANK-Fc, which depends on the concentration of RANK-Fc, and may reach saturation point, reach 50% maximal bonding with a concentration 10.9 ng/ml of RANK-Fc. The bonding of the human RANKL is consistent with that of the commercially available RANKL standard from R & D Systems, and the latter reach 50% maximal bonding with a concentration 5.6 ng/ml of RANK-Fc.

RAW264.7 cells are cultured using DMEM+10% FBS medium, are sub-cultured once every 3-4 days. For detection of the sample activity, the logarithmic phase of the cell culture medium is replaced with α-MEM medium+10% FBS. The cell suspension is seeded on a 96-well plate in 2000 cell/100 µl, put into an incubator at 37° C. with 5% $CO_2$ for 1 hour. The human RANKL diluted at two times from 800 ng/m is added, the commercially available hRANKL standard diluted at two times from 200 ng/m is added, and a fixed concentration of M-CSF and TGF β are added. The sample is put into an incubator at 37° C. with κ% $CO_2$ for 5 days, the cell supernatant is discarded, 100 µl cell lysis buffer (Citrate Buffer pH 5.0+0.5% Triton X-100) is added in each well, and the sample is lysed in refrigerator at 4° C. for 10 min. 100 µl pNPP color liquid is added in each well, and the sample is incubated at 37° C. for 30 min. Then, 50 µl stop solution (0.5 M NaOH) is added in each well, and the sample is identified on the multifunction microplate reader with 450/570 nm. Through the activity experimental identification of the human RANKL inducing the identification of RAW264.7 cells, the recombinant human RANKL can induce RAW264.7 cells to be differentiated into osteoclasts, and have a clear dose-dependent, for which the cell activity is similar to that of the product of R & D Systems. EC50 for the recombinant human RANKL is 113.4 ng/ml, and EC50 for the commercial hRANKL standard is 35.7 ng/ml.

This example shows that, recombinant and purified Human RANKL not only maintains the bonding ability with the corresponding RANK-Fc receptor, and also can stimulate the differentiation of osteoclasts via the receptor, and has biological activity. Recombinant human RANKL as an antigen is used to immunization procedures described herein, and is used as coated protein for the ELISA positive clones screening and the material for the antibody immunological and cytological feature identification.

Example 2 Mice Immunization and Titration

Antigen for immunization (the recombinant human RANKL) is obtained from Example 1, BALB/c mice are purchased from Beijing Wei Tong Li Hua Laboratory Animal Technology Limited Corporation. Anti-RANKL monoclonal antibodies are obtained by repeatedly immunizing BALB/c mice. Immunization is conducted by subcutaneous injection on a foot pad, the immunization dose is 10 g/50 µl/mice, 25 µl injected on each foot pad. A total of 10 mice are immunized.

In first immunization, 10 µg human RANKL is mixed with an equal volume of TiterMax Gold® (Sigma, Oakville, ON). 10 µg human RANKL is mixed with an equal volume of 100 µg alums (Sigma, Oakville, ON) and 10 µl pyrogen-free D-PBS containing CpG, without adjuvant in the following 10 multiple immunizations. BALB/c mice are immunized on 0, 5, 10, 15, 20, 25, 30, 35, 40 and 44 days, four mice with the highest serum titer are fused on 44 days.

Blood samples are drawn by post-occular puncture from 10 mice after the fifth immunization (day 20) and ninth immunization (day 40). The titer of the anti-human RANKL antibody in the immunized mice serum is measured by the ELISA method. Firstly, the human RANKL is diluted with a coating buffer (0.1 M coating buffer, pH 9.6 $NaHCO_3$ 8.4 g/L) to 1 µg/ml, is coated on a 96-well ELISA plate with 100 µl/well (Corning, Acton, Mass.), at 4° C. overnight. The next day, the plate is washed three times with 1×PBST (0.05% Tween 20 in 1×PBS), a blocking solution (0.5% BSA, 0.1% Tween 20, 0.01% Thimerosal in 1×PBS) is added with 200 µl/well, and the plate is closed at room temperature for 1 hour. The plate is washed three times, mice serum is diluted at 3 times from 1:100 with 0.5% BSA/PBS, 0.5% BSA/PBS is added in a blank well, the diluted mice serum is added in the ELISA plate with 100 µl/well and is incubated for 2 hours at room temperature. The plate is washed three times. A final concentration of 1 µg/ml goat anti-mouse IgG Fc-HRP is added, the sample is incubated at room temperature for 1 hour. The plate is washed three times, TMB (BioFx BSTP-0100-01) chromogenic color liquid is added at room temperature for 10-20 minutes, the Stop Solution is added, the sample is identified on the multifunction microplate reader with 450 nm readings. OD value is greater than 2 times of that for the blank wells, which is defined as a positive clone. The OD value is highest in a case that the serum is diluted at the highest times, which indicates that the immune response for the human RANKL is stronger. Serum titer test data are shown in Table 1. After the fifth immunization, serum titers of mice are up to 1:312500, in addition to #4 and #8 with 1:62500. After the ninth immunization, serum titers for mice are up to 1:1,562,500, in addition to #1 and #4 with 1:312500.

TABLE 1

| Mouse Number | Determination of serum titer for the first time immunization 5 times | Determination of serum titer for the second time immunization 9 times |
| --- | --- | --- |
| #1 | 1:312500 | 1:312500 |
| #2 | 1:312500 | 1:1562500 |
| #3 | 1:312500 | 1:1562500 |
| #4 | 1:62500 | 1:312500 |
| #5 | 1:312500 | 1:1562500 |

TABLE 1-continued

| Mouse Number | Determination of serum titer for the first time immunization 5 times | Determination of serum titer for the second time immunization 9 times |
|---|---|---|
| #6 | 1:312500 | 1:1562500 |
| #7 | 1:312500 | 1:1562500 |
| #8 | 1:62500 | 1:1562500 |
| #9 | 1:312500 | 1:1562500 |
| #10 | 1:312500 | 1:1562500 |
| Negative control (before immunization) | <100 | <100 |

Example 3 Production of Anti-Human RANKL Mouse Monoclonal Antibody

Immunized mice are euthanized with $CO_2$ and the neck vertebras are dislocated, lymph nodes are separated, and lymph nodes from different mice are mixed and are ground in DMEM medium, the supernatant is collected and centrifuged to obtain lymphocytes, and the lymphocytes are counted using a hemocytometer.

The above-obtained B cells are washed, and are mixed with non-secretory myeloma cells P3X63Ag8.653 (ATCC, Cat # CRL1580) in 1:1. The cell mixture is centrifuged at 800 g, the supernatant is gently removed. 2-4 ml Pronase solution (CalBiochem, cat #53702; 0.5 mg/ml in PBS) is added, in reaction for not more than two minutes. 3-5 ml FBS is added to stop the enzyme reaction, cell electric fusion solution ECFS (0.3 M Sucrose, Sigma, Cat # S7903, 0.1 mM Magnesium Acetate, Sigma, Cat # M2545, 0.1 mM Calcium Acetate, Sigma, Cat # C4705) is added to adjust the volume of the sample to be 40 ml. The sample is centrifuged, the supernatant is removed, and the cells are re-suspended in 40 ml ECFS to be washed once, ECFS is added to adjust the cell density to be $2\times10^6$ cells/ml. The sample is fused using an electrofusion device (ECM2001, BTX, Harvard Apparatus, Holliston, Mass.). A 2.0 ml fusion room is selected, and the parameters are set as follows:

Alignment condition: voltage: 50 V, time: 50 Sec
Membrane breaking at: voltage: 3000 V, time: 30 μSec
Post-fusion holding time: 3 Sec After the electrofusion, the supernatant is removed gently, and the sample is transferred into a sterile centrifuge tube containing an equal volume of hybridoma medium (DMEM (JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim)), is incubated at 37° C. for 15-30 min, and then is centrifuged at 400 g (1000 rpm) for 5 minutes. The cells are gently re-suspended in a small amount of hybridoma screening medium (Hybridoma Culture Medium supplemented with 0.5×HA (Sigma, cat. # A9666)) to adjust the cell density, and is gently mixed. $5\times10^6$ B-cells are seeded on each 96-well cell culture plate, with each well of 200 μl/well. At 7 or 10 days, the culture supernatant is removed at half, and 100 μl screening medium is added to each well.

After cells are cultured for 14 days, hybridomas with positive screened antibody that specifically bonds to RANKL are measured in hybridoma supernatants using the ELISA assay. The human RANKL is diluted to 1 μg/ml with a coating buffer (0.1 M Carbonate Buffer, pH 9.6, $NaHCO_3$ 8.4 g/L), is coated on the ELISA plate with 50 μl/wells, at 4° C. overnight. The next day, the plate is washed three times with a wash solution (0.05% Tween 20 in PBS), a blocking solution (0.5% BSA, 0.1% Tween 20, 0.01% Thimerosal in 1×PBS) is added with 200 μl/well. The plate isincubated at room temperature for 1 hour, and then the plate is washed three times, 50 μl hybridoma supernatant is added to each well, or positive and negative controls are prepared (the positive control includes human RANKL immunized mouse serum, the negative control includes the pre-immune BALB/c mouse serum). The sample is incubated for 2 hours at room temperature, and the plate is washed three times. Then, 1:2000 dilution of goat anti-mouse IgG-HRP (Jackson Lab, Cat. NO. 115-035-062) is added to each well, the sample is incubated for 1 hours at room temperature, and the plate is washed three times. 100 μl TMB color reagent (BioFX Lab. Cat. NO. TMSK-0100-01) is added to each well, the sample is colored at room temperature for 10 minutes, 50 μl stop solution is added to each well, and the sample is read at 450 nm. As a result, after the first round of screening, for a total of 190 96-well cell culture plates, 435 positive clones capable of bonding with the human RANKL are screened (OD value greater than 0.5).

For RANKL antibody positive clones in first ELISA screening, the medium for positive clones is removed, and fresh hybridoma culture medium is added, the clones are transferred to 24-well plates clone and are cultured for 2 days. A second round of ELISA plates screened verification experiment is carried out for the clones on the 24-well plates, which includes a direct ELISA detection, a competitive inhibition experiment and immunological cross reactivity with mouse RANKL. In the immunological cross reactivity with mouse RANKL, the protein packet is replaced by mouse RANKL with a concentration of 1 μg/ml, the detected sample is the original concentration of cell supernatant, i.e. a concentration point, and the rest of the experimental conditions are consistent with that in first ELISA screening experimental method. The results show that, nine clones have immunologically cross-reactivity with mouse RANKL. Competitive inhibition assay is a single-point test, RANK-Fc is diluted to 1 μg/ml with a coating buffer, at 4° C. overnight. The original concentration of supernatant is mixed with an equal volume of 600 ng/ml human RANKL, and then is added on the ELISA plate, incubated for 2 hours at room temperature, the plate is washed three times, 1:10,000 dilution of rabbit anti-human His-HRP (commercially available from Abcam) antibody is added, the sample is incubated for one hour at room temperature, the plate is washed 4 times. The sample is colored using TMB chromogenic color system, for 15 minutes at room temperature, 1 M $H_2SO_4$ is added to terminate the color. Absorbance value of each well on 96-well plates is measured on the multifunctional microplate reader (Molecular Devices SpectraMax M5 Multi-mode Microplate Reader) with a measurement wavelength of 450 nm and a reference wavelength of 630 nm, and the absorbance value of each well (OD)=OD450 nm-OD 630 nm. Clones with competitive activity are screened, for which the cell supernatant is diluted at 3 times for repeated experiment. The clones with a relatively strong competitive activity are selected to be sub-cloned in a new round, the cell lines are amplified and frozen, and the cell supernatant is purified to obtain an amount of the antibody for functional identification.

The second round ELISA results show that, 249 clones have OD values greater than 0.5, 41 clones have the activity of inhibiting the bonding of human RANKL and RANK-Fc, 9 clones have immunological cross-reactivity with mouse RANKL. The above-mentioned 50 clones are sub-cloned, the cell lines are frozen and the cell supernatant is purified to obtain the antibody for functional identification in Examples 4, 5, 6 and 7.

Example 4 Immunological Reactivity Between Purified Murine Monoclonal Antibody and Human RANKL The above-mentioned 41 clones having the neutralizing activity and 9 clones having immunological cross-reactivity with mouse RANKL are cultured for amplification. 100 ml hybridoma culture media is added in T125 square bottle, the samples are cultured in an incubator with 37° C., 5% $CO_2$ for 10 days, the cell supernatant is collected and purified using ProteinA to obtain the antibody. The samples are eluted with pH 3.0 citric acid buffer to collect samples, pH is adjusted to about 6.0. An antibody concentration measurement is performed on A280, and mg level of protein is obtained for each antibody. The bonding ability between the 50 anti-human RANKL mouse monoclonal antibodies and human RANKL immunogen is detected by the direct ELISA. Human RANKL protein is diluted to 1 μg/ml with pH 9.6 0.05 M carbonate buffer, and 100 μl per well is added on the 96-well ELISA plate at 4° C. overnight. The plate is washed three times with PBST, and is closed with PBST+2% BSA for 1 hour, and then plate is washed three times with PBST. The antibodies to be tested are diluted at 10 times with PBST from 10 μg/ml to $1\times10^5$ μg/ml. 100 μl per well is added on ELISA plate, the samples are placed into double wells, 5 samples are placed on each 96-well ELISA plate, and 10 96-well ELISA plates are prepared. After the antigen-antibody is incubated for 1 hour at room temperature, the samples are washed three times with PBST. 1:10,000 dilution of HRP-labeled goat anti-mouse IgG (available from Jackson Labs) is added to the antibody wells to be tested, with each well 100 and the samples are incubated for 1 hour at room temperature, the plate is washed four times with PBST washing solution. 100 μl TMB color reagent (purchased from Cell Signaling) is added in each well at room temperature in the dark for 7 minutes. 50 μl 1 M $H_2SO_4$ is added in each well to terminate the color reaction. Absorbance value of each well on 96-well plates is measured on the multifunctional microplate reader (Molecular Devices SpectraMax M5 Multi-mode Microplate Reader) with a measurement wavelength of 450 nm and a reference wavelength of 630 nm, and the absorbance value of each well (OD)=OD450 nm−OD630 nm.

An antigen-antibody bonding curve (FIG. 2) is obtained using Sigmoidal dose-response (variable slope) potting method with the antibody concentration as abscissa and the absorbance value of each well as ordinates (GraphPad Prism Software). The results show that, the majority of the anti-RANKL murine monoclonal antibodies may bond concentration-dependently with the human RANKL coated on the surface of the ELISA plate solid phase, and the bonding can reach saturation point, with an EC50 between 10-20 ng/ml, and the detailed data is listed in Table 2.

TABLE 2

Comparison of EC50 and other data about the bonding of murine monoclonal antibody and human RANKL

| | sample name | | | | | | | |
|---|---|---|---|---|---|---|---|---|
| | 114-7.19.12 | 114-7.37.26 | 114-7.38.48 | 114-6.6.29 | 114-5.7.14 | 114-5.9.4 | 114-2.402 | 114-2.222 |
| EC50 value (ng/ml) | 9.93 | 15.94 | 18.47 | 11.67 | 6.23 | 11.79 | 11.15 | 13.73 |

Example 5 Species Cross-Reactivity Between the Purified Mouse Monoclonal Antibody with Monkey RANKL and Mouse RANKL Species cross-reactivity between the anti-human RANKL mouse monoclonal antibody with cynomolgus monkey RANKL and mouse RANKL is detected with the direct ELISA method. The experimental method is identical to that in Example 4. The human RANKL, monkey RANKL and mouse RANKL are coated respectively, and monkey RANKL and mouse RANKL are purchased from R & D Systems.

An antigen-antibody bonding curve (FIG. 3) is obtained using Sigmoidal dose-response (variable slope) potting method with the antibody concentration as abscissa and the absorbance value of each well as ordinates (GraphPad Prism Software). The results show that, all the murine monoclonal antibodies capable of bonding with the human RANKL may bond concentration-dependently with the monkey RANKL, and the bonding may reach saturation point, with an EC50 between 10-20 ng/ml (Table 3). 9 antibodies in the detected antibodies have cross reactivity with mouse RANKL, for which the bonding is concentration-dependent and may reach saturation, with an EC50 between 10-20 ng/ml. Continued experiments show that the 9 antibodies cannot inhibit the bonding between RANKL and RANK-Fc.

TABLE 3 comparison of EC50 and other data about the bonding of murine monoclonal antibody and monkey RANKL

| | sample name | | | | | | | |
|---|---|---|---|---|---|---|---|---|
| | 114-7.19.12 | 114-7.37.26 | 114-7.38.48 | 114-6.6.29 | 114-5.7.14 | 114-5.9.4 | 114-2.402 | 114-2.222 |
| EC50 value (ng/ml) | 12.92 | 15.99 | 19.75 | 10.44 | 6.86 | 9.67 | 11.11 | 15.31 |

Example 6 Purified Murine Monoclonal Antibody Inhibiting the Bonding Activity of the Human RANKL with RANK-Fc It is evaluated whether the anti-human RANKL murine monoclonal antibody has a neutralizing activity to inhibit the bonding of the human RANKL with RANK-Fc with competitive ELISA experiments, and the anti-human RANKL murine monoclonal antibody is compared with commercially available products Denosumab. RANK-Fc protein is diluted to 1 μg/ml with pH 9.6 0.05 M carbonate buffer, and 100 μl per well is added on the 96-well ELISA plate at 4° C.

overnight. The plate is washed three times with PBST, and is closed with PBST+2% BSA for 1 hour, and then plate is washed three times with PBST. The antibodies to be tested and Denosumab are diluted respectively at 4 times with PBST from 20 μg/ml to 0.0024 μg/ml, and are mixed with an equal volume of human RANKL (with a concentration of 0.6 μg/ml) respectively. 100 μl per well is added on ELISA plate, the samples are placed into double wells, 5 samples and a Denosumab control sample are placed on each 96-well ELISA plate, and 10 96-well ELISA plates are prepared. After the samples are incubated for 2 hour at room temperature, the samples are washed three times with PBST. 1:10,000 dilution of HRP-labeled goat anti-mouse IgG (available from Jackson Labs) is added to the ELISA plate, with each well 100 μl, and the samples are incubated for 1 hour at room temperature, the plate is washed four times with PBST washing solution. 100 μl TMB color reagent (purchased from Cell Signaling) is added in each well at room temperature in the dark for 15 minutes. 50 μl 1 M $H_2SO_4$ is added in each well to terminate the color reaction. Absorbance value of each well on 96-well plates is measured on the multifunctional microplate reader with a measurement wavelength of 450 nm and a reference wavelength of 570 nm, and the absorbance value of each well (OD)=OD450 nm-OD570 nm.

A curve of antibody competitively inhibiting the bonding between receptor and ligand is obtained using Sigmoidal dose-response (variable slope) potting method with the antibody concentration as abscissa and the absorbance value of each well as ordinates (GraphPad Prism Software). 9 antibodies having cross reactivity with mouse RANKL have no activity of inhibiting the bonding between receptor and ligand; among the rest 41 antibodies, 8 antibodies lose the neutralizing activity, and the additional 33 antibodies have the significant neutralizing activity, can inhibit the bonding between RANKL and RANKL-Fc and are concentration-dependent. It is experimentally measured that Denosumab has EC50 of 0.67 μg/ml, while the EC50 values for 8 antibodies measured under the same experimental conditions are in a range of 0.2-1.0 μg/ml. The smaller EC50 values for the antibodies indicate that the activity of the antibodies for blocking the bonding between RANKL with RANK-Fc is stronger, and 5 antibodies in the 8 antibodies have the activity significantly better than Denosumab. FIG. 4 shows the results of inhibiting the bonding between RANKL and RANK-Fc for 8 samples, and the details are shown in Table 4.

tute) induced by human RANKL, and the anti-human RANKL murine monoclonal antibody is compared with commercially available products Denosumab. Osteoclasts have a characteristic enzyme, i.e., tartrate-resistant acid phosphatase, the degree of RAW264.7 cells being differentiated into osteoclasts may be reflected by the activity of the tartrate-resistant acid phosphatase which is indicated by the readings with 450/570 nm using the pNPP chromogenic system. RAW264.7 cells are cultured with DMEM+10% FBS (purchased from Invitrogen company) medium, are sub-cultured once every 3-4 days. For detection of the cell activity, the cells in the logarithmic phase are resuspended with α-MEM medium+10% FBS (purchased from Invitrogen company). The cell suspension is seeded on 96-well plates in 2000 cell/100 μl, put into an incubator (purchased from Thermo Fisher, specifications Forma 311) at 37° C. with κ% $CO_2$ for 1 hour. The samples to be tested which are diluted at two times, and Denosumab as well as human RANKL and MCSF, TGF-β (purchased from R & D Systems) are added (a total of 22 antibodies, 7 96-well cell culture plates). The final concentration of antibodies to be tested are 2000, 1000, 500, 250, 125 and 62.5 ng/ml respectively, the final concentration of human RANKL is 150 ng/ml, the final concentrations of MCSF and TGF-β are 20 ng/ml and 2 ng/ml respectively. The samples are placed in an incubator at 37° C., 5% $CO_2$ for 5 days, the cell supernatant is discarded, 100 μl cell lysis buffer (Citrate Buffer pH 5.0+0.5% Triton X-100) is added in each well, the samples are lysed in a refrigerator at 4° C. for 10 mins, 100 μl pNPP chromogenic solution (purchased from Sigma) is added to each well, the samples are incubated at 37° C. for 30 min, then 50 μl stop solution (0.5 M NaOH) is added to each well, and the samples are identified on the multifunction microplate reader with 450/570 nm. A curve of antibody inhibiting RAW264.7 cells to be differentiated into osteoclasts is obtained using Sigmoidal dose-response (variable slope) potting method with the antibody concentration as abscissa and the absorbance value of each well as ordinates (GraphPad Prism Software). The anti-RANKL murine monoclonal antibody is capable of completely inhibiting RAW264.7 cells induced by human RANKL to be differentiated into osteoclasts, and is dose-dependent. Except 114-6.6.7/114-6.6.18/114-6.6.29 samples with poor Inhibition, the rest 19 antibodies in the tested antibodies have strong inhibition activity, with very low EC50 values. The commercially available product Denosumab has EC50 of

TABLE 4 comparison of EC50 and other data about murine monoclonal antibody inhibiting the bonding of RANKL and RANK-Fc

| | Sample name | | | | | | | |
|---|---|---|---|---|---|---|---|---|
| | 114-7.19.12 | 114-7.37.26 | 114-7.38.48 | 114-6.6.29 | 114-5.7.14 | 114-5.9.4 | 114-2.402 | 114-2.222 | Denosumab |
| EC50 value (μg/ml) | 0.28 | 0.29 | 0.93 | 0.39 | 0.33 | 0.28 | 0.93 | 0.8 | 0.67 |

Figure 5:
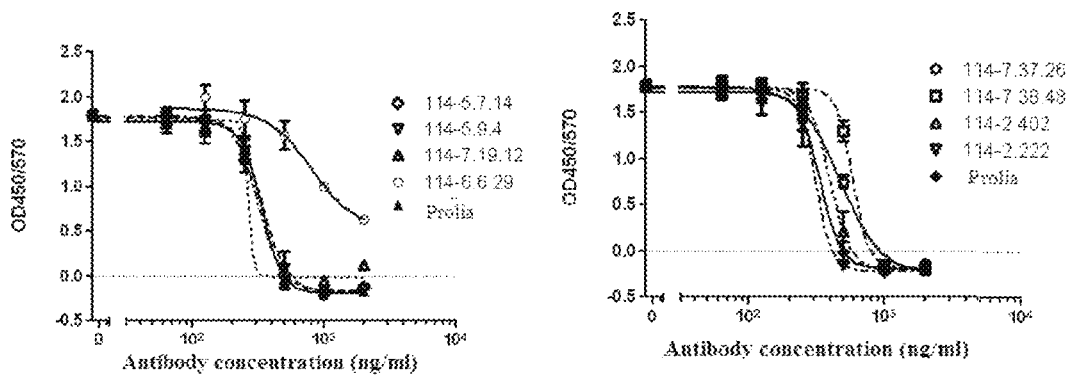
FIG. 5 shows a curve of anti-RANKL murine monoclonal antibody inhibiting the activity of RAW264.7 cell differentiation induced by human RANKL.

Example 7 Experiments that Murine Monoclonal Antibody Inhibits the Cellular Differentiation of RAW264.7 Induced by Human RANKL Human RANKL can induce RAW264.7 cells (purchased from Cell Bank of Shanghai Institute) to be differentiated into osteoclasts. The object of the experiment is to evaluate whether the anti-human RANKL murine monoclonal antibody capable of inhibiting the bonding of RANKL and RANK-Fc has the activity of inhibiting the cellular differentiation of RAW264.7 (mouse monocyte-macrophage leukemia cells, purchased from Cell Bank of Shanghai Insti- 334.4 ng/ml, while the EC50 values for 8 antibodies measured under the same experimental conditions are in a range of 200-800 ng/ml. The smaller EC50 values for the antibodies indicate that the activity of the antibodies for inhibiting the cellular differentiation of RAW264.7 induced by human RANKL is stronger, 3 antibodies in the obtained 8 antibodies have the activity significantly better than Denosumab, and 2 antibodies are equivalent to Denosumab. FIG. 5 shows the results of inhibiting RAW264.7 induced by human RANKL to be differentiated into osteoclasts for 8 samples, and the details are shown in Table 5.

TABLE 5

EC50 and other data about murine monoclonal antibody inhibiting the cellular differentiation of RAW264.7 induced by human RANKL

| | Sample name | | | | | | | | |
|---|---|---|---|---|---|---|---|---|---|
| | 114-7.19.12 | 114-7.37.26 | 114-7.38.48 | 14-6.6.29 | 14-5.7.14 | 14-5.9.4 | 14-2.402 | 114-2.222 | Denosumab |
| EC50 value (ng/ml) | 267.1 | 470.5 | 585.2 | 799.2 | 314.7 | 340.2 | 396 | 311.3 | 334.4 |

Example 8 Determination of Nucleic Acid Sequences in CDR Regions of the Anti-Human RANKL Murine Monoclonal Antibody Based on the experimental result of the murine monoclonal antibody inhibiting the bonding of RANKL and RANK-Fc and the experimental result of the murine monoclonal antibody inhibiting the cellular differentiation of RAW264.7, the antibodies having neutralizing activity are selected to determine the nucleic acid sequences in CDR regions. 22 samples are selected, are cultured with hybridoma medium, 1×10⁶ cells are collected and are centrifuged at 850 rpm for 5 minutes, the supernatant is removed, and the samples are resuspended by adding 450 μl RNAlater (purchased from Sigma) and are frozen in a refrigerator at −80° C. Specific ID information for the samples is listed as follows:

| | | | | | |
|---|---|---|---|---|---|
| 114-5.7.11 | 114.5.7.14 | 114-5.7.29 | 114-5.16.15 | 114-5.16.21 | 114-2.222 |
| 114-5.17.12 | 114-5.17.11 | 114-5.17.3 | 114-6.6.29 | 114-6.6.18 | 114-2.402 |
| 114-7.38.7 | 114-7.38.29 | 114-7.38.48 | 114-7.37.26 | 114-7.37.36 | |
| 114-7.19.12 | 114-7.19.17 | 114.5.9.4 | 114-6.6.7 | 114-5.16.3 | |

The collected 22 samples are sent to Nanjing GenScript Biotechnology Co., Ltd. to determine nucleic acid sequences in CDR regions. Firstly, total RNA is extracted using TRIzol® Plus RNA Purification System (Invitrogen, Cat No.: 15596-026), and then cDNA are obtained through reverse transcription by RT-PCR technology. Taking cDNA as a template, the variable region sequences of the heavy chain and the light chain are amplified with RACE method, the obtained variable region sequences are constructed into a sequencing vector, and nucleic acid sequence determination are performed on five positive clones selected from each variable region sequences. The nucleic acid sequences are translated into amino acid sequences. Through sequence alignment, finally the heavy and light chains have 8 unique CDR sequences respectively. Amino acid sequences of 9 samples of 114-5.7.11, 114-5.7.14, 114-5.7.29, 114-5.16.15, 114-5.16.3, 114-5.16.21, 114-5.17.12, 114-5.17.11 and 114-5.17.3 are identical exactly, amino acid sequences of 3 samples of 114-6.6.29, 114-6.6.18 and 114-6.6.7 are identical exactly, amino acid sequences of 3 samples of 114-7.38.7, 114-7.38-29 and 114-7.38.48 are identical exactly, amino acid sequences of samples 114-7.37.36 and 114-7.37.26 are identical exactly, and amino acid sequences of samples 114-7.19.12 and 114-7.19.17 are identical exactly. Specific amino acid sequence information is listed in Table 6.

TABLE 6

Amino acid sequence of CDR

| Antibody name | FR1 | CDR1 | FR2 | CDR2 | FR3 | CDR3 | FR4 |
|---|---|---|---|---|---|---|---|
| CDR sequence in the heavy chain | | | | | | | |
| 114-2.222 (SEQ ID NO. 2) | EVQLQQS GAELVKPG ASVKLSCT TSGFNIK | ATYIH | WVQQ RPEQ GLEW IG | RIDPAN GNTKY DSKFQ G | KATITADTSS NTAYLQLSS LTSEDTAVY FCAR | SLHYY VFFDY | WGQGT TLTVSS |
| 114-2.402 (SEQ ID NO. 3) | EVQLQQS GTELVKPG ASVKLSCT LFGFNIK | ATYMH | WVRQ RPEQ GLEW IG | RIDPPN GNTKY DPKFQ D | KATIKVDTS SNTAYLQLS SLTSEDTAV YYCAR | EFNRY DVWLA Y | WGQGT LVTVSA |
| 114-5.9.4 (SEQ ID NO. 4) | EVQLQQS GAELVKPG ASVKLSCT ASGFNLK | GTYIH | WVKQ RPGQ GLEW IG | RIDPAN ANTKY DPKFQ G | KATIRTDTS SNTAYLQLS SLTSEDTAV YFCSS | PSGHY DVWFA Y | WGQGT LVTVSP |
| 114-5.7.14 (SEQ ID NO. 5) | EVQLQQS GAELVKPG ASVKLSCT ASGFKIK | DTYMH | WVRQ RPEQ GLEW IG | RIDSAN GNIKY DPKFQ G | KATITADTSS KTAYLHLSS LTFEDTAVY YCSR | PKSNY DFWLP Y | WGQGT LVTVSA |
| 114-7.19.12 (SEQ ID NO. 6) | QVQLQQS GAELASPG ASVKLSCK ASGYTFT | TYWLQ | WVKQ RPGQ GLEW IG | AIYPGP GNTKY TQKFK D | KATLTADKS ASTAYMQL NSLTSEDSA VYYCAR | RGSRR GIAY | WGQGT LVTVSA |

TABLE 6-continued

Amino acid sequence of CDR

| Antibody name | FR1 | CDR1 | FR2 | CDR2 | FR3 | CDR3 | FR4 |
|---|---|---|---|---|---|---|---|
| 114-7.37.26 (SEQ ID NO. 7) | QVQLQQS GAELASPG ASVKLSCK TSGYTFT | TYWLQ | WVKQ RPGQ GLEW IG | AIYPGP GNTKY TQKFK D | KATLTADKS ASTAYMQLS SLTSEDSAV YYCAR | RGSRR GIAY | WGQGT LVTVSA |
| 114-738.48 (SEQ ID NO. 8) | DVQLQESG PDLVKPSQ SLSLTCTV TGYSIT | SAYSWH | WIRQ FPGN KLEW MG | YIHFSG VTNYN PSLKS | RISITRDASK NQFFLQLSS VTTEDTATY YCAT | RRETG FTY | WGQGT LVTVSA |
| 114-6.6.29 (SEQ ID NO. 9) | DVKLVESG GGLVKPG GSLKLSCA ASGFTFS | SYTMS | WVRQ TPEK RLEW VA | TISSGG SYTYY PDSVK G | RFTISRDNA KNTLYLQM SSLKSEDTA MYYCTR | DWDYY GTTYV GGYAM DY | WGQGT SVTVSS |

CDR sequences in the light chain

| 114-2.222 (SEQ ID NO. 10) | DIQMTQTT SSLSASLG DRVTISC | SASQGI SNYLN | WYQQKP DGTVKL LIY | STSS LHS | GVPSRFSGSGS GTDYSLTISSLE PEDIATYYC | QQYS KLPL T | FGAG TKLE LKR |
| 114-2.402 (SEQ ID NO. 11) | DIQMTQTT SSLSASLG DRVTISC | SASQG VSNYL N | WYQQKP DGTVKL LIY | STSS LHS | GVPSRFSCSGS GTDYSLTISNLE PEDVATYYC | QQYS KLPF T | FGSG TKLE IKR |
| 114-5.9.4 (SEQ ID NO. 12) | DIQMTQPT SSLSASLG DTVTISC | SASQDI SNYLN | WYQQKP DGTLKL LIY | YTSS LHS | GVPSRFSGSGS TDYRSLFTISNLE PEDIATYYC | QQFS KLPL T | FGAG TKLE LKR |
| 114-5.7.14 (SEQ ID NO. 13) | DIQMTQTT SSLSASLG DRVTISC | SASQGI SNYLN | WYQQKP DGTVKL LIV | YTSS LHS | GVPSRFSGSGS GTDYSLTISNLE PEDIATYYC | QQYS KLPL T | FGAG TKLE LK |
| 114-7.19.12 (SEQ ID NO. 14) | NIVLTQSPA SLAVSLGQ RATISC | RASES VDSYG RSFMH | WYQQRP GQPPTLL IY | LASN LES | GVPVRFSGSGS RTDFTLTIDPVE ADDAATYYC | QQDN EDPY T | FGGG TKLE IK |
| 114-7.37.26 (SEQ ID NO. 15) | NIVLTQSPA SLAVSLGQ RATISC | RASES VDSYG RSFMH | WYQQRP GQPPTLL IY | LASN LES | GVPARFSGSGS RTDFTLTIDPVE ADDAATYYC | QQDN EDPY T | FGGG TKLE IK |
| 114-7.38.48 (SEQ ID NO. 16) | DIVLTQSPA TLSVTPGD SVSLSC | RASQSI SKNLH | WYQQKS HESPRLL IK | YASQ SIS | GIPSRFSGSGS TDFTLSINSVET EDFGIYFC | QQIN SWPL T | FGAG TKLE LK |
| 114-6.6.29 (SEQ ID NO. 17) | DVLMTQT PLSLPVSL GDQASISC | RSSQSI VHSNG NTYLE | WYLQKP GQSPKL LIY | KVSN RFS | GVPDRFSGSGS GTDFTLKISRV EAEDLGVYYC | FQGS HVPW T | FGGG TKLE IK |

Example 9 Construction of 7.19.12 scFv (Single-Chain Antibody Fragment) Recombinant Plasmid Mice are immunized with recombinant human RANKL (hRANKL), a series of anti-human RANKL mouse monoclonal antibodies are obtained by hybridoma technology. The antibodies having neutralizing activity are screened through competitive ELISA experiments and cytology experiments, which can block the bonding of RANKL and its receptor RANK-Fc, inhibit RAW264.7 cells to be differentiated into osteoclasts. The monoclonal antibody 7.19.12 is one of antibodies with high bonding capacity and neutralizing activity, amino acid sequences in heavy chain variable region (VH) and light chain variable region (VL) for 7.19.12 has been published in China patent (Patent NO. CN201310753972.3). The scFv of 7.19.12 is constructed using PCR technology. 7.19.12 VH (SEQ ID NO.6) and VL (SEQ ID NO.14) are connected with a linker region (Gly4Ser) 3 to form a single-chain antibody (scFv) gene, and then are linked into T vector by T4 ligase to obtain 7.19.12 scFv (SEQ ID NO.21) recombinant plasmid.

Firstly, VH gene segments containing NcoI, XhoI restriction site and partial linker sequences are obtained by PCR amplification, using pfu DNA polymerase (purchased from Beijing Whole Style Gold Biotech) with VH5'NcoI and VH3'XhoI link as primers, 7.19.12 VH plasmid as a template; then VL gene fragments containing partial linker sequence, SacI and NotI restriction sites are obtained by PCR amplification, using pfu DNA polymerase with VL5'linkSacI-κ and VL3'NotI-κ primers, 7.19.12 VL plasmid as a template. 7.19.12 scFv gene fragments are obtained by PCR amplification, using pfu DNA polymerase with the obtained VH and VL gene fragments as the template, and VH5NcoI and VL3'NotI-κ as primers. The obtained 7.19.12 scFv products are extended using a rTaq polymerase (available from TAKARA) at 72° C. for 1 hour, to add A at 3' terminal of the scFv product. After A is added, the scFv product is recovered and purified through gel, the purified scFv product is connected to pMD®18-T vector under the influence of T4 DNA ligase (available from NEB) (16° C., 1 hour). E. coli is transformed with Heat shock method (42° C., 90 seconds), bacteria liquid is coated on plates (LB Amp medium), and are incubated overnight at 37° C. Clones are picked for colony PCR (universal primers M13-47 and M13-48) identification and screening, the positive clones verified through PCR are sequenced, and 7.19.12 scFv recombinant plasmids are screened. Primers for constructing 7.19.12 scFV are shown in Table 7.

TABLE 7 primers for constructing 7.19.12 scFv

| primer | sequences |
|---|---|
| VH5'NcoI | 5'-CATGCCATGGCCCAGGTTCAGCTCCAGCA GTCTGGGGCTGA-3' |
| VH3'XhoI link | 5'-ACCAGAGCCACCACCGCCTGAACCGCCAC CACCACTCGAGGCTGCAGAGACAGTGACCAGA GTCCCTTGGC-3' |
| VL5'linkSacI-κ | 5'-CAGGCGGTGGTGGCTCTGGTGGCGGTGGG AGCTCTAACATTGTGCTGACCCAATCTCCAG C-3' |
| VL3'NotI-κ | 5'-ATAAGAATTGCGGCCGCTTTTATTTCCAG CTTGGTCCCCCTCCG-3' |

7.19.12 DNA sequences (SEQ ID NO. 18) of a
variable region in the heavy chain
CAGGTTCAGCTCCAGCAGTCTGGGGCTGAACTGGCGAGTCCTGGGCT

TCAGTGAAGTTGTCCTGCAAGGCTTCTGGCTACACCTTTACTACCTAC

TGGCTGCAGTGGGTAAAGCAGAGGCCTGGACAGGGTCTGGAATGGATT

GGGGCTATTTATCCTGGACCTGGTAATACTAAATACACTCAGAAGTTC

AAGGACAAGGCCACATTGACTGCAGATAAATCCGCCAGCACAGCCTAC

ATGCAACTCAACAGCTTGACATCTGAAGACTCTGCGGTCTATTACTGC

GCAAGGAGGGGATCACGACGGGGGATTGCTTACTGGGGCCAAGGGACT

CTGGTCACTGTCTCTGCA 7.19.12 DNA sequences (SEQ ID NO. 19) of a
variable region in the light chain
AACATTGTGCTGACCCAATCTCCAGCTTCTTTGGCTGTGTCTCTAGGC

CAGAGGGCCACCATTTCCTGCAGAGCCAGTGAAAGTGTTGATAGTTAT

GGCAGAAGTTTTATGCACTGGTACCAGCAGAGACCAGGACAGCCACCC

ACACTCCTCATCTATCTTGCATCCAACCTAGAATCTGGGGTCCCTGTC

AGGTTCAGTGGCAGTGGGTCTAGGACAGACTTCACCCTCACCATTGAT

CCTGTGGAGGCTGATGATGCTGCAACCTATTACTGTCAGCAAGATAAT

GAGGATCCGTACACGTTCGGAGGGGGGACCAAGCTGGAAATAAAA 7.19.12 scFv DNA sequences
(SEQ ID NO. 20)
CAGGTTCAGCTCCAGCAGTCTGGGGCTGAACTGGCGAGTCCTGGGCT

TCAGTGAAGTTGTCCTGCAAGGCTTCTGGCTACACCTTTACTACCTAC

TGGCTGCAGTGGGTAAAGCAGAGGCCTGGACAGGGTCTGGAATGGATT

GGGGCTATTTATCCTGGACCTGGTAATACTAAATACACTCAGAAGTTC

AAGGACAAGGCCACATTGACTGCAGATAAATCCGCCAGCACAGCCTAC

-continued
ATGCAACTCAACAGCTTGACATCTGAAGACTCTGCGGTCTATTACTGC

GCAAGGAGGGGATCACGACGGGGGATTGCTTACTGGGGCCAAGGGACT

CTGGTCACTGTCTCTGCAGCCTCGAGTGGTGGTGGCGGTTCAGGCGGT

GGTGGCTCTGGTGGCGGTGGGAGCTCTAACATTGTGCTGACCCAATCT

CCAGCTTCTTTGGCTGTGTCTCTAGGCCAGAGGGCCACCATTTCCTGC

AGAGCCAGTGAAAGTGTTGATAGTTATGGCAGAAGTTTTATGCACTGG

TACCAGCAGAGACCAGGACAGCCACCCACACTCCTCATCTATCTTGCA

TCCAACCTAGAATCTGGGGTCCCTGTCAGGTTCAGTGGCAGTGGGTCT

AGGACAGACTTCACCCTCACCATTGATCCTGTGGAGGCTGATGATGCT

GCAACCTATTACTGTCAGCAAGATAATGAGGATCCGTACACGTTCGGA

GGGGGGACCAAGCTGGAAATAAAA 7.19.12 scFv amino acid sequence
(SEQ ID NO. 21)
QVQLQQSGAELASPGASVKLSCKASGYTFTTYWLQWVKQRPGQGLEWI

GAIYPGPGNTKYTQKFKDKATLTADKSASTAYMQLNSLTSEDSAVYYC

ARRGSRRGIAYWGQGTLVTVSAASSGGGGSGGGGSGGGGSSNIVLTQS

PASLAVSLGQRATISCRASESVDSYGRSFMHWYQQRPGQPPTLLIYLA

SNLESGVPVRFSGSGSRTDFTLTIDPVEADDAATYYCQQDNEDPYTFG

GGTKLEIK

Example 10 Construction of Wild-Type 7.19.12 scFv Phagemid

Figure 6:
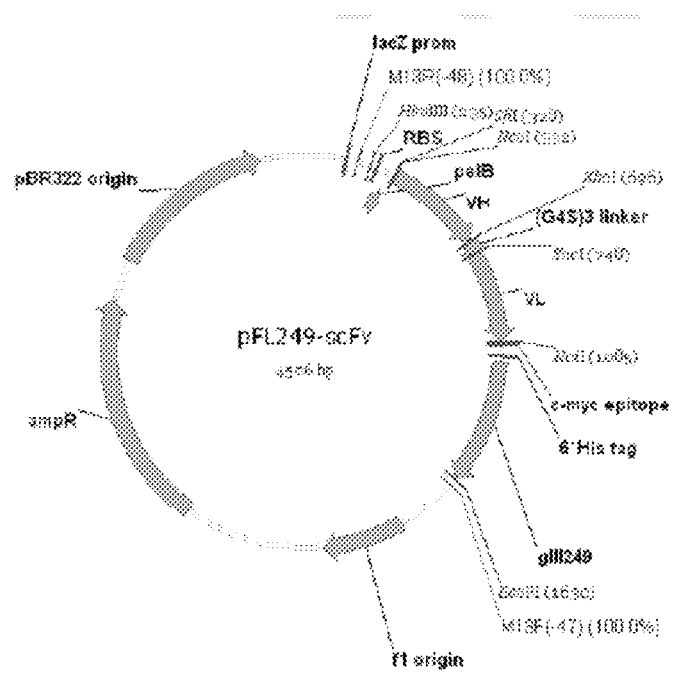
FIG. 6 shows a schematic diagram of pFL249-7.19.12 scFv plasmid.

Phagemid vector pFL249 are provided by Nanjing GenScript, NcoI and NotI are used as scFv gene insertion sites, pelB is signal peptide (for guiding scFv to be secreted into periplasmic space), gIII249 is phage recognition area, the ampicillin resistance gene is used to screen and maintain phagemids. The c-myc tag and his tag are connected via scFv gene, his tag is used in affinity purification, and c-myc tag may be identified by c-myc antibody in detection. Succinic terminator (TAG) exists between his tag and gill. Phagemid DNA plays a partial inhibition role in inhibiting-type E. coli TG1 (available from Lucigen, Cat. NO.60502-1), and may exhibit scFv on the surface of phage by assisting the phage.

pMD18-7.19.12 scFv plasmid are double digested with NcoI and NotI restriction enzymes (available from NEB), to obtain 7.19.12 scFv gene fragments with sticky ends, and 7.19.12 scFv gene fragments are connected with pFL249 vector subjected to the same double digestion process. Specific connection, transformation and identification methods are described in Example 9, and the wild-type pFL249-7.19.12 scFv phage are obtained by sequencing the clones (see FIG. 6).

Example 11 Design of 7.19.12 scFv Humanized Library

The human VH and VL gene sequences having the highest homology with 7.19.12 antibody framework region (Framework Regions, FRs) are determined by IgBlast search database (IMGT human V genes (F+ORF+in-frame P)). The FR sequences are checked to determine different amino acid residues between the human sequences and the mouse sequences, and the importance of each residue in antigen bonding is evaluated. Finally, the humanized sequences and the murine sequences which have different amino acid residues, for which the importance in antigen bonding cannot be determined, are indexed into humanized antibody sequences. Murine monoclonal antibody 7.19.12 VH humanized library mutations (7.19.12 VL is mutated fixedly for FR regions of 7.19.12 VH) are shown in Table 8, Murine monoclonal antibody 7.19.12 VL humanized library mutations (7.19.12 VH is mutated fixedly for FR regions of 7.19.12 VL) are shown in Table 9. The design diversity in VH humanized theory is $1 \times 10^5$, and The design diversity in VL humanized theory is 9216. The 7.19.12 scFv humanized library is synthesized in a way of degenerated bases (representation of degenerated bases as follows: N represents A/G/T/C, W represents A/T, B represents G/T/C, D represents G/A/T, R represents A/G, Y represents C/T, V represents A/G/C, M represents A/C, S represents G/C, H represents A/C/T, K represents G/T).

TABLE 8 mouse antibody 7.19.12 VH humanized library mutation strategy

| VH amino acid position | amino acid abbreviation | codon | Degenerate base |
|---|---|---|---|
| 5 | Q | CAG | SWG |
|   | V | GTG |   |
| 12 | A | GCG | RHS |
|   | K | AAA/AAG |   |
|   | V | GTC |   |
| 13 | S | ACT | MRK |
|   | K | AAG |   |
|   | Q | CAG |   |
| 38 | K | AAG | MRR |
|   | R | CGA |   |
| 40 | R | AGG | RSB |
|   | A | CCC |   |
|   |   | GCT |   |
| 48 | I | ATT | RTK |
|   | M | ATG |   |
|   | V | GTG |   |
| 67 | K | AAG | ARR |
|   | R | AGA |   |
| 68 | A | GCC | KYC |
|   | V | GTC |   |
|   | F | TTC |   |
| 70 | L | TTG | WTK |
|   | I | ATT |   |
|   | M | ATG |   |
| 74 | K | AAA | AMD |
|   | T | ACG |   |
|   | N | AAT |   |
| 76 | A | GCC | RMS |
|   | T | ACG |   |
|   | K | AAG |   |
| 87 | T | ACA | AVR |
|   | R | AGA |   |
|   | K | AAG |   |

TABLE 9 mouse antibody 7.19.12 VL humanized library mutation strategy

| VL amino acid position | amino acid abbreviation | codon | Degenerate base |
|---|---|---|---|
| 12 | A | GCT | KCT |
|   | S | TCT |   |
| 43 | R | AGA | ARA |
|   | K | AAA |   |

TABLE 9-continued mouse antibody 7.19.12 VL humanized library mutation strategy

| VL amino acid position | amino acid abbreviation | codon | Degenerate base |
|---|---|---|---|
| 47 | P | CCA | BCH |
|   | A | GCT |   |
|   | S | GCC/TCT |   |
| 49 | T | ACA | VDR |
|   | K | AGG |   |
|   | V | AAG |   |
|   | Q | CAG/GTG |   |
| 64 | V | GTC | KYM |
|   | A | GCC |   |
|   | S | TCA |   |
| 80 | D | GAT | RRY |
|   | S | AGC |   |
| 81 | P | CCT | VSN |
|   | S | AGC |   |
|   | R | GGG |   |
|   | G | AGA |   |
| 85 | D | GAT | GAW |
|   | E | GAA |   |
| 87 | A | GCT | KHK |
|   | F | TTT |   |
|   | V | GTT |   |
|   | E | GAG |   |

Example 12 Construction of 7.19.12 scFv Humanized Library

The construction of anti-hRANKL Mouse monoclonal antibody 7.19.12 scFv library is outsourced to Nanjing GenScript Biotechnology Co., Ltd. Ideas for library synthesis: respectively splitting VH and VL into four oligonucleotide sequence fragments of about 60~75 bp with about 20 bp overlapping between fragments, synthesizing VH mutation library fixed to VL and VL mutation library fixed to VH with overlapping extension PCR method. According to GenScript standard operating procedures, the synthesized $V_H$ primers and $V_L$ primers (see Table 10) are mixed in equimolar quantity, annealed, extended and amplified to be the complete $V_H$, $V_L$ fragments. The complete $V_H$, $V_L$ fragments are purified through gel and are cloned into sequencing vectors, 15, 20 clones are measured randomly to analyze PCR product diversity. Finally, the purified PCR product of $V_H$ with ORF normal clones percentage of 60% and 66% in two batches and the purified PCR product of $V_L$ with ORF normal clones percentage of 75% are selected.

The purified PCR product of VH is double digested with Sfi I and Xho I, and connected to a pFL249-7.19.12 scFv carrier double digested with Sfi I and Xho I, TG1 are electro-transformed, and VH mutation library fixed to VL is constructed. The purified PCR product of VL is double digested with Sac I and Not I, and connected to a pFL249-7.19.12 scFv carrier double digested with Sac I and Not I, TG1 is electro-transformed, and VL mutation library fixed to VH is constructed. Connection and electrical transformation tests are performed in Library construction, and a large number of connections and electrical transformations are performed according to the optimized conditions. 100 μl transformed library recovery bacteria is gradient diluted at 10 times. 100 μl each of three dilutions $10^{-3}$ to $10^{-5}$ of bacterial suspension is coated on 2×YT plates containing 100 μg/ml ampicillin, and cultivated at 37° C. overnight. The next day, the library capacity is computed by colony counting, and the remaining library recovery bacteria are coated on 2×YT plates (015 cm) containing 100 μg/ml ampicillin and 2% glucose, and cultivated at 37° C. overnight. The next day, colony is scraped from the plate and the library bacteria is collected, the library bacteria is re-suspended with glycerol to a 40% (V/V) final concentration, and the library glycerol bacteria is stored at −80° C.

Figure 7:
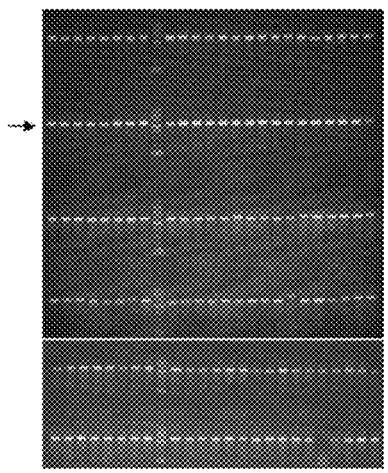
FIG. 7 shows an electrophoretogram for screening a PCR colony in a VH mutation library of a first batch.
Figure 8:
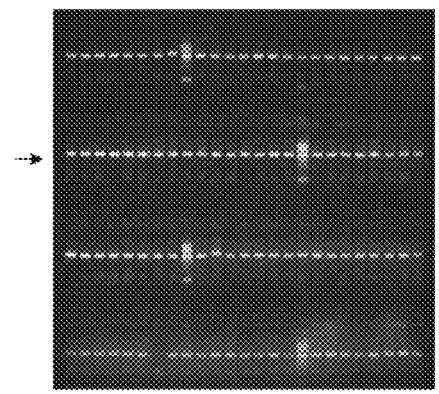
FIG. 8 shows an electrophoretogram for screening a PCR colony in a VH mutation library of a second batch.
Figure 9:
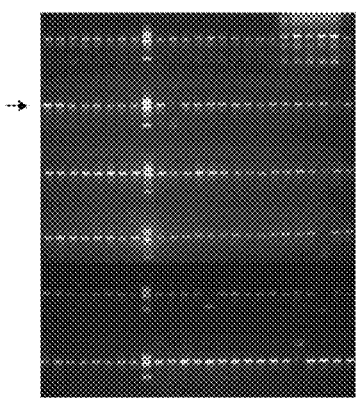
FIG. 9 shows an electrophoretogram for screening a PCR colony in a VL mutation library.

Statistics show that, the capacity of VH mutation library of the first batch is $1.35 \times 10^7$ (Table 11). 144 transformants are picked randomly using primers M13R (−48) and M13F (−47) by PCR colony screening. Transformants of about 1500 bp DNA bands (indicated by arrows) appearing in electrophoresis indicates that VH insert fragment is contained, and transformants containing no DNA bands is digested vector background. The results show that the positive rate is 98.6% (142/144, FIG. 7). The capacity of VH mutation library of the second batch is $1.04 \times 10^7$ (Table 12), 96 transformants are picked randomly using primers M13R (−48) and M13F (−47) by PCR colony screening, and the results of PCR colony screening show that the positive rate is 99% (95/96, FIG. 8). The total capacity of VH mutation library is approximately $2.04 \times 10^7$. The concentration of bacteria after the merger of bacteria in two batches is $6.7 \times 10^9$ cfu/ml. The capacity of VL mutation library is $2.8 \times 10^8$, and the concentration of bacteria is $2\ 10^{11}$ cfu/ml (Table 12). 144 transformants are picked randomly using primers M13R (−48) and M13F (−47) by PCR colony screening. Transformants of about 1500 bp DNA bands (indicated by arrows) appearing in electrophoresis indicates that VH insert fragment is contained, and transformants containing no DNA bands is digested vector background. The results of PCR colony screening show that the positive rate is 96.5% (139/144, FIG. 9). 100 positive colonies through PCR colony screening are randomly selected from VHNL mutation library respectively, and are sequenced. The sequencing results shows that 58/70 clones can be translated normally and conform to mutation design, and the diversity is equivalent to the test result.

TABLE 10

VH, VL primers for hRANKL mouse antibody 7.19.12 scFv humanized library

| Primer name | sequence information 5'-3' | length (bp) |
|---|---|---|
| P1455_Genor0012_VHFR1F | GGCCATGGCCCAGGTTCAGCTCSWGCAGTCTGGGGCTG AACTGRHSMRKCCTGGGGCTTCAGTGAAG | 67 |
| P1456_Genor0012_VHFR1R | CCAGTAGGTAGTAAAGGTGTAGCCAGAAGCCTTGCAGG ACAACTTCACTGAAGCCCCAGG | 60 |
| P1457_Genor0012_VHFR2F | ACCTTTACTACCTACTGGCTGCAGTGGGTAMRRCAGRS BCCTGGACAGGGTCTGGAATGG | 60 |
| P1458_Genor0012_VHFR2R | GTCCTTGAACTTCTGAGTGTATTTAGTATTACCAGGTCC AGGATAAATAGCCCCMAYCCATTCCAGACCCT GTCC | 75 |
| P1459_Genor0012_VHFR3F | ACTCAGAAGTTCAAGGACARRKYCACAWTKACTGCAG ATAMDTCCRMSAGCACAGCCTACATGCAA | 66 |
| P1460_Genor0012_VHFR3R | GCAGTAATAGACCGCAGAGTCTTCAGAYBTCAAGCTGT TGAGTTGCATGTAGGCTGTGCT | 60 |
| P1461_Genor0012_VHFR4F | TCTGCGGTCTATTACTGCGCAAGGAGGGGATCACGACG GGGGATTGCTTACTGGGGCCAA | 60 |
| P1462_Genor0012_VHFR4R | CCGCCACCACCACTCGAGGCTGCAGAGACAGTGACCAG AGTCCCTTGGCCCCAGTAAGCAAT | 62 |
| P1463_Genor0012_VHF | ATTGTTATTACTCGCGGCCCAGCCGGCCATGGCCCAGG TTCAGC | 44 |
| P1464_Genor0012_VHR | CCGCCACCACCACTCGAGGCTGCAGAG | 27 |
| P1465_Genor0012_VLFR1F | TGGGAGCTCTAACATTGTGCTGACCCAATCTCCAGCTTC TTTGKCTGTGTCTCTAGGCCAGAGG | 64 |
| P1466_Genor0012_VLFR1R | ACTATCAACACTTTCACTGGCTCTGCAGGAAATGGTGG CCCTCTGGCCTAGAGACAC | 57 |
| P1467_Genor0012_VLFR2F | GCCAGTGAAAGTGTTGATAGTTATGGCAGAAGTTTTAT GCACTGGTACCAGCAG | 54 |
| P1468_Genor0012_VLFR2R | AGATTCTAGGTTGGATGCAAGATAGATGAGGAGYHBG GGDGVCTGTCCTGGTYTCTGCTGGTACCAGTGCAT | 72 |
| P1469_Genor0012_VLFR3F | GCATCCAACCTAGAATCTGGGGTCCCTKYMAGGTTCAG TGGCAGTGGGTCTAGGACAGACTTCACCCTCACC | 72 |
| P1470_Genor0012_VLFR3R | CTGACAGTAATAGGTTGCMDMATCWTCAGCCTCCACN SBRYYAATGGTGAGGGTGAAGTCTGT | 63 |
| P1471_Genor0012_VLFR4F | GCAACCTATTACTGTCAGCAAGATAATGAGGATCCGTA CACGTTCGGAGGGGGG | 54 |

TABLE 10-continued

VH, VL primers for hRANKL mouse
antibody 7.19.12 scFv humanized library

| Primer name | sequence information 5'-3' | length (bp) |
|---|---|---|
| P1472_Genor0012_VLFR4R | TTTTTGTTCTGCGGCCGCTTTTATTTCCAGCTTGGTCCCCCCTCCGAACGTGTA | 54 |
| P1473_Genor0012_VLF | GTGGCGGTGGGAGCTCTAACATTGTGCTGACC | 32 |
| P1474_Genor0012_VLR | TTTTTGTTCTGCGGCCGCTTTTATT | 25 |

TABLE 11

Statistical results of the capacity of VH mutation library

| Gradient dilution | Number of transformants | |
|---|---|---|
|  | First batch | Second batch |
| $10^{-3}$ | 208 | 218 |
| $10^{-4}$ | 15 | 13 |
| $10^{-5}$ | 2 | 8 |

Note:
$1.5 \times 10^6$ transformants are obtained via a single electro-transformation of VH mutation library of first batch, $1.3 \times 10^6$ transformants are obtained via a single electro-transformation of VH mutation library of second batch, 9 electro-transformations and 8 electro-transformations are performed on the VH mutation library of the first batch and the second batch respectively, and the total library capacity is about $2.4 \times 10^7$ transformants.

TABLE 12

Statistical results of the capacity of VL mutation library

| Gradient dilution | Number of transformants |
|---|---|
| $10^{-3}$ | 2880 |
| $10^{-4}$ | 720 |
| $10^{-5}$ | 136 |

Note:
$2.8 \times 10^7$ transformants are obtained via a single electro-transformation of VL mutation library, 10 electro-transformations are performed on the VL mutation library, and the total library capacity is about $2.8 \times 10^8$ transformants.

Example 13 Selection of Phage Display Libraries

Firstly libraries is amplified, a certain amount of VH mutation library glycerol bacterial liquid is placed in 370 ml of 2×YT medium containing 100 μg/ml Amp and 2% glucose (hereinafter referred to 2×YT-AG), so that OD600 is in a range from 0.05 to 0.1. The bacterial liquid is cultured with shaking in 200 rpm/min at 37° C. until OD600 reaches a range from 0.3 to 0.4. M13KO7 helper phage (available from NEB, Cat. NO. N0315S) of 20 times of the total number of bacterial cells are added into the cultured bacterial liquid. After mixed, the bacterial liquid is infected in stand 37° C. for 30 minutes, and then is cultured with shaking in 200 rpm at 37° C. for 1 hour. The bacterial liquid is centrifuged at 2000 g for 10 min, the supernatant is removed, and then the bacteria is re-suspended in 370 ml 2×YT medium containing 100 μg/ml Amp and 50 μg/ml kanamycin (hereinafter referred to 2×YT-AK), cultured with shaking in 200 rpm/min at 30° C. overnight (for at least 15 hours). Then, the cultured bacterial liquid is transferred into a 500 ml centrifuge bottle, is centrifuged at 10,000 g for 15 min at 4° C., the supernatant is obtained, and added into PEG/NaCl solution (20% (W/V) polyethylene glycol (PEG) 8000, 2.5 M NaCl) with ¼ volume of the supernatant, and thoroughly mixed and deposited on ice for 1 hour. The mixed solution is centrifuged in 8000 rpm for 30 minutes at 4° C., the supernatant is removed, the precipitation was re-suspended in 2.2 ml PBS (137 mM NaCl, 2.7 mM KCl, 10 mM $Na_2HPO_4$, 1.8 mM$KH_2PO_4$, pH 7.2~7.4). The suspension is centrifuged in 10000 g for 2 minutes at 4° C., the supernatant (which shows recombinant scFv phage library) is saved backup at 4° C. (10 μl supernatant is picked and gradient diluted from $10^{-2}$ to $10^{-10}$ for titer determination).

CHO cell strains (C219) for stably expressing hRANKL are cultured, cell supernatant is collected, hRANKL protein is purified by $Ni^+$ column (see patent CN201310753972.3). The hRANKL is diluted with PBS to 10 μg/ml, and is added into Immuno™ tubes (purchased from NUNC, Cat. NO. 470319) according to 1 ml/tube, coated at 4° C. overnight. The tubes are washed 3 times with 5 ml PBST (containing 0.05% (V/V) Tween 20 in PBS), 5 ml blocking solution (PBS solution containing 10% (W/V) of skim milk) is added in tubes, and the tubes are closed at room temperature (20~25° C.) for 2 hours (another new Immuno™ tube is closed with the blocking solution as a negative control). Immuno™ tubes are washed 3 times with 5 ml PBST. The prepared recombinant phages are added into Immuno™ tubes, placed on a horizontal low-speed shaker in 60 rpm, and incubated at room temperature for 2 hours. The Immuno™ tubes are washed 10 times with 5 ml PBST and PBS respectively (the number of washings are increased to 15 times, 25 times and 35 times in second round, third round and fourth round respectively). After washed, 1 ml in E. coli TG1 with OD600 of 0.3 are added into the Immuno™ tubes, stand at 37° C. for 1 hour. 20 μl of infested TG1 bacteria is gradient diluted at 10 times. 100 μl of the infested TG1 bacteria of each of three dilution gradients from $10^{-2}$ to $10^{-4}$ is coated on SOB plates (Ø9 cm) containing 100 μg/ml ampicillin and 2% glucose (hereinafter referred to SOBAG), and incubated at 37° C. overnight. The next day, the capacity after each round of selection is calculated by colony counting. The remaining infested TG1 bacteria is coated on SOBAG plates (Ø9 cm), and incubated at 37° C. overnight. The next day, the colony is scraped from the plate and the library bacteria is collected, the library bacteria is re-suspended with glycerol to a 20% (V/V) final concentration. The library bacteria is amplified with the above-described library amplification method for the selection of the next round (selection method is the same as the above, the amount of coated antigen hRANKL is decreased gradually to be 10, 1, 0.05 and 0.01 μg/ml from the first round to the fourth round). The enrichment selection for VL mutation library is the same as that for VH library. Table 13 shows inputted amount of recombinant phage and total number of clones per selection round. As can be seen from data, the total number of clones for scFv antibody is reduced as the amount of antigen is decreased gradually, that is, scFv clones of non-specific bonding are reduced and scFv clones of specific bonding are enriched.

TABLE 13

Inputted amount of recombinant phage and total number of clones per selection round

| Selection round number | | Inputted amount of recombinant phage (cfu/ml) | Total number of clones per round |
|---|---|---|---|
| First round | VH | $1.72 \times 10^{11}$ | $8 \times 10^{7}$ |
| (10 μg/ml) | VL | $4.8 \times 10^{10}$ | $4 \times 10^{6}$ |
| Second round | VH | $1.6 \times 10^{10}$ | $1.6 \times 10^{7}$ |
| (1 μg/ml) | VL | $1.8 \times 10^{10}$ | $1.44 \times 10^{7}$ |
| Third round | VH | $\sim 2.0 \times 10^{10}$ | $1.75 \times 10^{6}$ |
| (0.05 μg/ml) | VL | $\sim 2.0 \times 10^{10}$ | $1.66 \times 10^{6}$ |
| Fourth round | VH | $\sim 2.0 \times 10^{10}$ | $7 \times 10^{4}$ |
| (0.01 μg/ml) | VL | $\sim 2.0 \times 10^{10}$ | $1.7 \times 10^{5}$ |

Example 14 Screening of scFv Specific Bonding with hRANKL Using ELISA Method

To screen positive clones capable of specifically bonding with hRANKL, the clones screened in example 13 are induced by IPTG to express scFv, and then the expressed scFv is detected with enzyme-linked immuno-sorbent assay (referred to as ELISA). For VH, VL libraries, 5×96 clones selected randomly from SOBAG cloning plates obtained in the third round and the fourth round are vaccinated on 96-deep-well plates respectively, 400 μl 2×YT-AG medium is contained in each well, the bacterial liquid is cultivated with shaking, at 30° C., 200 rpm overnight. The next day, the bacterial liquid on the deep-well plate is transferred by 1:50 to a new 96-deep-well plate containing 400 μl 2×YT-AG fresh medium. The bacterial liquid is cultivated with shaking at 37° C., 200 rpm until OD600 is about 0.8 (for about 3 hours). The bacterial is collected through 1500 g centrifugation for 10 minutes, the supernatant is removed, and the bacterial is resuspended with 400 μl of sterile fresh 2×YT-AI (I refers to IPTG, with a final concentration of 100 mM) culture medium, the suspension is cultivated with shaking at 30° C., 200 rpm overnight (that is, the expression of scFv is induced overnight). The expressed inductively scFv supernatant on the deep-well plate is centrifuged at 3000 g for 20 min, 300 μl supernatant is transferred to a clean 96-well cell plate for backup.

The hRANKL is diluted with 1×PBS (pH7.4) to 1 μg/ml, is added to a 96-well microtiter plate (available from NUNC, Cat. NO.442404) in accordance with 50 μl/well, with a total of 10 plates. The hRANKL is coated at 4° C. overnight. The plates are washed three times with PBST (containing 0.05% Tween 20). The plates are closed with blocking solution (PBS solution containing 2% (W/V) of BSA) for 1~1.5 hours at room temperature. The plates are washed three times with PBST, and then the induced scFv supernatant is transferred to a closed microtiter plate, with 50 μl/well, and a well containing only 2×YT-AI medium is used as a negative control, and a well containing wild-type 7.19.12 scFv supernatant is used as a positive control. The closed microtiter plate is incubated for 2 hours at room temperature, washed three times with PBST. Then, 1:5000 dilution of anti-c-myc HRP-labeled secondary antibody (purchased from Bethyl, item number A190-104P) is added, and the microtiter plate is incubated at room temperature for 1 hour. After the microtiter plate is washed six times with PBST, TMB substrate (purchased from Cell Signaling Technology, Cat. NO.7004) is added, and the samples are colored at room temperature for 10 minutes, 50 μl 2 M HCl is added in each well to terminate the color, and OD450 nm reading is detected using the M5 equipment.

Figure 10:
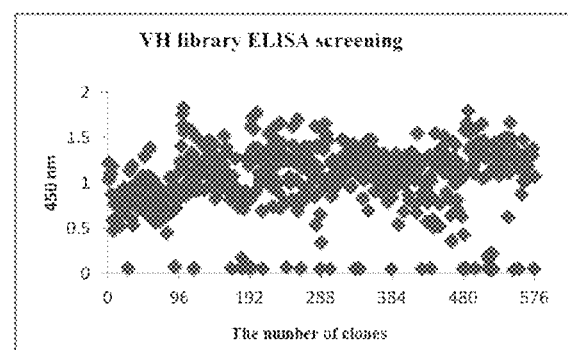
FIG. 10 shows results of ELISA screening in the VH library.
Figure 11:
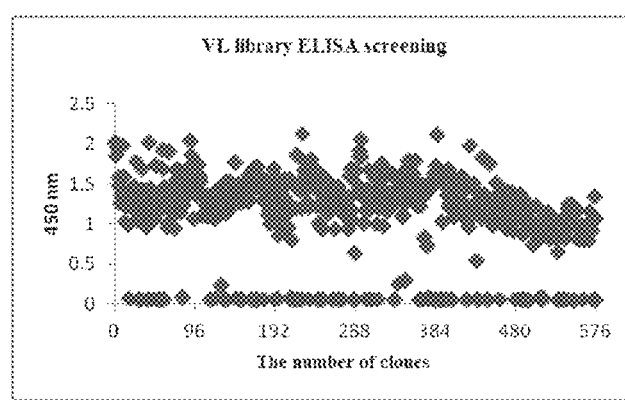
FIG. 11 shows results of ELISA screening in the VL library.

If OD450>0.4, it is considered as a positive coloration. The results show, 534 positive clones capable of bonding with hRANKL are obtained in VH libraries, and the positive rate is 94% (see FIG. 10), total 179 clones for which OD450>1.2 are selected and sent to Shanghai Megiddo organisms using primers M13R(−48) for sequencing. Through Sequence analysis, three VH sequences have higher humanized mutation degree, including 11 mutations, which meets humanized degree requirements, the three clones numbered pFL249-H16, pFL249-H16u and pFL249-H114; 486 positive clones capable of bonding with hRANKL are obtained in VL libraries, and the positive rate is 86% (see FIG. 11), 33 clones for which OD450>1.0 in third round and 114 clones for which OD450>1.5 in fourth round are selected and sent to Shanghai Megiddo organisms using primers M13R(−48) for sequencing. Through Sequence analysis, four VL sequences have higher humanized mutation degree, including 9 mutations, which meets humanized degree requirements, the four clones numbered pFL249-L10, pFL249-L10u, pFL249-L37 and pFL249-L37u.

Example 15 Construction of Expression Vectors for Heavy and Light Chain in the Anti hRANKL Humanized Antibody Three heavy chain variable regions H16 (SEQ ID NO.23), H16u (SEQ ID NO.25) and H114 (SEQ ID NO.27) obtained by phage screening platform are constructed to be IgG2-type full length heavy chains respectively, and four light chain variable regions L10 (SEQ ID NO.31), L10u (SEQ ID NO.33), L37 (SEQ ID NO.35) and L37u (SEQ ID NO.37) are constructed to be Kappa-type full length light chains respectively. The full length heavy chains and full length light chains are constructed on the eukaryotic expression vector pCDNA3.1. According to the determined sequences of positive clones obtained by phage screening, the framework regions (framework, hereinafter referred to as the FR) FR1, FR2, FR3 and FR4 in the light and heavy chain variable region are compared through IgBlast search database (IMGT human V genes (F+ORF+in-frame P)), to obtain a human FR region with the highest homology, and the human FR region is combined with the wild-type human FR region 7.19.12 CDRs to obtain a new VH (named H16 (hFR), SEQ ID NO.29) and VL (named WT-VL (hFR), SEQ ID NO.39) sequence. Genes in variable region are obtained by full gene synthesis, and the full-length heavy and light chains are constructed with the previous method, and are connected to an expression vector pCDNA3.1. Table 14 shows amino acid sequence alignments of the variable region in the heavy chain of anti-hRANKL humanized antibody, table 15 shows amino acid sequence alignments of the variable region in the light chain of anti-hRANKL humanized antibody, and 7.19.12 represents original mouse sequence.

DNA sequences (SEQ ID NO. 22) of a variable region in H16 heavy chain
CAGGITCAGCTCGTGCAGTCTGGGGCTGAACTGAAGAAGCCTGGGGC

TTCAGTGAAGTTGTCCTGCAAGGCTTCTGGCTACACCTTTACTACCT

```
ACTGGCTGCAGTGGGTAAGGCAGGCTCCTGGACAGGGTCTGGAATGG

ATGGGGGCTATTTATCCTGGACCTGGTAATACTAAATACACTCAGAA

GTTCAAGGACAGATTCACAATTACTGCAGATAAGTCCAAGAGCACAG

CCTACATGCAACTCAACAGCTTGAAGTCTGAAGACTCTGCGGTCTAT

TACTGCGCAAGGAGGGGATCACGACGGGGGATTGCTTACTGGGGCCA

AGGGACTCTGGTCACTGTCTCTGCA

Amino acid sequences (SEQ ID NO. 23) of a
variable region in H16 heavy chain
QVQLVQSGAELKKPGASVKLSCKASGYTFTTYWLQWVRQAPGQGLEW

MGAIYPGPGNTKYTQKFKDRFTITADKSKSTAYMQLNSLKSEDSAVY

YCARRGSRRGIAYWGQGTLVTVSA

DNA sequences (SEQ ID NO. 24) of a variable
region in H16u heavy chain
CAGGTTCAGCTCGTGCAGTCTGGGGCTGAACTGAAGAAGCCTGGGGC

TTCAGTGAAGTTGTCCTGCAAGGCTTCTGGCTACACCTTTACTACCT

ACTGGCTGCAGTGGGTAAGGCAGGCTCCTGGACAGGGTCTGGAATGG

ATGGGGGCTATTTATCCTGGACCTGGTAATACTAAATACACTCAGAA

GTTCAAGGACAGATTCACAATTACTGCAGATACGTCCAAGAGCACAG

CCTACATGCAACTCAACAGCTTGAAGTCTGAAGACTCTGCGGTCTAT

TACTGCGCAAGGAGGGGATCACGACGGGGGATTGCTTACTGGGGCCA

AGGGACTCTGGTCACTGTCTCTGCA

Amino acid sequences (SEQ ID NO. 25) of a
variable region in H16u heavy chain
QVQLVQSGAELKKPGASVKLSCKASGYTFTTYWLQWVRQAPGQGLEW

MGAIYPGPGNTKYTQKFKDRFTITADTSKSTAYMQLNSLKSEDSAVY

YCARRGSRRGIAYWGQGTLVTVSA

DNA sequences (SEQ ID NO. 26) of a variable
region in H114 heavy chain
CAGGTTCAGCTCGTGCAGTCTGGGGCTGAACTGGTGCAGCCTGGGGC

TTCAGTGAAGTTGTCCTGCAAGGCTTCTGGCTACACCTTTACTACCT

ACTGGCTGCAGTGGGTAAGGCAGACTCCTGGACAGGGTCTGGAATGG

ATGGGGGCTATTTATCCTGGACCTGGTAATACTAAATACACTCAGAA

GTTCAAGGACAGGGTCACAATTACTGCAGATACATCCACCAGCACAG

CCTACATGCAACTCAACAGCTTGAGATCTGAAGACTCTGCGGTCTAT

TACTGCGCAAGGAGGGGATCACGACGGGGGATTGCTTACTGGGGCCA

AGGGACTCTGGTCACTGTCTCTGCA

Amino acid sequences (SEQ ID NO. 27) of a
variable region in H114 heavy chain
QVQLVQSGAELVQPGASVKLSCKASGYTFTTYWLQWVRQTPGQGLEW

MGAIYPGPGNIKYTQKFKDRVTITADTSTSTAYMQLNSLRSEDSAVY

YCARRGSRRGIAYWGQGTLVTVSA

DNA sequences (SEQ ID NO. 28) of a variable
region in H16(hFR) heavy chain
CAGGTTCAGCTGGTGCAGTCTGGAGCTGAGGTGAAGAAGCCTGGGGC

CTCAGTGAAGGTCTCCTGCAAGGCTTCTGGTTACACCTTTACCACCT

ACTGGCTGCAGTGGGTAAGGCAGGCTCCTGGACAGGGTCTGGAATGG

ATGGGGGCTATTTATCCIGGACCTGGTAATACTAAATACACTCAGAA

GTTCAAGGACAGAGTCACGATTACCGCGGACGAATCCACGAGCACAG

CCTACATGGAGCTGAGCAGCCTGAGATCTGAGGACACGGCCGTGTAT

TACTGTGCGAGAAGGGGATCACGACGGGGGATTGCTTACTGGGGCCA

AGGGACTCTGGTCACTGTCTCTGCA

Amino acid sequences (SEQ ID NO. 29) of a
variable region in H16(hFR) heavy chain
QVQLVQSGAEVKKPGASVKVSCKASGYTFTTYWLQWVRQAPGQGLEW

MGAIYPGPGNTKYTQKFKDRVTITADESTSTAYMELSSLRSEDTAVY

YCARRGSRRGIAYWGQGTLVTVSA

DNA sequences (SEQ ID NO. 30) of a variable
region in L10 light chain
AACATTGTGCTGACCCAATCTCCAGCTTCITTGTCTGTGTCTCTAGG

CCAGAGGGCCACCATTTCCTGCAGAGCCAGTGAAAGTGTTGATAGTT

ATGGCAGAAGTTTTATGCACTGGTACCAGCAGAGACCAGGACAGGCT

CCCAGACTCCTCATCTATCTTGCATCCAACCTAGAATCTGGGGTCCC

TGCCAGGTTCAGTGGCAGTGGGTCTAGGACAGACTTCACCCTCACCA

TTAGCAGTGTGGAGGCTGAAGATGAGGCAACCTATTACTGTCAGCAA

GATAATGAGGATCCGTACACGTTCGGAGGGGGGACCAAGCTGGAAAT

AAAA

Amino acid sequences (SEQ ID NO. 31) of a
variable region in L10 light chain
NIVLTQSPASLSVSLGQRATISCRASESVDSYGRSFMHWYQQRPGQA

PRLLIYLASNLESGVPARFSGSGSRTDFTLTISSVEAEDEATYYCQQ

DNEDPYTFGGGTKLEIK

DNA sequences (SEQ ID NO. 32) of a variable
region in L10u light chain
AACATTGTGCTGACCCAATCTCCAGCTTCTTTGTCTGTGTCTCTAGG

CCAGAGGGCCACCATTTCCTGCAGAGCCAGTGAAAGTGTTGATAGTT

ATGGCAGAAGTTTTATGCACTGGTACCAGCAGAGACCAGGACAGGCT

CCCAAACTCCTCATCTATCTTGCATCCAACCTAGAATCTGGGGTCCC

TGCCAGGTICAGIGGCAGTGGGTCTAGGACAGACTTCACCCTCACCA

TTAGCAGTGTGGAGGCTGAAGATGAGGCAACCTATTACTGTCAGCAA

GATAATGAGGATCCGTACACGTTCGGAGGGGGGACCAAGCTGGAAAT

AAAA

Amino acid sequences (SEQ ID NO. 33) of a
variable region in L10u light chain
NIVLTQSPASLSVSLGQRATISCRASESVDSYGRSFMHWYQQRPGQA

PKLLIYLASNLESGVPARFSGSGSRTDFTLTISSVEAEDEATYYCQQ

DNEDPYTFGGGTKLEIK

DNA sequences (SEQ ID NO. 34) of a variable
region in L37 light chain
AACATTGTGCTGACCCAATCTCCAGCTTCTTTGTCTGTGTCTCTAGG

CCAGAGGGCCACCATTTCCTGCAGAGCCAGTGAAAGTGTTGATAGTT

ATGGCAGAAGTTTTATGCACTGGTACCAGCAGAAACCAGGACAGGCA

CCCAAGCTCCTCATCTATCTTGCATCCAACCTAGAATCTGGGGTCCC

TTCCAGGTTCAGTGGCAGTGGGTCTAGGACAGACTTCACCCTCACCA
```

-continued
TTAGCGCAGTGGAGGCTGAAGATGCGGCAACCTATTACTGTCAGCAA

GATAATGAGGATCCGTACACGTTCGGAGGGGGGACCAAGCTGGAAAT

AAAA

Amino acid sequences (SEQ ID NO. 35) of a
variable region in L37 light chain
NIVLTQSPASLSVSLGQRATISCRASESVDSYGRSFMHWYQQKPGQA

PKLLIYLASNLESGVPSRFSGSGSRTDFTLTISAVEAEDAATYYCQQ

DNEDPYTFGGGTKLEIK

DNA sequences (SEQ ID NO. 36) of a variable
region in L37u light chain
AACATTGTGCTGACCCAATCTCCAGCTTCTTTGTCTGTGTCTCTAGG

CCAGAGGGCCACCATTTCCTGCAGAGCCAGTGAAAGTGTTGATAGTT

ATGGCAGAAGTTTTATGCACTGGTACCAGCAGAAACCAGGACAGGCA

CCCAAGCTCCTCATCTATCTTGCATCCAACCTAGAATCTGGGGTCCC

TTCCAGGTTCAGTGGCAGTGGGTCTAGGACAGACTTCACCCTCACCA

TTAGCAGAGTGGAGGCTGAAGATGCGGCAACCTATTACTGTCAGCAA

GATAATGAGGATCCGTACACGTTCGGAGGGGGGACCAAGCTGGAAAT

AAAA

Amino acid sequences (SEQ ID NO. 37) of a
variable region in L37u light chain
NIVLTQSPASLSVSLGQRATISCRASESVDSYGRSFMHWYQQKPGQA

PKLLIYLASNLESGVPSRFSGSGSRTDFTLTISRVEAEDAATYYCQQ

DNEDPYTFGGGTKLEIK

DNA sequences (SEQ ID NO. 38) of a variable
region in WT-VL(hFR) light chain
GACATCGTGATGACCCAGTCTCCAGACTCCCTGGCTGTGTCTCTGGG

CGAGAGGGCCACCATCAACTGCAGAGCCAGTGAAAGTGTTGATAGTT

ATGGCAGAAGTTTTATGCACTGGTACCAGCAGAAACCTGGCCAGGCT

CCCAGGCTCCTCATCTATCTTGCATCCAACCTAGAATCTGGGGTCCC

CTCGAGGTTCAGTGGCAGTGGATCTGGGACAGATTTCACCCTCACCA

TCAATAGCCTGGAAGCTGAAGATGCTGCAACGTATTACTGTCAGCAA

GATAATGAGGATCCGTACACGTTCGGAGGGGGGACCAAGCTGGAAAT

AAAA

Amino acid sequences (SEQ ID NO. 39) of a
variable region in WT-VL(hFR) light chain
DIVMTQSPDSLAVSLGERATINCRASESVDSYGRSFMHWYQQKPGQA

PRLLIYLASNLESGVPSRFSGSGSGTDFTLTINSLEAEDAATYYCQQ

DNEDPYTFGGGTKLEIK

TABLE 14 amino acid sequence alignments of the
variable region in the heavy chain
of anti-hRANKL humanized antibody

| antibody name | FR1 | CDR1 | FR2 | CDR2 | FR3 | CDR3 | FR4 |
|---|---|---|---|---|---|---|---|
| 7.19.12 | QVQLQQSGA EtASPGASV KLSCKAS | GYTFT TYWLQ | WVKQRPG QGLEWIG | AIYPGPGNT KYTQKFKD | KATLTADKSAS TAYMQLNSLTS EDSAVYYCAR | RGSRR GIAY | WGQGTL VTVSA |
| H16 | QVQLVQSGA ELKKPGASV KLSCKAS | GYTFT TYWLQ | WVRQAPG QGLEWMG | AIYPGPGNT KYTQKFKD | RFTITADKSKS TAYMQLNSLKS EDSAVYYCAR | RGSRR GIAY | WGQGTL VTVSA |
| H16u | QVQLNQSGA ELKKPGASV KLSCKAS | GYTFT TYWLQ | WVRQAPG QGLEWMG | AIYPGPGNT KYTQKFKD | RFTITADTSKS TAYMQLNSLKS EDSAVYYCAR | RGSRR GIAY | WGQGTL VTVSA |
| H114 | QVQLVQSGA ELVQPGASV KLSCKAS | GYTFT TYWLQ | WVRQTPG QGLEWMG | AIYPGPGNT KYTQKFKD | RVTITADTSTS TAYMQLNSLRS EDSAVYYCAR | RGSRR GIAY | WGQGTL VTVSA |
| H16(hFR) | QVQLVQSGA EVKKPGASV KVSCKAS | GYTFT TYWLQ | WVRQAPG QGLEWMG | AIYPGPGNT KYYQKFKD | RVTITAGESTS TAYMELSSLRS EDTAVYYCAR | RGSRR GIAY | WGQGTL VTVSA |

TABLE 15 amino acid sequence alignments of the
variable region in the light chain
of anti-hRANKL humanized antibody

| antibody name | FR1 | CDR1 | FR2 | CDR2 | FR3 | CDR3 | FR4 |
|---|---|---|---|---|---|---|---|
| 7.19.12 | NIVLTQSP ASLAVSLG QRATISC | RASESVDS YGRSFMH | WYQQKPGQ PPTLLIY | LASN LES | GVPVRFSGSGS RTDFTLTIDPV EADDAATYYC | QQDNE DPYT | FGGGT KLEIK |

TABLE 15-continued amino acid sequence alignments of the
variable region in the light chain
of anti-hRANKL humanized antibody

| antibody name | FR1 | CDR1 | FR2 | CDR2 | FR3 | CDR3 | FR4 |
|---|---|---|---|---|---|---|---|
| L10 | NIVLTQSP ASLSVSLG QRATISC | RASESVDS YGRSFMH | WYQQKPGQ APRLLIY | LASN LES | GVPARFSGSGS RTDFTLTISSV EAEDEATYYC | QQDNE DPYT | FGGGT KLEIK |
| L10u | NIVLTQSP ASLSVSLG QRATISC | RASESVDS YGRSFMH | WYQQKPGQ APKLLIY | LASN LES | GVPARFSGSGS RTDFTLTISSV EAEDEATYVC | QQDNE DPYT | FGGGT KLEIK |
| L37 | NIVLTQSP ASLSVSLG QRATISC | RASESVDS YGRSFMH | WYQQKPGQ APKLLIY | LASN LES | GYPERFSGSGS RTDFTLTISAV EAEDAATYYC | QQDNE DPYT | FGGGT KLEIK |
| L37u | NIVLTQSP ASLSVSLG QRATISC | RASESVDS YGRSFMH | WYQQKPGQ APKLLIY | LASN LES | GVPSRFSGSGS RTDFTLTISRV EAEDAATYYC | QQDNE DPYT | FGGGT KLEIK |
| WT-VL(hFR) | DIVMTQSP DSLAVSLG ERATINC | RASESVDS YGRSFMH | WYQQKPGQ APRLLIY | LASN LES | GVPERFSGSGS GTDFTLTINSL EAEDAATYYC | QQDNE DPYT | FGGGT KLEIK |

Construction of Expression Vector for H16 Full Length Heavy Chain

H16 heavy chain variable region VH is obtained through PCR amplification, taking pFL249-H16 plasmid as a template; taking gene-synthesized human IgG2-type heavy chain constant region plasmid as a template, human IgG2 type heavy chain constant region (SEQ ID NO. 41) gene fragments are obtained through PCR amplification; H16 heavy chain gene VH-CH (SEQ ID NO.47) containing mammalian expression signal peptide (SEQ ID NO.45) are amplified by overlapping PCR technique; H16 full-length heavy chain genes are constructed to pCDNA3.1(+) (commercially available from Invitrogen, Cat. NO. V790-20) vectors to obtain H16 full-length heavy chain expression vectors.

H16 VH and IgG2 type CH gene fragments are amplified with pfu DNA polymerase (purchased from Beijing Whole Style Gold Biotech). VH gene fragments containing a part of the eukaryotic signal peptide are obtained through PCR amplification, with Whole-1H-F and Whole-1H-R as primers, and pFL249-H16 plasmid as a template; CH gene fragments containing TAG stop codon and NotI restriction sites are obtained through PCR amplification, with IgG2-CH-F and IgG2-CH-R as primers, and human IgG2 plasmid as a template. There are at least 20 bp overlapped sequences between the VH gene fragments and the CH gene fragments. The conditions for PCR are: 95° C.×2 min, [95° C.×20 seconds, 55° C.×20 seconds, 72° C.×40 seconds] for 30 cycles, 72° C.×5 min.

H16 heavy chain genes are amplified using pfu DNA polymerase. H16 heavy chain genes containing EcoRI and NotI restriction sites, and eukaryotic signal peptide sequence are obtained through PCR amplification, with the VH and CH gene fragments obtained by the above-mentioned PCR as a template, Whole-SP-F and IgG2-CH-R as primers. The conditions for PCR are: 95° C.×2 min, [95° C.×20 seconds, 55° C.×20 seconds, 72° C.×100 seconds] for 35 cycles, 72° C.×5 min.

Figure 12:
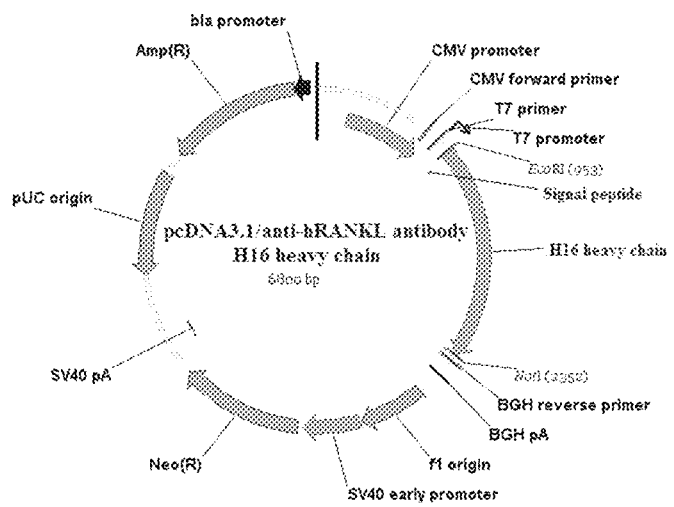
FIG. 12 shows a schematic plasmid map for H16 heavy chain.

H16 heavy chain genes obtained above are processed with the method of adding A in Example 9, recovered after gel and purified, and connected to pMD®19-T simple vector under the influence of the T4 DNA ligase (available from NEB Inc.) (16° C., 1 hour), and *E. coli* is transformed in heat shock (42° C., 90 seconds). The samples are coated on plates (LB Amp medium), cultivated at 37° C. overnight. Clones are picked for colony PCR (common primers M13-47 and M13-48) identification and Screening. Plasmids are extracted from positive clones through PCR identification. The positive clones are double digested with EcoRI and NotI, and approximately 1500 bp of H16 heavy chain fragment is recovered after gel, and connected to pCDNA3.1 (+) vector recovered after gel after the same double digestion process. Sequencing of H16 IgG2 heavy chain clones shows that, the full length of recombinant plasmid is 6800 bp, containing the H16 heavy chain variable region and human IgG2 heavy chain constant region (FIG. 12 shows a H16 heavy chain plasmid map).

DNA sequences (SEQ ID NO. 40) of a constant region in IgG2 heavy chain
GCCTCCACCAAGGGCCCATCGGTCTTCCCCCTGGCGCCCTGCTCCAG

GAGCACCTCCGAGAGCACAGCGGCCCTGGGCTGCCTGGTCAAGGACT

ACTTCCCTGAACCGGTGACGGTGTCGTGGAACTCAGGCGCTCTGACC

AGCGGCGTGCACACCTTCCCGGCTGTCCTACAGTCCTCAGGACTCTA

CTCCCTCAGCAGCGTGGTGACCGTGCCCTCCAGCAACTTCGGCACCC

AGACCTACACCTGCAACGTAGATCACAAGCCCAGCAATACCAAGGTG

GACAAGACAGTTGAGCGCAAATGTTGTGTCGAGTGCCCACCGTGCCC

AGCACCACCTGTGGCAGGACCGTCAGTCTTCCTCTTCCCCCCAAAAC

CCAAGGACACCCTCATGATCTCCCGGACCCCTGAGGTCACGTGCGTG

GTGGTGGACGTGAGCCACGAAGACCCCGAGGTCCAGTTCAACTGGTA

CGTGGACGGCGTGGAGGTGCATAATGCCAAGACAAAGCCACGGGAGG

AGCAGTTCAACAGCACGTTCCGTGTGGTCAGCGTCCTCACCGTCGTG

CACCAGGACTGGCTGAACGGCAAGGAGTACAAGTGCAAGGTCTCCAA

CAAAGGCCTCCCAGCCCCCATCGAGAAAACCATCTCCAAAACCAAAG

-continued
GGCAGCCCCGAGAACCACAGGTGTACACCCTGCCCCCATCCCGGGAG

GAGATGACCAAGAACCAGGTCAGCCTGACCTGCCTGGTCAAAGGCTT

CTACCCCAGCGACATCGCCGTGGAGTGGGAGAGCAATGGGCAGCCGG

AGAACAACTACAAGACCACGCCTCCCATGCTGGACTCCGACGGCTCC

TTCTTCCTCTACAGCAAGCTCACCGTGGACAAGAGCAGGTGGCAGCA

GGGGAACGTCTTCTCATGCTCCGTGATGCATGAGGCTCTGCACAACC

ACTACACGCAGAAGAGCCTCTCCCTGTCTCCGGGTAAA

Amino acid sequences (SEQ ID NO. 41) of a
constant region in IgG2 heavy chain
ASTKGPSVFPLAPCSRSTSESTAALGCLVKDYFPEPVTVSWNSGALT

SGVHTFPAVLQSSGLYSLSSVVTVPSSNFGTQTYTCNVDHKPSNTKV

DKTVERKCCVECPPCPAPPVAGPSVFLFPPKPKDTLMISRTPEVTCV

VVDVSHEDPEVQFNWYVDGVEVHNAKTKPREEQFNSTFRVVSVLTVV

HQDWLNGKEYKCKVSNKGLPAPIEKTISKTKGQPREPQVYTLPPSRE

EMTKNQVSLTCLVKGFYPSDIAVEWESNGQPENNYKTTPPMLDSDGS

FFLYSKLTVDKSRWQQGNVFSCSVMHEALHNHYTQKSLSLSPGK

DNA sequences (SEQ ID NO. 44) of expressing
signal peptides for mammalian
ATGGAGTTGGGACTGTCTTGGATTTTCCTGTTGGCTATTCTGAAAGG

TGTGCAGTGT

Amino acid sequences (SEQ ID NO. 45) of
expressing signal peptides for mammalian
MELGLSWIFLLAILKGVQC Construction of Expression Vectors for L10 Light Chain L10 light chain variable region VL is obtained through PCR amplification, with pFL249-L10 plasmid as a template; the human Kappa light chain constant region (SEQ ID NO.43) gene fragment is obtained through PCR amplification, with the gene-synthesized human Kappa light chain constant region plasmid as a template; L10 light chain genes VL-CL (SEQ ID NO.52) containing mammalian expression signal peptide (SEQ ID NO.45) are amplified by overlapping PCR technique; L10 light chain genes are constructed into pCDNA3.1 (+) vector to obtain L10 light chain expression vector.

L10 VL and Kappa light chain CL gene fragments are amplified with pfu DNA polymerase (purchased from Beijing Whole Style Gold Biotech). VL gene fragments containing a part of the eukaryotic signal peptide are obtained through PCR amplification, with Whole-IL-F and Whole-1L-R as primers, and pFL249-L10 plasmid as a template; CL gene fragments containing TAG stop codon and NotI restriction sites are obtained through PCR amplification, with CL-F and CL-R as primers, and human Kappa light chain plasmid as a template. There are at least 20 bp overlapped sequences between the VL gene fragments and the CL gene fragments. The conditions for PCR are: 95° C.×2 min, [95° C.×20 seconds, 55° C.×20 seconds, 72° C.×40 seconds] for 30 cycles, 72° C.×5 min.

L10 light chain genes are amplified using pfu DNA polymerase. L10 light chain genes containing EcoRI and NotI restriction sites, and eukaryotic signal peptide sequence are obtained through PCR amplification, with the VL and CL gene fragments obtained by the above-mentioned PCR as a template, Whole-IL-F and CL-R as primers. The conditions for PCR are: 95° C.×2 min, [95° C.×20 seconds, 55° C.×20 seconds, 72° C.×100 seconds] for 35 cycles, 72° C.×5 min.

Figure 13:
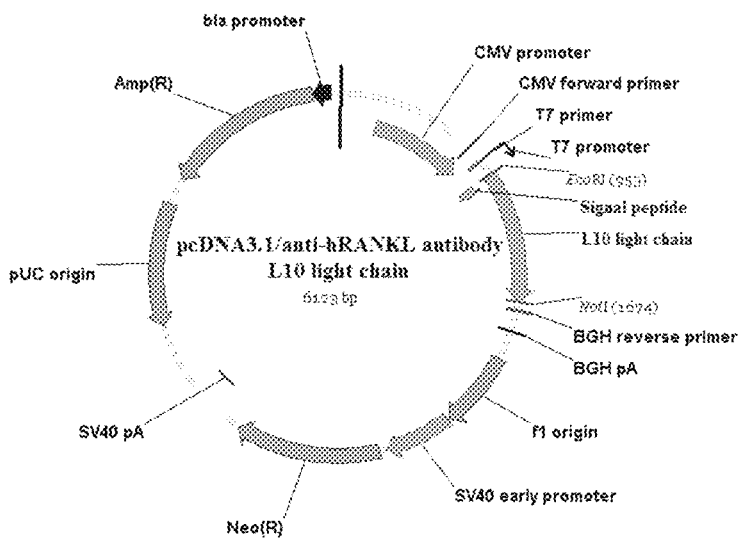
FIG. 13 shows the schematic plasmid map for L10 Kappa light chain.

L10 light chain genes obtained above are processed with the method of adding A in Example 9, recovered after gel and purified, and connected to pMD®19-T simple vector under the influence of the T4 DNA ligase (available from NEB Inc.) (16° C., 1 hour), and *E. coli* is transformed in heat shock (42° C., 90 seconds). The samples are coated on plates (LB Amp medium), cultivated at 37° C. overnight. Clones are picked for colony PCR (common primers M13-47 and M13-48) identification and Screening. Plasmids are extracted from positive clones through PCR identification. The positive clones are double digested with EcoRI and NotI, and proximately 750 bp of L10 light chain fragment is recovered after gel, and connected to pCDNA3.1 (+) vector recovered after gel after the same double digestion process. Sequencing of L10 light chain clones shows that, the full length of recombinant plasmid is 61223 bp, containing the L10 light chain variable region and a human Kappa light chain constant region (FIG. 13 shows L10 Kappa light chain plasmid map). Table 16 shows a list of primer for constructing carriers for a heavy chain and a light chain of the anti-hRANKL humanized antibody. The remaining three heavy chain (H16u, H114 and H16 (hFR)), and four light chain (L10u, L37, L37u and WT-VL (hFR)) similar) plasmid are constructed with the same method, which are not described in details herein.

DNA sequences (SEQ ID NO. 42) of a constant
region in Kappa light chain
GGTACTGTGGCTGCACCATCTGTCTTCATCTTCCCGCCATCTGATGA

GCAGTTGAAATCTGGAACTGCCTCTGTIGTGTGCCTGCTGAATAACT

TCTATCCCAGAGAGGCCAAAGTACAGTGGAAGGTGGATAACGCCCTC

CAATCGGGTAACTCCCAGGAGAGTGTCACAGAGCAGGACAGCAAGGA

CAGCACCTACAGCCTCAGCAGCACCCTGACGCTGAGCAAAGCAGACT

ACGAGAAACACAAAGTCTACGCCTGCGAAGTCACCCATCAGGGCCTG

AGCTCGCCCGTCACAAAGAGCTTCAACAGGGGAGAGTGT

Amino acid sequences (SEQ ID NO. 43) of a
constant region in Kappa light chain
GTVAAPSVFIFPPSDEQLKSGTASVVCLLNNFYPREAKVQWKVDNAL

QSGNSQESVTEQDSKDSTYSLSSTLTLSKADYEKHKVYACEVTHQGL

SSPVTKSFNRGEC

TABLE 16

List of primer for constructing carriers
for a heavy chain and a light chain of the
anti-hRANKL humanized antibody

| Primer name | Sequences (5' to 3') | Base pairs (bp) |
|---|---|---|
| Whole-SP-F | CCGGAATTCATGGAGTTGGG ACTGTCTTGGATTTTCCTGT TGGCTATTCTG | 51 |
| Whole-1H(WT)-F | GATTTTCCTGTTGGCTATTC TGAAAGGTGTGCAGTGTCAG GTTCAGCTCCAGCAGTCTG | 59 |
| Whole-1H-R | AAGACCGATGGGCCCTTGGT GGAGGCTGCAGAGACAGTGA CCAGAGTC | 48 |

TABLE 16-continued

List of primer for constructing carriers for a heavy chain and a light chain of the anti-hRANKL humanized antibody

| Primer name | Sequences (5' to 3') | Base pairs (bp) |
|---|---|---|
| IgG2-CH-F | GACTCTGGTCACTGTCTCTG CAGCCTCCACCAAGGGCCCA TCGGTCTT | 48 |
| IgG2-CH-R | ATAAGAATGCGGCCGCCTAT TTACCCGGAGACAGGGAGAG GCT | 43 |
| Whole-1H-F | GATTTTCCTGTTGGCTATTC TGAAAGGTGTGCAGTGTCAG GTTCAGCTCGTGCAGTCTG | 59 |
| 16H-H1-R | CTTGGACGTATCTGCAGTAA TTGTG | 25 |
| 16H-H2-F | CACAATTACTGCAGATACGT CCAAG | 25 |
| 114H-H1-R | ATCCATTCCAGACCCTGTCC AGGAGC | 26 |
| 114H-H2-F | GCTCCTGGACAGGGTCTGGA ATGGAT | 26 |
| Whole-1L-F | GATTTTCCTGTTGGCTATTC TGAAAGGTGTGCAGTGTAAC ATTGTGCTGACCCAATCTC | 59 |
| Whole-1L-R | ACAGATGGTGCAGCCACAGT ACCTTTTATTTCCAGCTTGG TCCCCCCT | 48 |
| CL-F | AGGGGGGACCAAGCTGGAAA TAAAAGGTACTGTGGCTGCA CCATCTGT | 48 |
| CL-R | ATAAGAATGCGGCCGCCTAA CACTCTCCCCTGTTGAAGCT CTTTG | 45 |
| 10L-L1-R | AGTTTGGGAGCCTGTCCTGG TTTC | 24 |
| 10L-L2-F | GAAACCAGGACAGGCTCCCA AACT | 24 |
| 37L-L1-R | CTCATCTTCAGCCTCCACTC TGCT | 24 |
| 37L-L2-F | AGCAGAGTGGAGGCTGAAGA TGAG | 24 |
| T7 primer | TAATACGACTCACTATAGGG | 20 |
| BGH primer | TAGAAGGCACAGTCGAGG | 18 |

Example 16 Expression and Purification of the Anti hRNAKL Humanized Antibody

Recombinant anti-hRNAKL antibodies are produced by FreeStyle™ 293-F cells (purchased from Invitrogen, Cat. NO. R790-07). DNA sequences encoding the entire heavy and light chains have been cloned into a mammalian expression vector, as detailed in Example 15. Vectors expressing an entire heavy chain and entire light chain are co-transfected into 293F cells under the mediation of cationic polymer PEI (available from Polysciences, Cat. NO.23966-2) to produce the anti-hRNAKL antibodies. For example, vectors expressing the entire heavy chain (amino acid sequence number SEQ ID NO.46) and the entire light chain (amino acid sequence number SEQ ID NO.51) are co-transfected into 293F cells to produce antibodies G1; vectors expressing the entire heavy chain (amino acid sequence number SEQ ID NO.47) and the entire light chain (amino acid sequence number SEQ ID NO.52) are co-transfected into 293F cells to produce antibodies G2; vectors expressing the entire heavy chain (amino acid sequence number SEQ ID NO.47) and the entire light chain (amino acid sequence number SEQ ID NO.53) are co-transfected into 293F cells to produce antibodies G3; vectors expressing the entire heavy chain (amino acid sequence number SEQ ID NO.47) and the entire light chain (amino acid sequence number SEQ ID NO.54) are co-transfected into 293F cells to produce antibodies G4; vectors expressing the entire heavy chain (amino acid sequence number SEQ ID NO.47) and the entire light chain (amino acid sequence number SEQ ID NO.55) are co-transfected into 293F cells to produce antibodies G5; vectors expressing the entire heavy chain (amino acid sequence number SEQ ID NO.48) and the entire light chain (amino acid sequence number SEQ ID NO.52) are co-transfected into 293F cells to produce antibodies G6; vectors expressing the entire heavy chain (amino acid sequence number SEQ ID NO.48) and the entire light chain (amino acid sequence number SEQ ID NO.53) are co-transfected into 293F cells to produce antibodies G7; vectors expressing the entire heavy chain (amino acid sequence number SEQ ID NO.48) and the entire light chain (amino acid sequence number SEQ ID NO.54) are co-transfected into 293F cells to produce antibodies G8; vectors expressing the entire heavy chain (amino acid sequence number SEQ ID NO.48) and the entire light chain (amino acid sequence number SEQ ID NO.55) are co-transfected into 293F cells to produce antibodies G9; vectors expressing the entire heavy chain (amino acid sequence number SEQ ID NO.49) and the entire light chain (amino acid sequence number SEQ ID NO.52) are co-transfected into 293F cells to produce antibodies G10; vectors expressing the entire heavy chain (amino acid sequence number SEQ ID NO.49) and the entire light chain (amino acid sequence number SEQ ID NO.53) are co-transfected into 293F cells to produce antibodies G11; vectors expressing the entire heavy chain (amino acid sequence number SEQ ID NO.49) and the entire light chain (amino acid sequence number SEQ ID NO.54) are co-transfected into 293F cells to produce antibodies G12; vectors expressing the entire heavy chain (amino acid sequence number SEQ ID NO.49) and the entire light chain (amino acid sequence number SEQ ID NO.55) are co-transfected into 293F cells to produce antibodies G13; vectors expressing the entire heavy chain (amino acid sequence number SEQ ID NO.50) and the entire light chain (amino acid sequence number SEQ ID NO.56) are co-transfected into 293F cells to produce antibodies G14. Table 17 shows a list of combination of heavy chain and light chain for anti-hRANKL antibody.

TABLE 17

List of combination of heavy chain and light chain for anti-hRANKL antibody

| Antibody | variable region in heavy chain + constant region in the heavy chain | Fully heavy chain |
|---|---|---|
| G1 | SEQ ID NO. 6 + SEQ ID NO. 41 | SEQ ID NO. 46 |
| G2 | SEQ ID NO. 23 + SEQ ID NO. 41 | SEQ ID NO. 47 |
| G3 | SEQ ID NO. 23 + SEQ ID NO. 41 | SEQ ID NO. 47 |
| G4 | SEQ ID NO. 23 + SEQ ID NO. 41 | SEQ ID NO. 47 |

TABLE 17-continued

List of combination of heavy chain and light chain for anti-hRANKL antibody

| | | |
|---|---|---|
| G5 | SEQ ID NO. 23 + SEQ ID NO. 41 | SEQ ID NO. 47 |
| G6 | SEQ ID NO. 27 + SEQ ID NO. 41 | SEQ ID NO. 48 |
| G7 | SEQ ID NO. 27 + SEQ ID NO. 41 | SEQ ID NO. 48 |
| G8 | SEQ ID NO. 27 + SEQ ID NO. 41 | SEQ ID NO. 48 |
| G9 | SEQ ID NO. 27 + SEQ ID NO. 41 | SEQ ID NO. 48 |
| G10 | SEQ ID NO. 25 + SEQ ID NO. 41 | SEQ ID NO. 49 |
| G11 | SEQ ID NO. 25 + SEQ ID NO. 41 | SEQ ID NO. 49 |
| G12 | SEQ ID NO. 25 + SEQ ID NO. 41 | SEQ ID NO. 49 |
| G13 | SEQ ID NO. 25 + SEQ ID NO. 41 | SEQ ID NO. 49 |
| G14 | SEQ ID NO. 29 + SEQ ID NO. 41 | SEQ ID NO. 50 |
| G15 | SEQ ID NO. 29 + SEQ ID NO. 41 | SEQ ID NO. 50 |

| Antibody | variable region in light chain + constant region in the light chain | Fully light chain |
|---|---|---|
| G1 | SEQ ID NO. 14 + SEQ ID NO. 43 | SEQ ID NO. 51 |
| G2 | SEQ ID NO. 31 + SEQ ID NO. 43 | SEQ ID NO. 52 |
| G3 | SEQ ID NO. 35 + SEQ ID NO. 43 | SEQ ID NO. 53 |
| G4 | SEQ ID NO. 33 + SEQ ID NO. 43 | SEQ ID NO. 54 |
| G5 | SEQ ID NO. 37 + SEQ ID NO. 43 | SEQ ID NO. 55 |
| G6 | SEQ ID NO. 31 + SEQ ID NO. 43 | SEQ ID NO. 52 |
| G7 | SEQ ID NO. 35 + SEQ ID NO. 43 | SEQ ID NO. 53 |
| G8 | SEQ ID NO. 33 + SEQ ID NO. 43 | SEQ ID NO. 54 |
| G9 | SEQ ID NO. 37 + SEQ ID NO. 43 | SEQ ID NO. 55 |
| G10 | SEQ ID NO. 31 + SEQ ID NO. 43 | SEQ ID NO. 52 |
| G11 | SEQ ID NO. 35 + SEQ ID NO. 43 | SEQ ID NO. 53 |
| G12 | SEQ ID NO. 33 + SEQ ID NO. 43 | SEQ ID NO. 54 |
| G13 | SEQ ID NO. 37 + SEQ ID NO. 43 | SEQ ID NO. 55 |
| G14 | SEQ ID NO. 39 + SEQ ID NO. 43 | SEQ ID NO. 56 |
| G15 | SEQ ID NO. 31 + SEQ ID NO. 43 | SEQ ID NO. 52 |

During 24 hours before the transfection, 293-F cells are subcultured to a 6~7×10$^5$ cells/mL density, cultured under conditions of 8% $CO_2$, 135 rpm at 37° C. The next day, the density and viability of cells are determined using a hemocytometer, to ensure that the viability is more than 95%. The density of cells was adjusted to 1×10$^6$/mL for instantaneous transfer experiments. 15 μg of each of the light chain plasmids and heavy chain plasmids are added into OptiPRO SFM (purchased from Invitrogen) with a centrifuge tube (tube A), with a final volume of 600 4, and mixed gently; 90 μg PEI transfection reagent is added into OptiPRO SFM with a new centrifuge tube (tube B), with a final volume of 600 μL, and mixed gently. Instantly, the liquid in the tube B is draw into the tube A, and mixed gently. The mixture of A and B is placed at room temperature for 20 minutes, are added dropwise into 30 ml 293-F cells. Cells are transfected and then cultured in a shaker at 37° C., 8% $CO_2$, 135 rpm. At 6 to 7 days after transfection, the viability of transfected cells are measured, cell supernatants are collected and purified in a case that the cell viability is below 50%.

The cell supernatants are collected after centrifugation at 9000 rpm for 30 minutes, and the antibodies are purified using rProtein A (available from GE, Best Chrom) gravity column. 5-10 column volumes of equilibration solution (20 mM Tris-HCl+0.15 M NaCl pH7.4) are used for balance, and the flow rate of samples is controlled to be less than or equal to 1 ml/min. After the samples are finished, 5-10 column volumes of equilibration solution are used for balance. The antibodies are eluted with 100 mM citric acid (pH3.0), the collected eluent is neutralized with 1 M Tris-HCl (pH9.0) and adjusted to be with pH of about 6.0. The antibody solution is concentrated by centrifugation with 10 KD ultrafiltration tube (available from Millipore Corporation, Cat. NO. UFC901008), and are resuspended with PBS (137 mM NaCl, 2.7 mM KCl, 10 mM $Na_2HPO_4$, 1.8 mM $KH_2PO_4$, pH7.2~7.4). The protein concentration of the antibody suspension is determined using modified BCA Protein concentration Assay kit (purchased from Shanghai Sangon), and the antibody suspension is filtered and sterilized using 0.22 μM membrane (available from Millipore Corporation, Cat. NO. SLGP033RB), and saved in packages at −80° C.

Example 17 Detection of the Bonding Ability Between Humanized Antibody and hRNAKL Using ELISA Method The hRANKL is diluted to 1 μg/ml with PBS (137 mM NaCl, 2.7 mM KCl, 10 mM $Na_2HPO_4$, 1.8 mM $KH_2PO_4$, pH7.2~7.4), added to a 96-well microtiter plate (available from NUNC) in accordance with 100 μl/well. The microtiter plate is coated at 4° C. overnight. The plates are washed three times with PBST (PBS solution containing 0.05% Tween20). The plates are closed with blocking solution (PBS solution containing 2% (W/V) of BSA, abbreviated as PBS-2% BSA) for 1 1.5 hours at room temperature. The humanized antibody G2-G14, murine antibody G1 and a positive control Prolia (commercially available from Amgen Corporation, lot number 1021139) are respectively diluted at 3 times from 1 μg/ml to 0.0002 μg/ml with a sample dilution liquid (PBS-1% BSA), added into the microtiter plate with 100 μl/well, and incubated at room temperature for 2 hours. The plates are washed three times with PBST, and HRP-labeled goat anti-human IgG Fc antibody (Jackson, Item NO.109-035-098) is diluted at 1:10,000 with PBS-1% BSA, added into the microtiter plate with 100 μl/well, and incubated at room temperature for 1 hours. After plates are washed six times with PBST, TMB substrate (Cell Signaling, Item NO.7004) is added into the microtiter plate, and the sample is colored at room temperature for 10 minutes. 100 μl 2 M HCl is added in each well to terminate the color, and OD450 nm reading is detected using the M5 equipment.

Figure 14A:
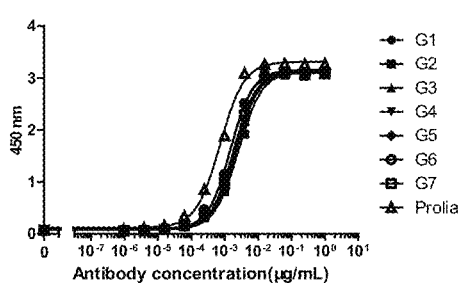
FIGS. 14A-14C show comparison on the activity of the bonding between the humanized antibody and hRANKL.
Figure 14:
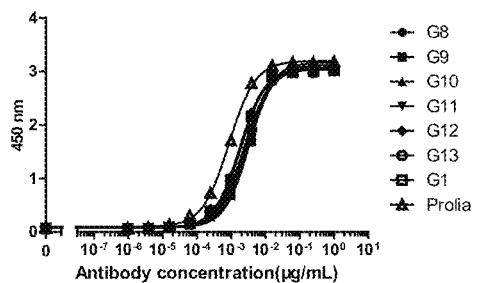
Figure 14C:
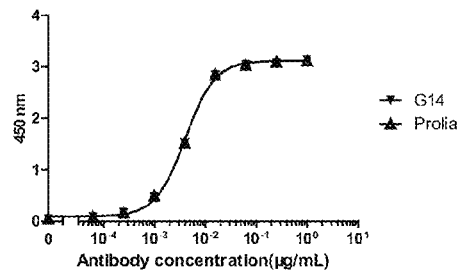

An bonding curve of antibodies and hRANKL (FIG. 14A/14B/14C) is obtained using log (agonist) vs. response—Variable slope potting method with the antibody concentration as abscissa and the absorbance value of each well as ordinates (GraphPad Prism Software). The results show that, 13 humanized antibodies are capable of bonding with hRANKL concentration-dependently and can reach saturation, reach 50% the maximum degree of bonding when the concentration of antibody is between 1-4 ng/ml, have considerable bonding ability compared with G1 and Prolia. The concentrations of antibodies when 50% the maximum degree of bonding is reached are shown in Table 18.

TABLE 18

Comparison of concentrations of antibodies in a case that the humanized antibody bonds hRANKL up to a level of 50% Bmax

| Plate#01 | Antibody name | G1 | G2 | G3 | G4 | G5 | G6 | G7 | Prolia |
|---|---|---|---|---|---|---|---|---|---|
| | 50% Bmax (ng/ml) | 1.47 | 2.55 | 1.87 | 1.95 | 2.21 | 1.47 | 1.82 | 0.72 |
| Plate#02 | Antibody name | G8 | G9 | G10 | G11 | G12 | G13 | G1 | Prolia |
| | 50% Bmax (ng/ml) | 2.76 | 3.28 | 2.85 | 1.90 | 1.75 | 2.34 | 1.88 | 0.85 |

TABLE 18-continued

Comparison of concentrations of antibodies in a case that the humanized antibody bonds hRANKL up to a level of 50% Bmax

| Plate#03 | Antibody name | G14 | Prolia |
|---|---|---|---|
| | 50% Bmax (ng/ml) | 4.00 | 4.01 |

Example 18 Detection of the Inhibition Ability of Humanized Antibodies for the Bonding of RANK-Fc and hRANKL Using Competitive ELISA Method Competitive ELISA experiments are carried out to evaluate the ability of hRANKL humanized antibodies for inhibiting the bonding of receptor RANK-Fc and ligand hRANKL, compared with Prolia. RANK-Fc is diluted with PBS to 2 µg/ml, added into the microtiter plate with 100 µl/well, the microtiter plate is coated at 4° C. overnight. The humanized antibody (G2-G14), mouse antibody (G1) and the positive control Prolia are diluted with sample diluent (PBS-1% BSA). The above-mentioned antibody with the final concentrations of 30, 10, 3.3, 1.1, 0.37, 0.12, 0.04, 0.01, 0.005, 0.0015, 0.0005 µg/ml respectively are mixed with 0.25 µg/ml of hRANKL, and the mixture is pre-incubated at 4° C. overnight. The plate is washed three times with PBST (PBS solution containing 0.05% Tween20), the plate is closed with blocking solution (PBS-2% BSA) for 1~1.5 hours at room temperature, and then the plate is washed three times with PBST. The pre-incubated mixture is added into the closed microtiter plate with 100 µl/well, a well with PBS-1% BSA is used as a negative control, and a well containing only 0.25 µg/ml hRANKL well is used as a positive control. Reaction at room temperature for 1 hour. The plate is washed three times with PBST, HRP-labeled anti-His tag antibody (purchased from Abcam, Cat. NO. ab1187) is diluted at 1:5,000 with PBS solution containing 1% BSA and 0.05% Tween, added into a microtiter plate with 100 µl/well, and incubated for 1 hour at room temperature. After plate is washed six times with PBST, TMB substrate (Cell Signaling, Item NO. 7004) is added into the microtiter plate, and the sample is colored at room temperature for 10 minutes. 100 µl 2 M HCl is added in each well to terminate the color, and OD450 nm reading is detected using the M5 equipment.

Figure 15A:
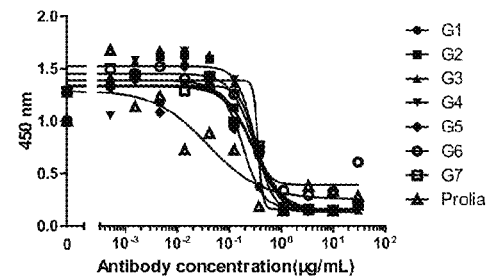
FIGS. 15A-15C show comparison on the activity of the humanized antibody competitively inhibiting the bonding between hRANKL and RANK-Fc.
Figure 15B:
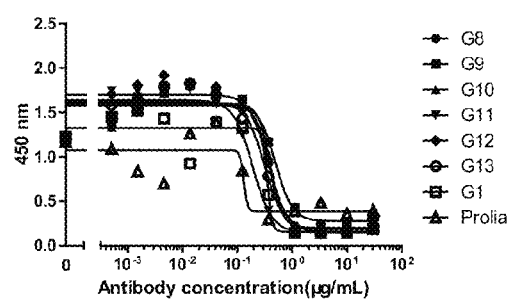
Figure 15C:
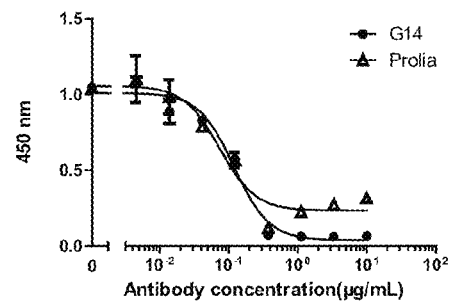

A curve of antibodies competitively inhibiting the bonding of receptor and ligand (see FIG. 15A/15B/15C) is obtained using log (agonist) vs. response—variable slope potting method with the antibody concentration as abscissa and the absorbance value of each well as ordinates (GraphPad Prism Software). The results show that, 13 humanized antibodies have significant inhibition activity and are capable of inhibiting the bonding of RANK-Fc and hRANKL concentration-dependently. The measured IC50 values for Prolia is 0.13 µg/ml, IC50 values for 13 humanized antibodies are in a range of 0.1-0.4 µg/ml, which are equivalent to the inhibition activity of G1 and Prolia. IC50 values for the humanized antibody competitively inhibiting the bonding of RANK-Fc and hRANKL are shown in Table 19.

TABLE 19

Comparison of IC50 values for the humanized antibody competitively inhibiting the bonding of RANK-Fc and hRANKL

| Plate#01 | Antibody name | G1 | G2 | G3 | G4 | G5 | G6 | G7 | Prolia |
|---|---|---|---|---|---|---|---|---|---|
| | IC50 (µg/ml) | 0.18 | 0.30 | 0.31 | ~0.36 | 0.29 | 0.29 | 0.29 | 0.04 |
| Plate#02 | Antibody name | G8 | G9 | G10 | G11 | G12 | G13 | G1 | Prolia |
| | IC50 (µg/ml) | 0.38 | 0.50 | 0.40 | 0.19 | 0.36 | 0.31 | ~0.35 | ~0.13 |
| Plate#02 | Antibody name | G14 | Prolia | | | | | | |
| | IC50 (µg/ml) | 0.12 | 0.07 | | | | | | |

Example 19 hRANKL Humanized Antibody Inhibits Cell Differentiation Induced RAW264.7 Experiment The hRANKL can induce mice mononuclear macrophage leukemia cell RAW264.7 cells (purchased from Cell Bank of Shanghai Institute) to be differentiated into osteoclasts in vitro. The object of the experiment is to evaluate the activity of the humanized anti-hRANKL antibody inhibiting the cellular differentiation of RAW264.7 induced by hRANKL in vitro, compared with Prolia. Osteoclasts have a characteristic enzyme; i.e., tartrate-resistant acid phosphatase, the degree of RAW264.7 cells being differentiated into osteoclasts may be reflected by the activity of the tartrate-resistant acid phosphatase which is indicated by the readings with OD405 nm using the pNPP chromogenic system. RAW264.7 cells are cultured with DMEM+10% FBS (purchased from Invitrogen) medium, are sub-cultured once every 3-4 days. For detection of the cell activity, the cells in the logarithmic phase are resuspended with α-MEM medium+10% FBS (purchased from Invitrogen). The cell suspension is seeded on 96-well plates in 2000 cell/100 µl, put into an incubator (purchased from Thermo Fisher, specifications Forma 311) at 37° C. with 5% $CO_2$ for 1 hour. The humanized antibody (G2~G14), mouse antibody (G1) and a positive control Prolia are diluted with serum-free α-MEM medium, and mixed with an equal volume of α-MEM medium containing hRANKL and M-CSF, TGF-β. The mixture is seeded on the cell culture plates in 100 µl/well. The final concentration of antibodies are 4, 2, 1, 0.5, 0.25, 0.125 µg/ml respectively, the final concentrations of hRANKL, M-CSF, TGF-β are 150, 20 and 2 ng/ml respectively. A well containing only a mixture of 20 ng/ml M-CSF+2 ng/mL TGF-β is used as a negative control well, and a well containing a mixture of 20 ng/ml M-CSF+2 ng/mL TGF-β+ 150 ng/ml hRANKL is used as a positive control well. The samples are prepared with three wells, and put into an incubator at 37° C., 5% $CO_2$ for 5 days, the cell supernatant is discarded, 100 µl cell lysis buffer (Citrate Buffer pH 5.0+0.5% Triton X-100) is added in each well, the samples are lysed in a refrigerator at 4° C. for 10 min, the cell lysate was diluted at 10 times, 100 μl pNPP chromogenic solution (purchased from Sigma) is added to each well, the samples are incubated at 37° C. for 30 min, then 50 μl stop solution (0.5 M NaOH) is added to each well, and OD405 nm reading is detected using the M5 equipment.

Figure 16A:
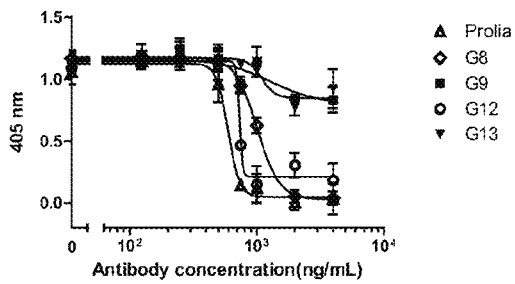
FIGS. 16A-16D show comparison on the activity of the humanized antibody inhibiting RAW264.7 cells to be differentiated into osteoclasts.
Figure 16B:
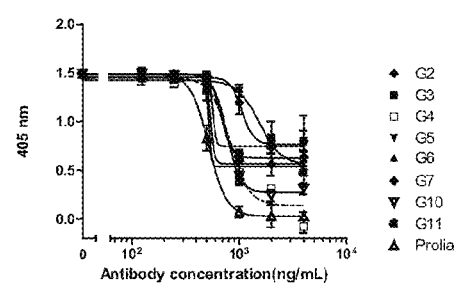
Figure 16C:
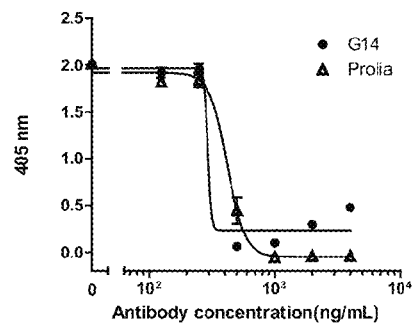
Figure 16D:
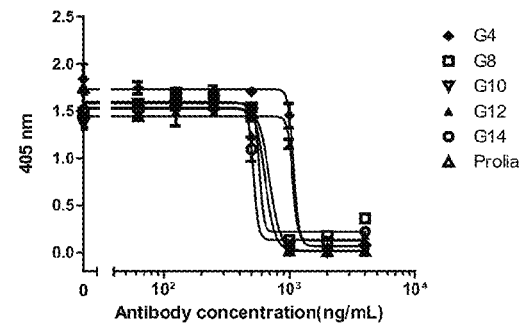

A curve (FIG. 16) of antibodies inhibiting RAW264.7 cells to be differentiated into osteoclasts is obtained using "log (inhibitor) vs. response—Variable slope" potting method with the antibody concentration as abscissa and the absorbance value of each well as ordinates (GraphPad Prism Software). From the graph of FIG. 16A, G9 and G13 have weak inhibition activity, G8 and G12 have good inhibition activity, which is close to the inhibition activity of Prolia; from the graph of FIG. 16B, G4 and G10 have good inhibition activity, which is close to the inhibition activity of Prolia; from the graph of FIG. 16C, G14 has good inhibition activity, which is close to the inhibition activity of Prolia. Based on three groups of experimental data in FIGS. 16A, 16B and 16C, 5 humanized antibodies with better inhibition activity are selected, i.e., G4, G8, G10, G12 and G14. The above 5 humanized antibodies are compared with Prolia under the same experimental conditions. The results show that, IC50 value for Prolia is 635 ng/ml, IC50 values for the 5 humanized antibodies are in a range from 500-1100 ng/ml, and the inhibition activity of three antibodies G8, G10 and G14 are close to the inhibition activity of Prolia. FIG. 16D shows results of 5 humanized antibodies inhibiting the osteoclast differentiation of RAW264.7 which is induced by RANKL. The inhibition activity of humanized antibodies is compared in Table 20.

TABLE 20

Comparison of IC50 value for the humanized antibodies in RAW264.7 cells

| | antibody name | | | | |
|---|---|---|---|---|---|
| | G4 | G8 | G10 | G12 | G14 | Prolia |
| IC50 (ng/ml) | ~1081 | ~572.9 | 695.3 | ~1060 | ~517.4 | 635 |

Example 20 Inhibition Effect of Humanized Antibody on ERK1/2 Phosphorylation of RAW264.7 Cells Induced by hRANKL RAW264.7 cells in the logarithmic phase of Trypsin digestion are resuspended with DMEM+10% FBS medium (purchased from Invitrogen) and the cell density is adjust, the suspension is seeded on 6-well cell culture plates with 3.0×10$^5$ cells/well, and cultured in an incubator at 37° C., 5% CO$_2$. After the cells are attached on wall, the medium is replaced with α-MEM+0.1% FBS (purchased from Invitrogen), and cultured for 24 hours. The antibody and hRANKL are diluted with α-MEM+0.1% FBS. The antibodies (G4, G8, G10, G12, G14) with a final concentration of 250 ng/ml are premixed with 150 ng/ml hRANKL, and incubated at 37° C. for 2 hours, supernatant in 6 wells of the cell culture plate is discarded, the premixed solution is added on the cell culture plate with 1 ml/well, a well containing only Prolia is used as a positive control well, a well containing only α-MEM+0.1% FBS is used as a negative control well. The samples are incubated in an incubator at 37° C. 5% CO$_2$ for 30 minutes. The culture solution is removed, the samples are washed once with pre-cooled 4° C. PBS (137 mM NaCl, 2.7 mM KCl, 10 mM Na$_2$HPO$_4$, 1.8 mM KH$_2$PO$_4$, pH7.4) and then the reaction is terminated. 120 μl LDS (purchased from Invitrogen Corporation, Product Number: NP0007) is added, the samples are placed on ice, the cell lysate are quickly collected, and saved at −80° C. for use.

Figure 17:
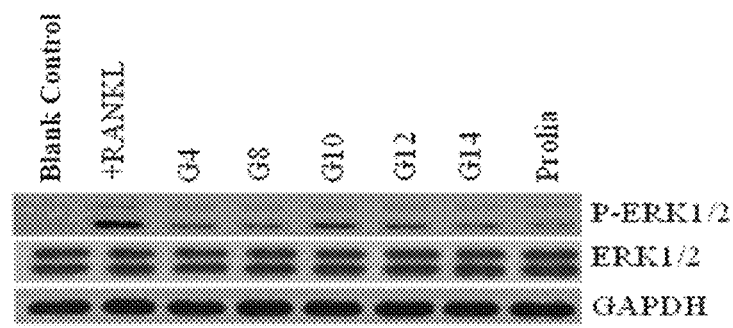
FIG. 17 shows results of the humanized antibody inhibiting RAW264.7 cells induced by hRANKL to be ERK1/2 phosphorylated.

Electrophoresis is performed on the collected cell lysate under the reducing effect of dithiothreitol with a final concentration of 50 mM (D0281 purchased from Sangon, NO. D0281). The gel after electrophoresis is transferred on NC membrane (available from Pall Corporation, Item NO. S80209) with an electrical transfer method. The samples are closed with 5% nonfat dry milk (purchased from Sangon, Num: NB0669), and 1:1000 dilution of rabbit anti-p-ERK1/2 (purchased from Cell Signaling Technology, Item No. 4370), 1:1000 dilution of rabbit anti-ERK1/2 (purchased from Cell Signaling Technology, Item No. 4695), and 1:5000 dilution of rabbit anti-GAPDH (Cell Signaling Technology, Item No. 5174) are added. The samples are incubated overnight at 4° C. The membrane is washed three times with 1×TBST, then 1:10000 dilution of HRP-labeled goat anti-rabbit antibody (commercially available from MERCK, Number: 401315) is added, the membrane is washed three times with 1×TBST, and ECL (available from Perkin Elmer, Num: NEL104001EA) is added for development. Signals are recorded with a film (available from Kodak, Catalogue No.: FF057). The effect of antibody on ERK1/2 phosphorylation of RAW264.7 cells induced by hRANKL is analyzed. The results in FIG. 17 show that, compared with the control group without hRANKL, hRANKL induces the ERK1/2 phosphorylation in RAW264.7 cells to be increased, G4, G8, G10, G12, G14 can inhibit the upregulation effect of hRANKL on ERK1/2 phosphorylation in RAW264.7 cells, which is consistent with the inhibition effect of Prolia.

Embodiment 21

Expression and Purification of Humanized Antibodies in CHO-S Cells

The full length heavy chain (SEQ ID No:50) of antibodies G14 and the full length light chain (SEQ ID No:52) of antibodies G10 are combined to produce humanized antibodies G15. Because the antibodies G14 and G10 may be produced through co-transfecting the light and heavy chain plasmids mentioned in embodiment 16 into 293F cells under the mediation of PEI; similarly, the antibodies G15 may also be produced using the same method expression, which is one of the methods for obtaining humanized antibodies G15.

Another method for obtaining humanized antibodies G15 is as follows: in order to obtain more humanized antibody proteins, the CHO-S cell line developing platform of Huabo Biopharm (Shanghai) Co., Ltd is adopted herein to respectively build the heavy chain and light chain genes of antibodies G8, G14 and G15 onto a pHB carrier, wherein the carrier contains glutaminesynthetase gene (glutaminesynthetase, GS), and may be pressurized and screened through methionine sulfoximine (methionine sulfoximine, MSX).

pHB-G14 (SEQ ID No:50) heavy chain plasmid and pHB-G10 (SEQ ID No:52) light chain plasmid are mixed in equal quantity, electroplated into CHO-S cell using a Biorad electroporator (Item NO. 165-2660), then re-suspended using a 10 ml medium, stood and cultured in an incubator at 37° C. with 5% CO$_2$, then the cell is centrifuged and the medium is changed on next day, bisected to two T75 culture flasks for MSX pressurizing and screening. The cell growth conditions are observed in every other day, the screening pressure is increased after two weeks, and then the cells are seeded and amplified with 3~5×10$^5$ cells/mL, and finally amplified to eight 2 L shake flasks (each flask is 550 mL) to start producing proteins of antibodies G15. In each day, sampling and counting are performed, and glucose concentration is detected, supplementary concentrated solution is added according to the cell growth situation, and cooling culture is conducted. On the thirteenth day, the culture is finished, and supernatant is obtained. Then centrifuging operation is performed at 2000 rpm for 10 min to obtain cell supernatant which is clarified by a hollow fiber column to obtain about 6 L clarified liquor, and purified antibodies are obtained through ProteinA purification. AKATA purifier is connected to BGL ProteinA column (100 ml column volume), an equilibrium liquid (25 mM Tris-HCl+75 mM NaCl, pH7.4) is firstly used to equilibrate the column, samples are loaded at a flow rate of 20 ml/min, then unbonded impure proteins are removed by washing through the equilibrium liquid, and object antibodies bonded on the column are eluted suing 100 mM sodium acetate (pH3.5), the pH of the elution fractions is adjusted to neutrality, and the protein concentration is determined using UV280.

pHB-G8 (SEQ ID No:48) heavy chain plasmid and pHB-G8 (SEQ ID No:54) light chain plasmid are mixed in equal quantity, and electroplated into CHO-S cell to produce proteins of antibodies G8; pHB-G14 (SEQ ID No:50) heavy chain plasmid and pHB-G14 (SEQ ID No:56) light chain plasmid are mixed in equal quantity, and electroplated into CHO-S cell to produce proteins of antibodies G14. The specific screening and preparing methods are ditto, and will not be described in details herein.

Embodiment 22

Analysis and Detection of Antibody Quality Using SDS-PAGE Method

Figure 18A:
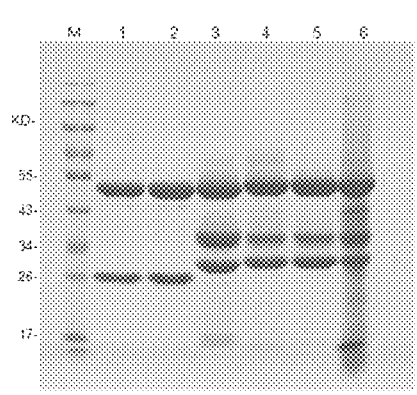
FIG. 18A shows reducing SDS-PAGE detection results of G8 and G14 antibodies expressed by CHO-S cell, wherein 1 and 2 represent a reference product (IgG1), and 3 represents PA elution fraction filtrate (pH7.0) of G8; 4 represents PA elution fraction supernatant (pH7.0) of G14, and 5 represents PA elution fraction filtrate (pH7.0) of G14; 6 represent deposits in PA elution fraction of G14.
Figure 18B:
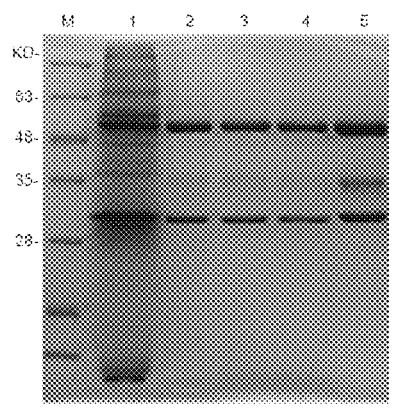
FIG. 18B shows a reducing SDS-PAGE detection result of G15 antibody expressed by CHO-S cell, wherein 1 represents supernatant concentrated solution of G15, 2 represents PA elution fraction (pH3.0) of G15, 3 represents PA elution fraction (pH5.0) of G15, 4 represents PA elution fraction (pH7.0) of G15, and 5 represents PA elution fraction (pH7.0) of G14. "M" in the two figures represent prestained protein standard sample, "KD" represents a protein unit kilodalton, and "PA" represents ProteinA purification.

20 μl purified antibodies G8, G14 and G15 mentioned above are taken, and ¼ volumetric 4× protein loading buffer (Life, Item NO. NP0007, Lot NO. 1606369) and 3% 1M DTT are respectively added, blended evenly, and then heated in a metal bath at 95° C. for 5 min, centrifuged at 12000 rpm for 2 min, 10 ul supernatant is taken and added to reducing SDS-PAGE gel (4% concentration gel, 10% separation gel), subjected to electrophoresis at 80V, then the voltage is regulated to 160V when gel is separated from the sample, and electrophoresis is stopped when bromophenol blue indicator arrives the bottom edge. The gel is taken out and put into a Commassie blue staining solution to stain for 1 h. Surface dyeing of the gel is washed by water, then the gel is immersed into a destaining solution to decolorize till the protein is clear to see, and finally a Bio-Rad gel imaging system (ChemiDocTMXRS+) is used for photographing, which is as shown in FIG. 18A and FIG. 18B. Analyzing from the electrophoresis results, the heavy chain of the antibodies G8, G14 and G15 after being reduced is about 50 KD, and the light chain thereof is about 28 KD, which are substantially in accordance with theoretical size. In FIG. 18B, the ProteinA elution fraction of antibodies G15 is relatively stable under pH3.0~7.0, and is best in a pH7.0 buffer solution; but in FIG. 18A, both the antibodies G8 and G14 have apparent impure zones at 34 KD position in a pH7.0 buffer solution, and antibody purities are only about 80%; in contrast, the purity of the antibody G15 in FIG. 18B is about 90%, which is apparently higher than that of the G8 and G14. It can be thus deduced that the molecules of antibodies G15 are easier to purification and are stable, which are more suitable for process developing.

Embodiment 23

Figure 19:
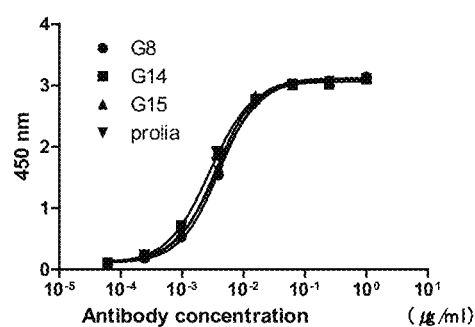
FIG. 19 shows a bonding curve of humanized antibodies G8, G14 and G15 expressed by CHO-S cell and antigen hRANKL compared with Prolia.

Detection of the Bonding Ability Between the Humanized Antibodies and hRNAKL Using ELISA Method The bonding ability between the humanized antibodies G8, G14 and G15 expressed by CHO-S and the antigen hRNAKL are detected according to the method in embodiment 17. A bonding curve of antibodies and hRANKL (FIG. 19) is obtained using log(agonist) vs. response—Variable slope potting method with the antibody concentration as abscissa and the absorbance value of each well as ordinates (GraphPad Prism Software). The results show that 3 humanized antibodies are capable of bonding to hRANKL concentration-dependently and can reach saturation; when the Prolia reaches the 50% maximum degree of bonding, the antibody concentration for Prolia (EC50) is 3.75 ng/ml, the EC50 values of G8, G14 and G15 are respectively 4.05, 2.09 and 3.56 ng/ml, which are equivalent to Prolia (denosumab produced by Amgen).

Embodiment 24

Figure 20:
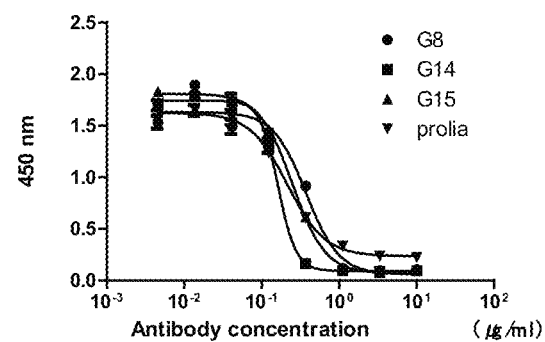
FIG. 20 shows a curve of humanized antibodies G8, G14 and G15 expressed by CHO-S cell for competitively inhibiting the bonding of hRANKL and RANK compared with Prolia.

Detection of the Inhibition Ability of Humanized Antibodies for the Bonding of RANK-Fc and hRANKL Using Competitive ELISA Method The inhibition ability of humanized antibodies G8, G14, and G15 expressed by CHO-S for the bonding of RANK-Fc and hRANKL is detected according to the method in embodiment 18. A curve of antibodies competitively inhibiting the bonding of receptor and ligand (see FIG. 20) is obtained using log (agonist) vs. response—Variable slope potting method (GraphPad Prism software) with the antibody concentration logarithm as abscissa and the absorbance value measured as ordinates (GraphPad Prism Software). The results show that 3 humanized antibodies all have significant inhibition activity and are capable of inhibiting the bonding of RANK-Fc and hRANKL, and are concentration-dependent. When reaches the 50% maximum degree of inhibition, the measured antibody concentration (IC50) for Prolia is 0.21 μg/ml, IC50 values for 3 humanized antibodies are respectively 0.37, 0.16 and 0.25 μg/ml, which are equivalent to the inhibition effect of G1 and Prolia.

Embodiment 25

Figure 21:
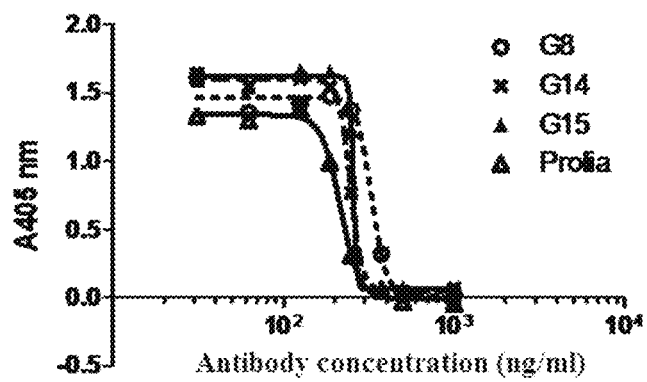
FIG. 21 shows a hRANKL induced RAW264.7 cell differentiation curve inhibited by humanized antibodies G8, G14 and G15 expressed by CHO-S cell compared with Prolia.

Experiment of the Humanized Antibodies for Inhibiting hRANKL Induced RAW264.7 Cell Differentiation The activity of the humanized anti-hRANKL antibody for inhibiting in vitro RAW264.7 cell differentiation induced by hRANKL is detected and compared with Prolia according to the method in embodiment 19. A curve (FIG. 21) of antibodies inhibiting RAW264.7 cells to be differentiated into osteoclasts is obtained using "log (inhibitor) vs. response—Variable slope" potting method with the antibody concentration logarithm as abscissa and the absorbance value measured as ordinates (GraphPad Prism Software). From the graph of FIG. 21, the IC50 value of Prolia for inhibiting cell differentiation is 215.6 ng/ml, and the IC50 values of antibodies G8, G14 and G15 for inhibiting cell differentiation are respectively 329.1, 247.2 and 256.6 ng/ml, which are equivalent to the effect of Prolia on inhibiting the hRANKL induced RAW264.7 cell differentiation.

Embodiment 26

Expression of the Humanized Antibodies in CHO-DG44 Cells and Product Quality Analysis Embodiments 21~25 describe another method for preparing the humanized antibodies. In this method, a combination method of producing the new humanized antibody is found, i.e., the full length heavy chain (SEQ ID No:50) of antibodies G14 and the full length light chain (SEQ ID No:52) of antibody G10 are combined to produce antibody G15. During the course of expression and purification, it is found that antibodies G15 are more stable, and the elution fractions obtained by ProteinA purification are relatively stable under pH3.0~7.0, and the purity displayed by SDS-PAGE are higher than the other two antibodies G8 and G14 bp about 10%. It is believed that G15 molecules are more suitable for process developing. To further determine this extrapolation, the dihydrofolate reductase deficient (DHFR-) Chinese hamster ovary cells (CHO-DG44) (purchased from Life, Item No. 12609-012) platform technology of our corporation is utilized to build molecules of antibodies G14 and G15 on pWBM122 carrier, wherein the carrier contains two sets of independent startup and regular elements, and the heavy chain and light chain of the antibody can be started and expressed on the same 122 carrier. This carrier also contains DHFR genes, stably expressed cells may be pressurized and screened through amethopterin (MTX) (purchased from Sigma, Item NO. M8407), and product quality may be analyzed. The gene with 1441 bp length is synthesized, this gene includes 5' NotI restriction sites, signal peptide, the full length light chain of G15, as well as polyA and EcoRI 3' restriction sites, cut with two enzymes, connected to the 122 carrier using T4 DNA ligase, and transformed into DH5 α under 42° C. thermal shock to obtain recombinant 122 plasmid containing the light chain of G15.

Figure 22:
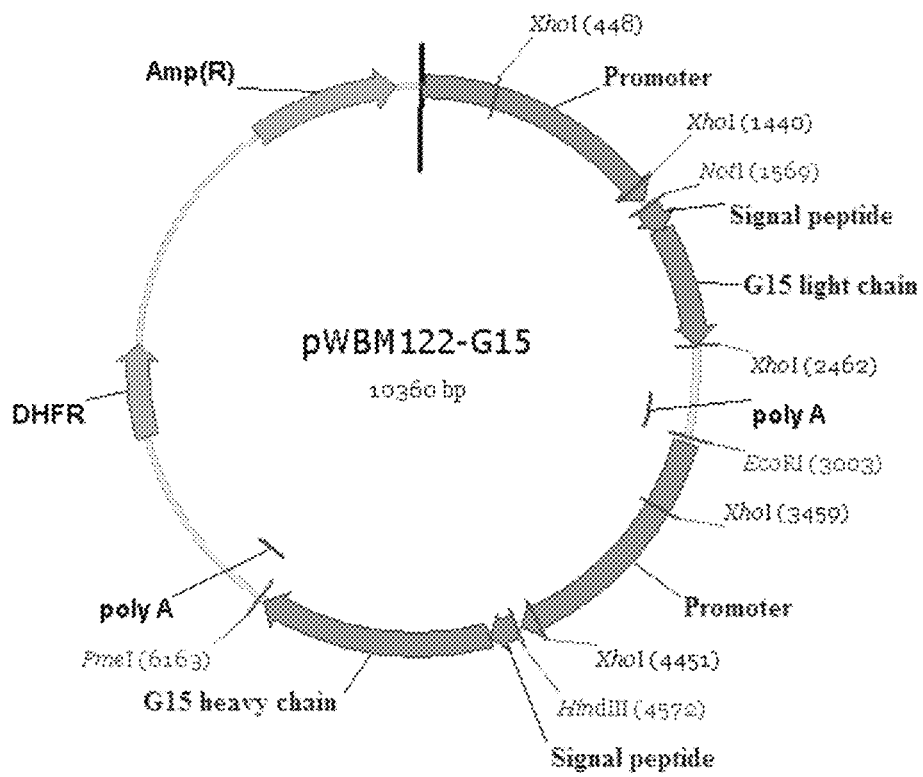
FIG. 22 shows a schematic diagram of recombinant recombinant 122 containing full length heavy chain and light chain genes of G15.

The gene with a 1596 bp length is synthesized, this gene includes 5' HindIII restriction sites, signal peptide, the full length light chain of G15, and PmeI 3' restriction sites, cut with two enzymes, connected to the recombinant 122 carrier, and transformed to finally obtain the recombinant 122 plasmid containing the full length heavy chain and light chain genes of G15, which is named as pWBM122-G15, wherein the plasmid map is as shown in FIG. 22.

40 μg pWBM122-G15 plasmid and 400 μl 1×10$^7$ DG44 cells are mixed and then transferred to a 0.4 cm electric shock cup, and electrically shocked using a Biorad electroporator (Item NO. 165-2660) at 300 V and 900 μF, re-suspended using 10 ml 302 serum free medium (purchased from Sigma, Item NO. 24326C-50L) containing 1% hypoxanthine and thymine (HT) (purchased from Sigma, Item NO. H0137-1VL), subjected to shaking culture at 37° C. 8% $CO_2$ and 130 rpm; after 48 h, the cells are centrifuged and the medium is changed, re-suspended in a 10 ml 302 serum free medium, not including HT for shaking culture. The cell growth conditions are observed, and the cells are sub-cultured once every 3-4 days, wherein the sub-cultured density is 4-6×10$^5$/ml. If the sub-cultured proportion is less than 3, then centrifugation is performed and the medium is replaced with a fresh medium. After two weeks, the cells restore growing, then MTX pressurizing and screening are started. The pressure is gradually increased from 50 nM. After the cells restore growing and the cell viability is greater than 90%, the screening pressure is increased. When the MTX concentration reaches 1000 nM, the yield of protein is not increased any longer, then pressurizing is stopped.

Figure 23:
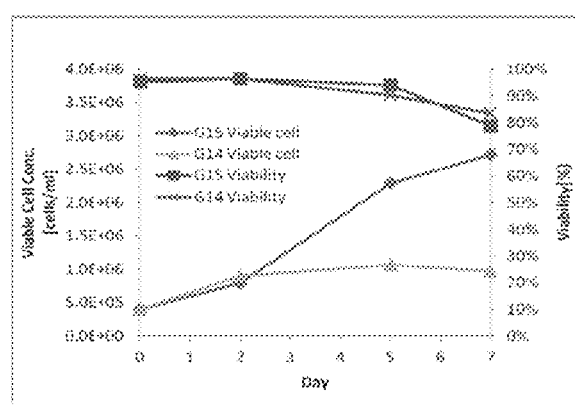
FIG. 23 shows cell growth situation of stable cell population of G15 and G14.

The foregoing pressurized stable cells are seeded in a 80 ml 302 serum free medium according to a density of 4×10$^5$/ml. Sampling is conducted in every other day, and the cell density and cell viability are determined using Cedex cell counter (purchased from Roche, Model CedexHiRes). In the seventy day, the cell viability drops to 78.7%, then culture is stopped and the supernatant is collected, wherein the cell monitoring data is as shown in FIG. 23). Methods for building and expressing the antibodies G14 is ditto, and will not be described in details herein. Growing of G14 cells are monitored using the same method as G15 cells, and data is as shown in FIG. 23.

According to analysis for the growing curve shown in FIG. 23, there is a positive relation between the number of G15 viable cells and culture days in Small Down Process (abbreviated SDP). The cell viability is still above 90% at first five days, and cell density in 302 medium is up to the maximum of 2.7×10$^6$/ml at the seventh day, that is, total cells grow well. In contrast, G14 cells only grow slowly at first two days, and stop to grow since then. Thus, it is believe that G15 is more suitable for construction of a stable transfected cell line for process production.

Since growth defect of G14 cells is completely obvious based on the growing curve shown in FIG. 23, there is no purification and quality analysis for antibodies expressed by G14 cells.

Figure 24:
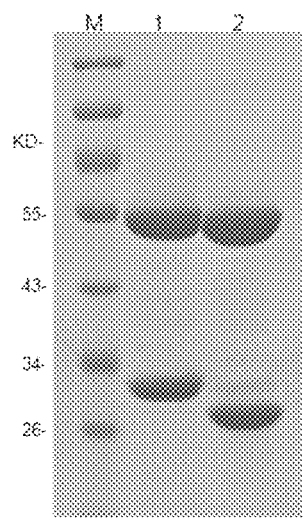
FIG. 24 shows reducing SDS-PAGE detection results of antibody G15 expressed by CHO-DG44 cell, wherein 1 represents PA elution fraction (pH7.0) of G15, 2 represents Prolia, "M" represents prestained protein standard sample, and "KD" represents protein unit kilodalton.

The cell supernatant is obtained by centrifuging the G15 cell culture medium at 2000 rpm for 10 min, and purified antibodies are obtained through ProteinA purification. The antibodies G15 expressed by DG44 cell are analyzed according to the SDS-PAGE method in embodiment 22, and Prolia is taken as a positive reference sample, wherein the electrophoresis results are as shown in FIG. 24. Analyzing from the electrophoresis results in FIG. 24, the heavy chain of the antibodies G15 after being reduced is about 50 KD, and the light chain thereof is about 28 KD, which are substantially in accordance with theoretical size. The purity of the antibodies G15 is greater than 95%, which is higher than the purity expressed by CHO-S cell by 5%, and the product quality is better. It can be thus determined that the antibodies G15 are the best anti-hRANKL humanized antibody molecules, and are suitable for process developing.

7.19.12 murine antibodies are humanized with humanization techniques according to the present disclosure, so as to obtain humanized antibodies with an increased humanized degree and the antigen-antibody affinity. 7.19.12 murine antibodies are humanized with humanization techniques according to the present disclosure and a series of humanized antibodies are obtained through series of screening, and the bonding properties of the humanized antibodies are consistent with that of murine antibodies through immunological and cytological experiments. The humanized antibodies have neutralizing activity which can inhibit the competitive bonding of RANKL and receptors RANK, and effectively inhibit the RANKL-induced differentiation of osteoclasts in vitro. Therefore, it is inferred that these monoclonal antibodies should effectively inhibit bone absorption and osteoporosis in vivo. These humanized antibodies are prepared using mammalian cells or prokaryotic system, can become a suitable clinical pharmacology therapeutic monoclonal antibody drugs, and can used to treat osteoporosis, bone destruction of bone joint caused by rheumatoid arthritis, bone destruction caused by bone metastasis from tumor, bone destruction caused by the growth of giant cell tumor, and other pathological changes such as bone loss or bone destruction due to osteoclast hyperfunction induced by RANKL by intravenous or subcutaneous administration.

The antibodies according to the invention are humanized antibodies, for which nucleic acid sequences and amino acid sequences in their variable regions and constant regions have no similarities compared with fully humanized antibody Prolia. The sequences and structures of the humanized antibodies according to the invention are unique and novel.

The invention claimed is:
1. An anti-human RANKL monoclonal antibody, wherein the anti-human RANKL monoclonal antibody comprises a heavy chain and a light chain, wherein a) the heavy chain comprises a variable region, the sequence of which is one of amino acid sequences SEQ ID NO.2-9, and b) the light chain comprises a variable region, the sequence of which is one of amino acid sequences SEQ ID NO.10-17; and the antibody binds with RANKL to block an interaction between RANK and RANKL, or a human RANKL binding fragment of such antibody.

2. The anti-human RANKL monoclonal antibody according to claim 1, wherein the antibody comprises a heavy chain and a light chain, wherein the heavy chain comprises a variable region with the amino acid sequence of SEQ ID NO. 2, and the light chain comprises a variable region with the amino acid sequence of SEQ ID NO.10; or, the heavy chain comprises a variable region with the amino acid sequence of SEQ ID NO. 3, and the light chain comprises a variable region with the amino acid sequence of SEQ ID NO.11; or, the heavy chain comprises a variable region with the amino acid sequence of SEQ ID NO. 4, and the light chain comprises a variable region with the amino acid sequence of SEQ ID NO.12; or, the heavy chain comprises a variable region with the amino acid sequence of SEQ ID NO. 5, and the light chain comprises a variable region with the amino acid sequence of SEQ ID NO.13; or, the heavy chain comprises a variable region with the amino acid sequence of SEQ ID NO. 6, and the light chain comprises a variable region with the amino acid sequence of SEQ ID NO.14; or, the heavy chain comprises a variable region with the amino acid sequence of SEQ ID NO. 7, and the light chain comprises a variable region with the amino acid sequence of SEQ ID NO.15; or, the heavy chain comprises a variable region with the amino acid sequence of SEQ ID NO. 8, and the light chain comprises a variable region with the amino acid sequence of SEQ ID NO.16; or, the heavy chain comprises a variable region with the amino acid sequence of SEQ ID NO. 9, and the light chain comprises a variable region with the amino acid sequence of SEQ ID NO.17.

3. The anti-human RANKL monoclonal antibody according to claim 1, wherein the antibody comprises a heavy chain and a light chain, wherein the heavy chain comprises a variable region with the amino acid sequence of SEQ ID NO. 6, and the light chain comprises a variable region with the amino acid sequence of SEQ ID NO.14.

4. The anti-human RANKL monoclonal antibody according to claim 1, wherein the anti-human RANKL monoclonal antibody is a single-chain antibody, a humanized antibody, or a murine monoclonal antibody obtained by means of hybridoma technique.

5. A humanized anti-human RANKL monoclonal antibody according to claim 1, wherein the humanized monoclonal antibody is capable of binding specifically with human RANKL and comprises a variable region in a heavy chain of the humanized monoclonal antibody with an amino acid sequence selected from amino acid sequences SEQ ID NO.6, NO.23, NO.25, NO.27 or NO.29, and a variable region in a light chain of the humanized monoclonal antibody with an amino acid sequence selected from amino acid sequences SEQ ID NO.14, NO.31, NO.33, NO.35, NO.37 or NO.39.

6. The humanized monoclonal antibody according to claim 5, wherein the variable region in the heavy chain comprises amino acids with the sequence of SEQ ID NO.6, and the variable region in the light chain comprises amino acids with the sequence of SEQ ID NO.14; or
the variable region in the heavy chain comprises amino acids with the sequence of SEQ ID NO.23, and the variable region in the light chain comprises amino acids with the sequence of SEQ ID NO. 31; or
the variable region in the heavy chain comprises amino acids with the sequence of SEQ ID NO.23, and the variable region in the light chain comprises amino acids with the sequence of SEQ ID NO.35; or
the variable region in the heavy chain comprises amino acids with the sequence of SEQ ID NO.23, and the variable region in the light chain comprises amino acids with the sequence of SEQ ID NO.33; or
the variable region in the heavy chain comprises amino acids with the sequence of SEQ ID NO.23, and the variable region in the light chain comprises amino acids with the sequence of SEQ ID NO.37; or
the variable region in the heavy chain comprises amino acids with the sequence of SEQ ID NO.27, and the variable region in the light chain comprises amino acids with the sequence of SEQ ID NO.31; or
the variable region in the heavy chain comprises amino acids with the sequence of SEQ ID NO.27, and the variable region in the light chain comprises amino acids with the sequence of SEQ ID NO.35; or
the variable region in the heavy chain comprises amino acids with the sequence of SEQ ID NO.27, and the variable region in the light chain comprises amino acids with the sequence of SEQ ID NO.33; or
the variable region in the heavy chain comprises amino acids with the sequence of SEQ ID NO.27, and the variable region in the light chain comprises amino acids with the sequence of SEQ ID NO.37; or
the variable region in the heavy chain comprises amino acids with the sequence of SEQ ID NO.25, and the variable region in the light chain comprises amino acids with the sequence of SEQ ID NO.31; or
the variable region in the heavy chain comprises amino acids with the sequence of SEQ ID NO.25, and the variable region in the light chain comprises amino acids with the sequence of SEQ ID NO.35; or
the variable region in the heavy chain comprises amino acids with the sequence of SEQ ID NO.25, and the variable region in the light chain comprises amino acids with the sequence of SEQ ID NO.33; or
the variable region in the heavy chain comprises amino acids with the sequence of SEQ ID NO.25, and the variable region in the light chain comprises amino acids with the sequence of SEQ ID NO.37; or
the variable region in the heavy chain comprises amino acids with the sequence of SEQ ID NO.29, and the variable region in the light chain comprises amino acids with the sequence of SEQ ID NO.39; or
the variable region in the heavy chain comprises amino acids with the sequence of SEQ ID NO.29, and the variable region in the light chain comprises amino acids with the sequence of SEQ ID NO.31.

7. The humanized monoclonal antibody according to claim 5, wherein a constant region in the heavy chain of the humanized monoclonal antibody is human IgG2, and a constant region in the light chain of the humanized monoclonal antibody is human Kappa; or, a constant region in the heavy chain of the humanized monoclonal antibody is amino acids with the sequence of SEQ ID NO.41, and a constant region in the light chain of the humanized monoclonal antibody is amino acids with the sequence of SEQ ID NO.43.

8. The humanized monoclonal antibody according to claim 5, wherein the humanized monoclonal antibody is an antigen binding segment selected from Fab, Fab' or F(ab')₂.

9. The humanized monoclonal antibody according to claim 7, wherein the heavy chain of the humanized monoclonal antibody has an amino acid sequence selected from an amino acid sequence of one of SEQ ID NOs.: 46-50, or the light chain of the humanized monoclonal antibody is has an amino acid sequence selected from an amino acid sequence of one of SEQ ID NOs.: 51-56.

10. The humanized monoclonal antibody according to claim 9, wherein the complete heavy chain of the humanized monoclonal antibody comprises the amino acid sequence of SEQ ID NO. 46, the complete light chain of the humanized monoclonal antibody comprises the amino acid sequence of SEQ ID NO.51; or, the complete heavy chain of the humanized monoclonal antibody comprises the amino acid sequence of SEQ ID NO.47, the complete light chain of the humanized monoclonal antibody comprises the amino acid sequence of SEQ ID NO.52, NO.53, NO.54 or NO.55; or, the complete heavy chain of the humanized monoclonal antibody comprises the amino acid sequence of SEQ ID NO. 48, the complete light chain of the humanized monoclonal antibody comprises the amino acid sequence of SEQ ID NO.52, NO.53, NO.54 or NO.55; or, the complete heavy chain of the humanized monoclonal antibody comprises the amino acid sequence of SEQ ID NO.49, the complete light chain of the humanized monoclonal antibody comprises the amino acid sequence of SEQ ID NO.52, NO.53, NO.54 or NO.55; or, the complete heavy chain of the humanized monoclonal antibody comprises the amino acid sequence of SEQ ID NO.50, the complete light chain of the humanized monoclonal antibody comprises the amino acid sequence of SEQ.ID NO.52 or NO.56.

11. The humanized monoclonal antibody according to claim 7, wherein the variable region in the heavy chain comprises the amino acid sequence of SEQ ID NO. 6 and the constant region in the heavy chain comprises the amino acid sequence of SEQ ID NO. 41, or the variable region in the light chain comprises the amino acid sequence of SEQ ID NO.14, and the constant region in the light chain comprises the amino acid sequence of SEQ ID NO.43; or, the variable region in the heavy chain comprises an amino acid sequence of SEQ ID NO.23 and the constant region in the heavy chain comprises the amino acid sequence of SEQ ID NO.41, or the variable region in the light chain comprises the amino acid sequence of SEQ ID NO.31 and the constant region in the light chain comprises the amino acid sequence of SEQ ID NO.43; or, the variable region in the heavy chain comprises the amino acid sequence of SEQ ID NO.23 and the constant region in the heavy chain comprises the amino acid sequence of SEQ ID NO.41, or the variable region in the light chain comprises the amino acid sequence of SEQ ID NO.35 and the constant region in the light chain comprises the amino acid sequence of SEQ ID NO.43; or, the variable region in the heavy chain comprises the amino acid sequence of SEQ ID NO.23 and the constant region in the heavy chain comprises the amino acid sequence of SEQ ID NO.41, or the variable region in the light chain comprises the amino acid sequence of SEQ ID NO.33 and the constant region in the light chain comprises the amino acid sequence of SEQ I-D NO.43; or, the variable region in the heavy chain comprises the amino acid sequence of SEQ ID NO.23 and the constant region in the heavy chain comprises the amino acid sequence of SEQ ID NO.41, or the variable region in the light chain comprises the amino acid sequence of SEQ ID NO.37 and the constant region in the light chain comprises the amino acid sequence of SEQ ID NO.43; or, the variable region in the heavy chain comprises the amino acid sequence of SEQ ID NO.27 and the constant region in the heavy chain comprises the amino acid sequence of SEQ ID NO.41, or the variable region in the light chain comprises the amino acid sequence of SEQ ID NO.31 and the constant region in the light chain comprises the amino acid sequence of SEQ ID NO.43; or, the variable region in the heavy chain comprises the amino acid sequence of SEQ ID NO.27 and the constant region in the heavy chain comprises the amino acid sequence of SEQ ID NO.41, or the variable region in the light chain comprises the amino acid sequence of SEQ ID NO.35 and the constant region in the light chain comprises the amino acid sequence of SEQ ID NO.43; or, the variable region in the heavy chain comprises the amino acid sequence of SEQ ID NO.27 and the constant region in the heavy chain comprises the amino acid sequence of SEQ ID NO.41, or the variable region in the light chain comprises the amino acid sequence of SEQ ID NO.33 and the constant region in the light chain comprises the amino acid sequence of SEQ ID NO.43; or, the variable region in the heavy chain comprises the amino acid sequence, of SEQ ID NO.27 and the constant region in the heavy chain comprises the amino acid sequence of SEQ ID NO.41, or the variable region in the light chain comprises the amino acid sequence of SEQ ID NO.37 and the constant region in the light chain comprises the amino acid sequence of SEQ ID NO.43; or, the variable region in the heavy chain comprises the amino acid sequence of SEQ ID NO.25 and the constant region in the heavy chain comprises the amino acid sequence of SEQ ID NO.41, or the variable region in the light chain comprises the amino acid sequence of SEQ ID NO.31 and the constant region in the light chain comprises the amino acid sequence of SEQ ID NO.43; or, the variable region in the heavy chain comprises the amino acid sequence of SEQ ID NO.25 and the constant region in the heavy chain comprises the amino acid sequence of SEQ ID NO.41, or the variable region in the light chain comprises the amino acid sequence of SEQ ID NO.35 and the constant region in the light chain comprises the amino acid sequence of SEQ ID NO.43; or, the variable region in the heavy chain comprises the amino acid sequence of SEQ ID NO.25 and the constant region in the heavy chain comprises the amino acid sequence of SEQ ID NO.41, or the variable region in the light chain comprises the amino acid sequence of SEQ ID NO.33 and the constant region in the light chain comprises the amino acid sequence of SEQ ID NO.43; or, the variable region in the heavy chain comprises the amino acid sequence of SEQ ID NO.25 and the constant region in the heavy chain comprises the amino acid sequence of SEQ ID NO.41, or the variable region in the light chain comprises the amino acid sequence of SEQ ID NO.37 and the constant region in the light chain comprises the amino acid sequence of SEQ ID NO.43; or, the variable region in the heavy chain comprises the amino acid sequence of SEQ ID NO.29 and the constant region in the heavy chain comprises the amino acid sequence of SEQ ID NO.41, or the variable region in the light chain comprises the amino acid sequence of SEQ ID NO.39 and the constant region in the light chain comprises the n amino acid sequence of SEQ ID NO.43; or, the variable region in the heavy chain comprises the amino acid sequence of SEQ ID NO.29 and the constant region in the heavy chain comprises the amino acid sequence of SEQ ID NO.41, or the variable region in the light chain comprises the amino acid sequence of SEQ ID NO.31 and the constant region in the light chain comprises the amino acid sequence of SEQ ID NO.43.

12. A pharmaceutical composition, which comprises the anti-human RANKL monoclonal antibody according to claim 1.

13. A pharmaceutical composition, which comprises the anti-human RANKL monoclonal antibody according to claim 5.

14. A pharmaceutical composition, which comprises the anti-human RANKL monoclonal antibody according to claim 6.

15. A pharmaceutical composition, which comprises the anti-human RANKL monoclonal antibody according to claim 7.

16. The humanized monoclonal antibody according to claim 6, wherein the variable region in the heavy chain of the humanized monoclonal antibody is the amino acid sequence of SEQ ID NO.29, and the variable region in the light chain of the humanized monoclonal antibody is selected from amino acid sequences of SEQ ID NO.31 or SEQ ID NO.39.

17. The humanized monoclonal antibody according to claim 16, wherein a constant region in the heavy chain of the humanized monoclonal antibody is human IgG2, and a constant region in the light chain of the humanized monoclonal antibody is human Kappa; or, a constant region in the heavy chain of the humanized monoclonal antibody has the amino acid sequence of SEQ ID NO.41, and a constant region in the light chain of the humanized monoclonal antibody has the amino acid sequence of SEQ ID NO.43.

18. The humanized monoclonal antibody according to claim 16, wherein the humanized monoclonal antibody is an antigen binding segment selected from Fab, Fab' or F(ab')$_2$.

19. The humanized monoclonal antibody according to claim 9, wherein the complete heavy chain of the humanized monoclonal antibody has the amino acid sequence of SEQ ID NO.50, and the complete light chain of the humanized monoclonal antibody is selected from an amino acid sequence of SEQ ID NO.52 or SEQ ID NO.56.

20. The humanized monoclonal antibody according to claim 11, wherein the variable region in the heavy chain comprises the amino acid sequence of SEQ ID NO. 29, the constant region in the heavy chain comprises the amino acid sequence of SEQ ID NO.41, the variable region in the light chain comprises the amino acid sequence of SEQ ID NO.39 and the constant region in the light chain comprises the amino acid sequence of SEQ ID NO.43, or the variable region in the heavy chain comprises the amino acid sequence of SEQ ID NO. 29, the constant region in the heavy chain comprises the amino acid sequence of SEQ ID NO. 41, the variable region in the light chain comprises the amino acid sequence of SEQ ID NO.31 and the constant region in the light chain comprises the amino acid sequence of SEQ ID NO.43.

21. A pharmaceutical composition, which comprises the humanized monoclonal antibody of claim 16.

\* \* \* \* \*